(12) United States Patent
Panescu et al.

(10) Patent No.: US 11,751,939 B2
(45) Date of Patent: Sep. 12, 2023

(54) METHODS AND DEVICES FOR ENDOVASCULAR ABLATION OF A SPLANCHNIC NERVE

(71) Applicant: AXON THERAPIES, INC., New York, NY (US)

(72) Inventors: Dorin Panescu, San Jose, CA (US); Andrew Wu, Los Altos Hills, CA (US); Zoar Jacob Engelman, New York, NY (US); Mark Gelfand, New York, NY (US); Mark S. Leung, Duncan (CA)

(73) Assignee: Axon Therapies, Inc., New York, NY (US)

( * ) Notice: Subject to any disclaimer, the term of this patent is extended or adjusted under 35 U.S.C. 154(b) by 270 days.

(21) Appl. No.: 16/963,559

(22) PCT Filed: Jan. 28, 2019

(86) PCT No.: PCT/US2019/015400
§ 371 (c)(1),
(2) Date: Jul. 21, 2020

(87) PCT Pub. No.: WO2019/148094
PCT Pub. Date: Aug. 1, 2019

(65) Prior Publication Data
US 2021/0128229 A1 May 6, 2021

Related U.S. Application Data

(60) Provisional application No. 62/625,183, filed on Feb. 1, 2018, provisional application No. 62/625,195, filed on (Continued)

(51) Int. Cl.
*A61B 18/14* (2006.01)
*A61B 18/12* (2006.01)
(Continued)

(52) U.S. Cl.
CPC ...... *A61B 18/1492* (2013.01); *A61B 18/0218* (2013.01); *A61B 18/1206* (2013.01);
(Continued)

(58) Field of Classification Search
CPC ...... A61B 2018/00577; A61B 18/1477; A61B 2018/1475; A61B 18/1487; A61B 5/6852;
(Continued)

(56) References Cited

U.S. PATENT DOCUMENTS

| 3,301,258 A | 1/1967 | Werner |
| 4,403,985 A | 9/1983 | Boretos |

(Continued)

FOREIGN PATENT DOCUMENTS

| CN | 1219855 A | 6/1999 |
| CN | 101600471 A | 12/2009 |

(Continued)

OTHER PUBLICATIONS

Adamopoulos et al; Comparison of different methods for assessing sympathovagal balance in chronic congestive heart failure secondary to coronary artery disease; The American Journal of Cardiology; 70(20): pp. 1576-1582; Dec. 15, 1992.
(Continued)

*Primary Examiner* — Linda C Dvorak
*Assistant Examiner* — Mystee Nguyen Delgado
(74) *Attorney, Agent, or Firm* — Shay Glenn LLP; Thomas M. Zlogar

(57) ABSTRACT

Systems, devices, and methods for transvascular ablation of target tissue are disclosed herein. The devices and methods may, in some examples, be used for splanchnic nerve ablation to increase splanchnic venous blood capacitance to treat at least one of heart failure and hypertension. For example, the devices disclosed herein may be advanced endovascularly to a target vessel in the region of a thoracic
(Continued)

splanchnic nerve (TSN), such as a greater splanchnic nerve (GSN) or a TSN nerve root. Also disclosed are method of treating heart failure, such as HFpEF, by endovascularly ablating a thoracic splanchnic nerve to increase venous capacitance and reduce pulmonary blood pressure.

18 Claims, 28 Drawing Sheets

Related U.S. Application Data on Feb. 1, 2018, provisional application No. 62/622,407, filed on Jan. 26, 2018.

(51) Int. Cl.
*A61B 18/22* (2006.01)
*A61B 18/00* (2006.01)
*A61B 18/02* (2006.01)
*A61B 90/00* (2016.01)

(52) U.S. Cl.
CPC .. *A61B 18/1477* (2013.01); *A61B 2018/0022* (2013.01); *A61B 2018/00083* (2013.01); *A61B 2018/00267* (2013.01); *A61B 2018/00351* (2013.01); *A61B 2018/00541* (2013.01); *A61B 2018/00577* (2013.01); *A61B 2018/00666* (2013.01); *A61B 2018/00702* (2013.01); *A61B 2018/00791* (2013.01); *A61B 2018/0212* (2013.01); *A61B 2018/126* (2013.01); *A61B 2018/1253* (2013.01); *A61B 2018/144* (2013.01); *A61B 2018/1407* (2013.01); *A61B 2018/1425* (2013.01); *A61B 2018/1435* (2013.01); *A61B 2018/2253* (2017.05); *A61B 2090/3966* (2016.02); *A61B 2218/002* (2013.01)

(58) Field of Classification Search
CPC ... A61B 5/6859; A61B 5/6848; A61B 5/6851; A61B 18/04; A61B 2018/0293; A61B 2018/00583; A61B 2218/002; A61B 5/14503; A61B 18/1492; A61B 18/0218; A61B 18/1206; A61B 2018/00083; A61B 2018/0022; A61B 2018/00267; A61B 2018/00351; A61B 2018/00541; A61B 2018/00666; A61B 2018/00702; A61B 2018/00791; A61B 2018/0212; A61B 2018/1253; A61B 2018/126; A61B 2018/1407; A61B 2018/1425; A61B 2018/1435; A61B 2018/144; A61B 2018/2253; A61B 2090/3966; A61B 5/4041; A61B 5/4836; A61B 2018/00023; A61B 2018/00029; A61B 2018/00273; A61B 2018/00285; A61B 2018/00434; A61B 2018/0262; A61B 2018/1427; A61B 2018/143; A61B 2090/064; A61B 2090/376; A61M 25/01; A61M 25/09; A61M 2025/018; A61M 25/0026; A61M 25/00; A61M 2025/0087; A61M 2025/0092; A61M 5/158; A61N 7/022; A61N 1/0551; A61N 1/36017

See application file for complete search history.

(56) References Cited

U.S. PATENT DOCUMENTS

| | | | |
|---|---|---|---|
| 5,447,529 A | 9/1995 | Marchlinski et al. | |
| 5,454,840 A | 10/1995 | Krakovsky et al. | |
| 5,458,626 A | 10/1995 | Krause | |
| 5,462,545 A | 10/1995 | Wang et al. | |
| 5,569,198 A | 10/1996 | Racchini | |
| 5,649,974 A | 7/1997 | Nelson et al. | |
| 5,658,282 A | 8/1997 | Daw et al. | |
| 5,704,908 A | 1/1998 | Hofmann et al. | |
| 5,722,403 A | 3/1998 | McGee et al. | |
| 5,740,808 A | 4/1998 | Panescu et al. | |
| 5,797,903 A | 8/1998 | Swanson et al. | |
| 5,800,484 A * | 9/1998 | Gough | A61B 18/18 606/41 |
| 5,830,213 A | 11/1998 | Panescu et al. | |
| 5,836,874 A | 11/1998 | Swanson et al. | |
| 5,840,076 A | 11/1998 | Swanson et al. | |
| 5,846,239 A | 12/1998 | Swanson et al. | |
| 5,860,974 A | 1/1999 | Abele | |
| 5,868,736 A | 2/1999 | Swanson et al. | |
| 5,871,483 A | 2/1999 | Jackson et al. | |
| 5,891,136 A | 4/1999 | McGee et al. | |
| 5,925,038 A | 7/1999 | Panescu et al. | |
| 5,928,229 A * | 7/1999 | Gough | A61B 18/18 606/41 |
| 5,961,513 A | 10/1999 | Swanson et al. | |
| 6,044,846 A | 4/2000 | Edwards | |
| 6,058,331 A | 5/2000 | King | |
| 6,071,278 A | 6/2000 | Panescu et al. | |
| 6,099,526 A | 8/2000 | Whayne et al. | |
| 6,123,718 A | 9/2000 | Tu et al. | |
| 6,165,172 A | 12/2000 | Farley et al. | |
| 6,236,886 B1 | 5/2001 | Cherepenin et al. | |
| 6,395,325 B1 | 5/2002 | Hedge et al. | |
| 6,409,722 B1 | 6/2002 | Hoey et al. | |
| 6,425,877 B1 | 7/2002 | Edwards | |
| 6,454,766 B1 | 9/2002 | Swanson et al. | |
| 6,475,213 B1 | 11/2002 | Whayne et al. | |
| 6,569,160 B1 | 5/2003 | Goldin et al. | |
| 6,638,275 B1 * | 10/2003 | McGaffigan | A61B 18/1477 606/41 |
| 6,656,174 B1 | 12/2003 | Hegde et al. | |
| 6,658,279 B2 | 12/2003 | Swanson et al. | |
| 6,658,929 B2 | 12/2003 | Atkinson | |
| 6,668,198 B2 | 12/2003 | Swanson et al. | |
| 6,743,197 B1 | 6/2004 | Edwards | |
| 6,760,616 B2 | 7/2004 | Hoey et al. | |
| 6,832,114 B1 | 12/2004 | Whitehurst et al. | |
| 6,849,073 B2 | 2/2005 | Hoey et al. | |
| 6,885,888 B2 | 4/2005 | Rezai | |
| 6,890,315 B1 | 5/2005 | Levin et al. | |
| 6,954,977 B2 | 10/2005 | Maguire et al. | |
| 6,984,232 B2 | 1/2006 | Vanney et al. | |
| 7,054,689 B1 | 5/2006 | Whitehurst et al. | |
| 7,104,989 B2 | 9/2006 | Skarda | |
| 7,149,574 B2 | 12/2006 | Yun et al. | |
| 7,153,301 B2 | 12/2006 | Swartz et al. | |
| 7,236,822 B2 | 6/2007 | Dobak, III | |
| 7,239,912 B2 | 7/2007 | Dobak, III | |
| 7,282,050 B2 | 10/2007 | Starkebaum et al. | |
| 7,282,051 B2 | 10/2007 | Rioux et al. | |
| 7,285,199 B2 | 10/2007 | Mitsuhashi et al. | |
| 7,326,208 B2 | 2/2008 | Vanney et al. | |
| 7,330,762 B2 | 2/2008 | Boveja et al. | |
| 7,335,377 B2 | 2/2008 | Stem et al. | |
| 7,367,972 B2 | 5/2008 | Francischelli et al. | |
| 7,418,292 B2 | 8/2008 | Shafer | |
| 7,427,280 B2 | 9/2008 | Gerber | |
| 7,449,018 B2 | 11/2008 | Kramer | |
| 7,529,582 B1 | 5/2009 | DiLorenzo | |
| 7,532,938 B2 | 5/2009 | Machado et al. | |
| 7,551,964 B2 | 6/2009 | Dobak, III | |
| 7,599,736 B2 | 10/2009 | DiLorenzo | |
| 7,623,924 B2 | 11/2009 | Narciso, Jr. | |
| 7,689,276 B2 | 3/2010 | Dobak | |
| 7,689,277 B2 | 3/2010 | Dobak, III | |
| 7,702,386 B2 | 4/2010 | Dobak et al. | |
| 7,736,362 B2 | 6/2010 | Eberl et al. | |
| 7,769,442 B2 | 8/2010 | Shafer | |
| 7,778,703 B2 | 8/2010 | Gross et al. | |
| 7,860,570 B2 | 12/2010 | Whitehurst et al. | |
| 7,865,237 B2 | 1/2011 | Machado et al. | |

(56) References Cited

U.S. PATENT DOCUMENTS

| | | |
|---|---|---|
| 7,877,146 B2 | 1/2011 | Rezai et al. |
| 7,921,657 B2 | 4/2011 | Littrup et al. |
| 7,937,145 B2 | 5/2011 | Dobak |
| 8,007,496 B2 | 8/2011 | Rioux et al. |
| 8,155,744 B2 | 4/2012 | Rezai |
| 8,241,273 B2 | 8/2012 | Whayne et al. |
| 8,270,568 B2 | 9/2012 | Pitt |
| 8,295,926 B2 | 10/2012 | Dobak, III |
| 8,321,030 B2 | 11/2012 | Maniak et al. |
| 8,399,443 B2 | 3/2013 | Seward |
| 8,401,667 B2 | 3/2013 | Gustus et al. |
| 8,414,508 B2 | 4/2013 | Thapliyal et al. |
| 8,433,412 B1 | 4/2013 | Westlund et al. |
| 8,473,051 B1 | 6/2013 | Wessels et al. |
| 8,483,835 B2 | 7/2013 | Errico et al. |
| 8,611,496 B2 | 12/2013 | Terunuma et al. |
| 8,676,326 B1 | 3/2014 | Farazi |
| 8,676,362 B2 | 3/2014 | Gabel et al. |
| 8,798,738 B2 | 8/2014 | Machado et al. |
| 8,814,793 B2 | 8/2014 | Brabrand |
| 8,911,439 B2 | 12/2014 | Mayse et al. |
| 8,994,536 B2 | 3/2015 | Margon |
| 8,998,894 B2 | 4/2015 | Mauch et al. |
| 9,005,100 B2 | 4/2015 | Gnanashanmugam et al. |
| 9,022,948 B2 | 5/2015 | Wang |
| 9,028,472 B2 | 5/2015 | Mathur et al. |
| 9,033,969 B2 | 5/2015 | Azamian et al. |
| 9,037,259 B2 | 5/2015 | Mathur |
| 9,072,902 B2 | 7/2015 | Mathur et al. |
| 9,125,661 B2 | 9/2015 | Deem |
| 9,125,668 B2 | 9/2015 | Subramaniam et al. |
| 9,162,075 B2 | 10/2015 | Sluijter et al. |
| 9,174,050 B2 | 11/2015 | Mathur et al. |
| 9,199,091 B2 | 12/2015 | Danek et al. |
| 9,245,182 B2 | 1/2016 | Jania et al. |
| 9,278,196 B2 | 3/2016 | Fischell et al. |
| 9,345,530 B2 | 5/2016 | Ballakur et al. |
| 9,345,900 B2 | 5/2016 | Wu et al. |
| 9,370,657 B2 | 6/2016 | Tehrani et al. |
| 9,439,580 B2 | 9/2016 | Hatlestad et al. |
| 9,439,598 B2 | 9/2016 | Shimada et al. |
| 9,592,386 B2 | 3/2017 | Mathur et al. |
| 9,603,659 B2 | 3/2017 | Subramaniam et al. |
| 9,743,845 B2 | 8/2017 | Wang |
| 9,757,193 B2 | 9/2017 | Zarins et al. |
| 9,895,539 B1 | 2/2018 | Heit et al. |
| 10,207,110 B1 | 2/2019 | Gelfand et al. |
| 10,561,461 B2 | 2/2020 | Panescu et al. |
| 2002/0165532 A1 | 11/2002 | Hill et al. |
| 2002/0198520 A1 | 12/2002 | Coen et al. |
| 2003/0109869 A1 | 6/2003 | Shadduck |
| 2003/0216792 A1 | 11/2003 | Levin et al. |
| 2004/0147837 A1 | 7/2004 | Macaulay et al. |
| 2004/0148019 A1 | 7/2004 | Vidlund et al. |
| 2004/0247849 A1 | 12/2004 | Truckai |
| 2005/0010095 A1 | 1/2005 | Stewart et al. |
| 2005/0015132 A1 | 1/2005 | Kronzon |
| 2005/0203462 A1 | 9/2005 | Katoh et al. |
| 2005/0245923 A1 | 11/2005 | Christopherson et al. |
| 2006/0189972 A1* | 8/2006 | Grossman .......... A61B 18/1477 606/41 |
| 2006/0200121 A1 | 9/2006 | Mowery |
| 2006/0224118 A1 | 10/2006 | Morris et al. |
| 2007/0167984 A1 | 7/2007 | Kieval et al. |
| 2007/0208333 A1 | 9/2007 | Uchida et al. |
| 2007/0213704 A1 | 9/2007 | Truckai et al. |
| 2007/0224253 A1 | 9/2007 | Franklin |
| 2008/0114335 A1 | 5/2008 | Flickinger et al. |
| 2008/0125748 A1 | 5/2008 | Patel |
| 2008/0200972 A1 | 8/2008 | Rittman |
| 2009/0036794 A1 | 2/2009 | Stubhaug et al. |
| 2009/0280178 A1 | 11/2009 | Hedge et al. |
| 2010/0152731 A1 | 6/2010 | de la Rama et al. |
| 2010/0168820 A1 | 7/2010 | Maniak et al. |
| 2010/0185087 A1 | 7/2010 | Nields et al. |
| 2010/0241113 A1 | 9/2010 | Ingle |
| 2010/0249702 A1 | 9/2010 | Magana et al. |
| 2010/0286684 A1 | 11/2010 | Hata et al. |
| 2010/0305664 A1 | 12/2010 | Wingeier et al. |
| 2010/0312295 A1 | 12/2010 | Vase et al. |
| 2011/0022127 A1 | 1/2011 | Averina et al. |
| 2011/0028962 A1 | 2/2011 | Werneth et al. |
| 2011/0098761 A1 | 4/2011 | Wittenberger et al. |
| 2011/0144639 A1 | 6/2011 | Govari |
| 2011/0224750 A1 | 9/2011 | Scheiner |
| 2011/0238083 A1 | 9/2011 | Moll et al. |
| 2011/0313417 A1 | 12/2011 | La Rama et al. |
| 2012/0065554 A1 | 3/2012 | Pikus |
| 2012/0089047 A1 | 4/2012 | Ryba et al. |
| 2012/0089123 A1 | 4/2012 | Organ et al. |
| 2012/0116354 A1 | 5/2012 | Heuser |
| 2012/0136350 A1 | 5/2012 | Goshgarian et al. |
| 2012/0143293 A1 | 6/2012 | Mauch et al. |
| 2012/0265198 A1 | 10/2012 | Crow et al. |
| 2012/0271162 A1 | 10/2012 | Liao et al. |
| 2012/0289369 A1 | 11/2012 | Fogarty |
| 2012/0296329 A1 | 11/2012 | Ng |
| 2013/0023758 A1 | 1/2013 | Fabro |
| 2013/0035682 A1 | 2/2013 | Weil |
| 2013/0096550 A1 | 4/2013 | Hill |
| 2013/0103026 A1 | 4/2013 | Kleshinski et al. |
| 2013/0226201 A1 | 8/2013 | Miller et al. |
| 2013/0237948 A1 | 9/2013 | Donders et al. |
| 2013/0282000 A1 | 10/2013 | Parsonage et al. |
| 2013/0289369 A1 | 10/2013 | Margolis |
| 2013/0296646 A1 | 11/2013 | Barbut et al. |
| 2013/0304047 A1 | 11/2013 | Grunewald et al. |
| 2013/0310823 A1* | 11/2013 | Gelfand .......... A61M 25/0082 606/41 |
| 2013/0331813 A1 | 12/2013 | Barbut et al. |
| 2014/0005706 A1* | 1/2014 | Gelfand .......... A61N 7/022 606/169 |
| 2014/0025069 A1 | 1/2014 | Willard et al. |
| 2014/0031727 A1 | 1/2014 | Warnking |
| 2014/0058294 A1 | 2/2014 | Gross et al. |
| 2014/0058376 A1 | 2/2014 | Horn et al. |
| 2014/0058377 A1 | 2/2014 | Deem et al. |
| 2014/0067003 A1 | 3/2014 | Vase et al. |
| 2014/0088585 A1 | 3/2014 | Hill et al. |
| 2014/0088588 A1 | 3/2014 | Jarrard |
| 2014/0121641 A1 | 5/2014 | Fischell et al. |
| 2014/0121644 A1* | 5/2014 | Fischell .......... A61B 18/1477 604/510 |
| 2014/0180273 A1 | 6/2014 | Nair |
| 2014/0214129 A1 | 7/2014 | Waataja et al. |
| 2014/0276718 A1 | 9/2014 | Turovskiy et al. |
| 2014/0276742 A1 | 9/2014 | Nabutovsky et al. |
| 2014/0303617 A1 | 10/2014 | Shimada |
| 2015/0011834 A1 | 1/2015 | Ayala et al. |
| 2015/0105659 A1 | 4/2015 | Salahieh et al. |
| 2015/0119674 A1 | 4/2015 | Fischell et al. |
| 2015/0141810 A1 | 5/2015 | Weadock |
| 2015/0141985 A1 | 5/2015 | Mayse et al. |
| 2015/0208949 A1 | 7/2015 | Tupin et al. |
| 2015/0223877 A1 | 8/2015 | Behar et al. |
| 2015/0245867 A1 | 9/2015 | Gross |
| 2015/0335286 A1 | 11/2015 | Boydell |
| 2015/0374435 A1 | 12/2015 | Cao et al. |
| 2016/0106499 A1 | 4/2016 | Ogata et al. |
| 2016/0151112 A1 | 6/2016 | Ku et al. |
| 2016/0158554 A1 | 6/2016 | Graig |
| 2016/0163062 A1 | 6/2016 | Garber |
| 2016/0192981 A1 | 7/2016 | Dimmer et al. |
| 2016/0199127 A1 | 7/2016 | Prutchi |
| 2016/0220851 A1 | 8/2016 | Mayse et al. |
| 2016/0296171 A1 | 10/2016 | Drori et al. |
| 2016/0317621 A1 | 11/2016 | Bright |
| 2016/0354137 A1 | 12/2016 | Fischell et al. |
| 2016/0374754 A1 | 12/2016 | Asirvatham et al. |
| 2017/0035990 A1 | 2/2017 | Swift |
| 2017/0049989 A1 | 2/2017 | Kapural |
| 2017/0202614 A1 | 7/2017 | Gross et al. |
| 2017/0216602 A1 | 8/2017 | Waataja et al. |
| 2017/0231490 A1 | 8/2017 | Toth et al. |

(56) References Cited

U.S. PATENT DOCUMENTS

| | | | |
|---|---|---|---|
| 2017/0252101 A1 | 9/2017 | Hata et al. |
| 2018/0036527 A1 | 2/2018 | Reddy et al. |
| 2018/0042669 A1 | 2/2018 | Curley et al. |
| 2018/0110561 A1 | 4/2018 | Levin et al. |
| 2019/0069942 A1 | 3/2019 | Azamian et al. |
| 2019/0175912 A1 | 6/2019 | Gelfand et al. |
| 2019/0298460 A1 | 10/2019 | Al-Jadda et al. |
| 2019/0343581 A1 | 11/2019 | Panescu et al. |
| 2019/0350650 A1 | 11/2019 | Levin et al. |
| 2020/0179045 A1 | 6/2020 | Levin et al. |
| 2020/0179047 A1 | 6/2020 | Panescu et al. |
| 2021/0298824 A1 | 9/2021 | Iranitalab et al. |
| 2021/0393326 A1 | 12/2021 | Levin et al. |
| 2022/0039863 A1 | 2/2022 | Bapana et al. |
| 2022/0338924 A1 | 10/2022 | Levin et al. |

FOREIGN PATENT DOCUMENTS

| | | |
|---|---|---|
| CN | 102670264 A | 9/2012 |
| CN | 102949176 A | 3/2013 |
| CN | 103118619 A | 5/2013 |
| CN | 103220984 A | 7/2013 |
| CN | 103313671 A | 9/2013 |
| CN | 103857353 A | 6/2014 |
| CN | 104066395 A | 9/2014 |
| CN | 104257426 A | 1/2015 |
| EP | 2662027 A1 | 11/2013 |
| EP | 2020943 B1 | 7/2015 |
| EP | 2755588 B1 | 5/2016 |
| EP | 293435781 | 11/2017 |
| JP | 2003526481 A | 9/2003 |
| JP | 2008510530 A | 4/2008 |
| JP | 2009500052 A | 8/2009 |
| JP | 2015536186 A | 12/2015 |
| WO | WO99/12489 A2 | 3/1999 |
| WO | WO2004/039428 A2 | 5/2004 |
| WO | WO2008/049084 A2 | 4/2008 |
| WO | WO2014/150887 A1 | 9/2014 |
| WO | WO2014/197625 A1 | 12/2014 |
| WO | WO2016/084081 A2 | 6/2016 |
| WO | WO2016/090175 A1 | 6/2016 |
| WO | WO2016/132340 A1 | 8/2016 |
| WO | WO2016/176333 A1 | 11/2016 |
| WO | WO2017/074920 A1 | 5/2017 |
| WO | WO2017/096007 A1 | 6/2017 |
| WO | WO2018/125822 A2 | 7/2018 |
| WO | WO2019/148094 A1 | 8/2019 |

OTHER PUBLICATIONS

Andren-Sandberg et al.; Thoracoscopic splanchnicectomy for chronic, severe pancreatic pain; In Seminars in Laparoscopic Surgery; 3(1); Sage CA: Thousand Oaks CA; Sage Publications; pp. 29-33; Mar. 1, 1996.

Barnes et al.; Haemodynamic responses to stimulation of the splanchnic and cardiac sympathetic nerves in the anaesthetized cat; The Journal of Physiology; 378; pp. 417-436; Sep. 1986.

Bauereisen et al.; The importance of mesenteric mechanoreceptors for the reflex innervation of resistance blood vessels capacity blood vessels in the splanchnic area; Pflugers Archiv fur die gesamte Physiologie des Menschen und der Tiere; 276; pp. 445-455; Jan. 1963.

Bradley et al.; Nerve blocks and neuroablative surgery for chronic pancreatitis; World J. Surg.; 27(11); pp. 1241-1248; Nov. 1, 2003.

Brooksby et al.; Dynamic changes in splanchnic blood flow and blood volume in dogs during activation of sympathetic nerves; Circulation Research; XXIX(3); pp. 227-238; Sep. 1971.

Brunner et al.; Carotid sinus baroreceptor control of splanchnic resistance and capacity. Am J Physiol.; 255; pp. H1305-1310; Dec. 1988.

Burkhoff et al.; Why does pulmonary venous pressure rise after on of LV dysfunction: a theoretical analysis; Am. J. Physiol.; 265(5, pt. 2); pp. H1819-1828; Nov. 1993.

Buscher et al.; Limited effect of thoracoscopic splanchnicectomy in the treatment of severe chronic pancreatitis pain: a prospective long-term analysis of 75 cases; Surgery; 143(6); pp. 715-722; Jun. 30, 2008.

Carneiro et al.; Change in liver blood flow and blood content in dogs during direct and reflex alteration of hepatic sympathetic nerve activity: Circulation Research; 40(2); pp. 150-158: Feb. 1, 1977.

Cody et al.; Captopril kinetics in chronic congestive heart failure; Clin pharmacol Ther.; 32(6); pp. 721-726; Dec. 1982.

Cuschieri et al.; Bilateral endoscopic splanchnicectomy through a posterior thoracoscopic approach; Journal of the Royal College of Surgeons of Edinburgh; 39(1); pp. 44-47; Feb. 1994.

Diedrich et al.; Segmental orthostatic fluid shifts; Clinical autonomic research; 14(3); pp. 146-147; Jun. 2004.

Edwards Lifesciences; ClearSight System (brochure; No. AR11578); 4 pgs.; © 2014.

Edwards; The glycogenolytic response to stimulation of the splanchnic nerves in adrenalectomized calves, sheep, dogs, cats and pigs; J Physiol.; 213; pp. 741-759; Mar. 1971.

Eisenberg et al.; Neurolytic celiac plexus block for treatment of cancer pain: A meta-analysis; Anesth Analg; 80(2); pp. 290-295; Feb. 1995.

Fallick et al., Sympathetically mediated changes in capacitance: Redistribution of the venous reservoir as a cause of decompensation; Circulation: Heart Failure; 4; pp. 669-675; Sep. 2011.

Ferrara et al; Hemodynamics of the splanchnic and systemic circulation after hypotonic water load-comparison between normal subjects and patients with congestive heart failure; Acta Cardioiogica; 38(2); pp. 81-88; Dec. 1982.

Fiaccadori et al.; Ultrafiltration in Heart Failure; Am Heart J.; 161(3); pp. 439-449; Mar. 2011.

Folkow et al.; The Effect of Graded Vasoconstrictor Fibre Stimulation on the Intestinal Resistance and Capacitance Vessels; Acta physiologica Scandinavica; 61; pp. 445-457; Aug. 1964.

Foss et al.; Reversal of genetic salt-sensitive hypertension by targeted sympathetic ablation; Hypertension; 61(4); pp. 806-811; Apr. 1, 2013.

Francis et al.; Clinical notes, suggestions and new instrument; JAMA; 134(1); pp. 20-21; May 3, 1947.

Fudim et al.; Role of volume redistribution in the congestion of heart failure; Journal of the American Heart Association; 6(8); e006817; 11 pages; Aug. 1, 2017.

Fujita; Splanchnic circulation following coeliac plexus block; Acta Anaesthesiol Scand.; 32(4); pp. 323-327; May 1988.

Gambro® ; Aquadex FlexFlowTM (brochure, No. L5189 Rev. B); 4 pgs.; © 2011 (August).

Garcea et al.; Percutaneous splanchnic nerve radiofrequency ablation for chronic abdominal pain; ANZ Journal of Surgery; 75(8); pp. 640-644; Aug. 1, 2005.

Giraudo et al.; Endoscopic palliative treatment of advanced pancreatic cancer: Thoracoscopic splanchnicectomy and laparoscopic gastrojejunostomy; Annals of Oncology; 10(4); pp. S278-S280: Jan. 1, 1999.

Goldblatt et al.; Studies on experimental hypertension II: The effect of resection of splanchnic nerves on experimental renal hypertension: The Journal of Experimental Medicine; 65(2): pp. 233-241: Feb. 1, 1937.

Goroszeniuk et al.; Permanent percutaneous splanchnic nerve neuromodulation for management of pain due to chronic pancreatitis: A case report; Neuromodulation; ;14(3); pp. 253-257; May-Jun. 2011.

Greenway et al.; Role of splanchnic venous system in overall cardiovascular homeostasis; In Federal Proceedings; 42(6); pp. 1678-1684; Apr. 1983.

Greenway: Blockade of reflex venous capacitance responses in liver and spleen by hexamethonium, atropine, and surgical section; Can. J. Physiol. Pharmacol.; 69(9); 1284-1287; Sep. 1991.

Griffith et al.; The vasomotor control of the liver circulation; American Journal of Physiology; 95(1); pp. 20-34; Oct. 1930.

Griffith et al.; Vasomotor Control of the Liver Circulation. Proceedings of the Society for Experimental Biology and Medicine; 27(7); pp. 673-674; Apr. 1930.

(56) References Cited

OTHER PUBLICATIONS

Herman et al.; Splenic afferents and some of their reflex responses; American Journal of Physiology-Regulatory, Integrative and Comparative Physiology; 242(3); pp. R247-R254; Mar. 1982.

Ihse et al.; Bilateral thoracoscopic splanchnicectomy: effects on pancreatic pain and function; Annals of Surgery; 230(6); pp. 785-791; Dec. 1, 1999.

Ischia et al; A new approach to the neurolytic block of the coeliac plexus: the transaortic technique; Pain; 16(4); pp. 333-341; Aug. 31, 1983.

Johnson et al.; An open randomized comparison of clinical effectiveness of protocol-driven opioid analgesia, celiac plexus block or thoracoscopic splanchnicectomy for pain management in patients with pancreatic and other abdominal malignancies; Pancreatology; 9(6); pp. 755-763; Jan. 1, 2009.

Kang et al.; Bilateral thoracoscopic splanchnicectomy with sympathectomy for managing abdominal pain in cancer patients; Am J Surg; 194(1); pp. 23-29; Jul. 2007.

Katri et al.; Thoracoscopic splanchnicectomy for pain control in irresectable pancreatic cancer; Journal of Laparoendoscopic and Advanced Surgical Techniques; 18(2); pp. 199-203; Apr. 1, 2008.

Kaufman et al.; Effect of portal hypertension on splenic blood flow, intrasplenic extravasation and systemic blood pressure; American Journal of Physiology-Regulatory. Integrative and Comparative Physiology; 284(6); pp. R1580-1585; Jun. 1, 2003.

Kimura et al.; Application of electrical impedance analysis for diagnosis of a pulmonary mass; Chest; 105(6); pp. 1679-1682; Jun. 1994.

King et al.; Splanchnic circulation is a critical neural target in angiotensin II salt hypertension in rats; Hypertension; 50(3); pp. 547-556; Sep. 2007.

Krishna et al.; Video-assisted thoracoscopic sympathectomy-splanchnicectomy for pancreatic cancer pain; Journal of Pain and Symptom Management; 22(1); pp. 610-616; Jul. 1, 2001.

Lang-Lazdunski et al.; Videothoracoscopic splanchnicectomy for intractable pain from adrenal metastasis; Ann Thorac Surg; 73(4); pp. 1290-1292; Apr. 2002.

Le Pimpec Barthes; Thoracoscopic splanchnicectomy for control of intractable pain in pancreatic cancer; The Annals of Thoracic Surgery; 65(3); pp. 810-813; Mar. 31, 1998.

Leksowski; Thoracoscopic splanchnicectomy for the relief of pain due to chronic pancreatitis; Surg Endosc.; 15(6); pp. 592-596; Jun. 2001.

Lica et al.; Thoracoscopic left splanchnicectomy—role in pain control in unresectable pancreatic cancer. Initial experience; Chirurgia; 109(3); pp. 313-317; May-Jun. 2014.

Lieberman et al.; Celiac plexus neurolysis with the modified transaortic approach; Radiology; 175(1); pp. 274-276; Apr. 1990.

Lillemoe et al; Chemical splanchnicectomy in patients with unresectable pancreatic cancer. A prospective randomized trial; Annals of Surgery; 217(5); pp. 447-457; May 1, 1993.

Lin et al.; Bilateral thoracoscopic lower sympathetic-splanchnicectomy for upper abdominal cancer pain. The European journal of surgery; Supplement 572; pp. 59-62; 1994.

Lonroth et al.; Unilateral left-side thoracoscopic sympathectomy for visceral pain control: a pilot study; The European Journal of Surgery; 163(2); pp. 97-100; Feb. 1, 1997.

Maass-Moreno et al.; Carotid baroreceptor control of liver and spleen volume in cats; Am J Physiol; 260(1 Pt 2); pp. H254-259; Jan. 1991.

Maher et al.; Thoracoscopic splanchnicectomy for chronic pancreatitis pain; Surgery; 120(4); pp. 603-610; Oct. 1996.

Myhre et al.; Monitoring of celiac plexus block in chronic pancreatitis; Pain; 38(3); pp. 269-274; Sep. 1989.

Nakazato et al; Extrinsic Innervation of the canine abdominal vena cava and the origin of cholinergic vasoconstrictor nerves; J. Physiol.; 328; pp. 191-203; Jul. 1982.

Nath et al.; Biophysics and pathology of catheter energy delivery systems; Progress in Cardiovascular Diseases; XXXVII(4); pp. 185-204; Jan./Feb. 1995.

Norman: Posterior Mediastinum; As last known Jun. 6, 2013; retrieved from the internet (https:web.archive.org/web/20130606053828/ http://www.wesnorman.com/thoraxlesson5.htm); 11 pages; on Sep. 16, 2020.

Pan et al.; Differential responses of regional sympathetic activity and blood flow to visceral afferent stimulation; Am J Physiol Regul Integr Comp Physiol.; 280(6); pp. R1781-1789; Jun. 2001.

Pietrabissa et al.; Thoracoscopic splanchnicectomy for pain relief in unresectable pancreatic cancer; Archives of Surgery; 135(3); pp. 332-335; Mar. 1, 2000.

Plancarte et al.; Management of chronic upper abdominal pain in cancer: transdiscal blockage of the splanchnic nerves; Regional Anesthesia and Pain Medicine; 35(6); pp. 500-506; Nov. 1, 2010.

Prasad et al.; Thoracoscopic splanchinicectomy as a palliative procedure for pain relief in carcinoma pancreas; Journal of Minimal Access Surgery: 5(2); pp. 37-39; (Author Manuscript); Apr. 1, 2009.

Raj; Celiac plexus/splanchnic nerve blocks; Techniques in Regional Anesthesia and Pain Management; 5(3); pp. 102-115; Jul. 2001.

Raj et al.; Radiofrequency lesioning of splanchnic nerves; Pain Practice: 2(3); pp. 242-247; Sep. 2002.

Saenz et al.; Thoracoscopic splanchicectomy for pain control in patients with unresectable carcinoma of the pancreas; Surgical Endoscopy; 14(8); pp. 717-720; Aug. 1, 2000.

Sastre et al.; Transhiatal bilateral splanchnicotomy for pain control in pancreatic cancer: basic anatomy, surgical technique, and immediate results in fifty-one cases; Surgery; 111(6); pp. 640-646; Jun. 1992.

Scott-Douglas et al.; Effects of acute volume loading and hemorrhage on intestinal vascular capacitance: a mechanism whereby capacitance modulates cardiac output; Can. J. Cardiol.; 18(5); pp. 515-522; May 5, 2002.

Shimada et al.; Clinical evaluation of transhiatal bilateral splanchnicotomy for patients with intractable supramesenteric pain; Surgery Today; 29(11); pp. 1136-1140; Nov. 1999.

Smigielski et al.; Assessment of quality of life in patients with non-operated pancreatic cancer after videothoracoscopic splanchnicectomy; Videosurgery and Other Miniinvasive Techniques; 6(3); pp. 132-137; Sep. 1, 2011.

Stefaniak et al.; A comparison of two invasive techniques in the management of intractable pain due to inoperable pancreatic cancer; European Journal of Surgical Oncology; 31 (7); pp. 768-773; Sep. 30, 2005.

Takahashi et al.; Thoracoscopic splanchnicectomy for the relief of intractable pain: Surgical Endoscopy; 10(1); pp. 65-68; Jan. 1, 1996.

Tavassoli et al.; Thoracoscopic splanchnicectomy for pain control in urresectable pancreatic cancer; Journal of Cardio-Thoracic Medicine; 1(2); pp. 53-56; Aug. 6, 2013.

Tsybenko et al.; Central nervous control of hepatic circulation; J Aut Nerv Sys; 33(3): pp. 255-266; May 1991.

Van Vliet et al.; Time course of renal responses to greater splanchnic nerve stimulation; American Journal of Physiology Regulatory, Integrative and Comparative Physiology: 260(5); pp. R894-R905; May 1991.

Verhaegh et al.; Percutaneous radiofrequency ablation of the splanchnic nerves with chronic pancreatitis: results of single and repeated procedures in 11 patients; Pain Practice; 13(8); pp. 621-626; (Author Manuscript); Nov. 1, 2013.

Wilkins et al.; The effect of splanchnic sympathectomy in hypertensive patients upon estimated hepatic blood flow in the upright as contrasted with the horizontal position; Journal of Clinical investigation; 30(3); pp. 312-317; Mar. 1951.

Worsey et al.; Thoracoscopic pancreatic denervation for pain control in irrsectable pancreatic cancer; British Journal of Surgery; 80(8); pp. 1051-1052; Aug. 1, 1993.

Wroclaw Medical Univ. (Poland); Removing a section of nerve visceral improved (press release, with machine translation), retrieved Oct. 10, 2016 from the Internet: http://www.zdrowie.abc.com /pl/ aktualnosci/wroclaw-usuniecie-fragmentu-nerwu-tzewnego-poprawilo-u-chorej-wydolnose-serca,25247 html: 5 pgs ; Sep. 23, 2016.

Yan et al.; Neurolytic celiac plexus block for pain control in unresectable pancreatic cancer; Am J Gastroenterol; 102(2); pp. 430-438; Feb. 2007.

(56) References Cited

OTHER PUBLICATIONS

Levin et al.; U.S. Appl. No. 15/017,260 entitled "Devices And Methods For Treatment Of Heart Failure By Splanchnic Nerve Ablation," filed Feb. 5, 2016.
Baghdadi et al.; Systematic review of the role of thoracoscopic splanchnicectomy in palliating the pain of patients with chronic pancreatitis: Surgical endoscopy; 22(3); pp. 580-588; Dec. 28, 2007.
Buscher et al.; Bilateral thoracoscopic splanchnicectomy for pain in patients with chronic pancreatitis impairs adrenomedullary but not noradrenergic sympathetic function; Surgical Endoscopy; 26(8); p. 2183-2188; Aug. 2012.
Chatterjee et al.; Novel interventional therapies to modulate the autonomic tone in heart failure; JACC: Heart Failure; 3(10); pp. 786-802; Oct. 2015.
Crespy et al.; Anatomical bases of the transhiatus approach to the greater splanchnic nerve; Anatomia Clinica; 6(4); pp. 247-254; Dec. 1, 1984.
Dayal et al.; Variations in the formation of thoracic splanchnic nerves; European Journal of Anatomy; vol. 18; pp. 141-151; (year of pub. sufficiently earlier than effective US filing date and any foreign priority date) 2014.
Del Rio et al.; Carotid chemoreceptor ablation improves survival in heart failure: rescuing autonomic control of cardiorespiratory function; Journal of the American College of Cardiology; 62(25); pp. 2422-2430; Dec. 24, 2013.
Gafanovich et al.; Chronic diarrhea-induced by celiac plexus block?; Journal of Clinical Gastroenterology; 26(4); pp. 300-302; Jun. 1, 1998.
Girouard et al.; Optical mapping in a new guinea pig model of ventricular tachycardia reveals mechanisms for multiple wavelengths in a single reentrant circuit; Circulation; 93(3); pp. 603-613; Feb. 1, 1996.
Loukas et al.; A review of the thoracic splanchnic nerves and celiac ganglia; Clinical Anatomy; 23(5); pp. 512-522; Jul. 2010.
Mallet-Guy et al.; Treatment of chronic pancreatitis by unilateral splanchnicectomy; Archives of Surgery; 60(2); pp. 233-241; Feb. 1, 1950.
Masuda et al.; Splanchnicectomy for pancreatic cancer pain; BioMed Research International; Jan. 1, 2014.
Naidoo et al.; Thoracic splanchnic nerves: implications for splanchnic denervation; Journal of Anatomy; 199(5); pp. 585-590; Nov. 2001.
Sadar et al.; Bilateral thoracic sympathectomy-splanchnicectomy in the treatment of intractable pain due to pancreatic carcinoma; Cleveland Clinic Quarterly; 41; pp. 185-188; (year of pub. sufficiently earlier than effective US filing date and any foreign priority date)1974.
Triposkiadis et al.; The sympathetic nervous system in heart failure: physiology, pathophysiology, and clinical implications; Journal of the American College of Cardiology; 54(19); pp. 1747-1762; Nov. 3, 2009.
Iranitalab; U.S. Appl. No. 17/152,665 entitled "Methods and devices for endovascular ablation of a splanchnic nerve," filed Jan. 19, 2021.
Levin et al.; U.S. Appl. No. 17/171,447 entitled "Devices and methods for treatment of heart failure by splanchnic nerve ablation," filed Feb. 9, 2021.
Raj et al.; The development of a technique for radiofrequency lesioning of splanchnic nerves; Current Review of Pain; 3(5); pp. 377-387; Oct. 1999.
Levin et al.; U.S. Appl. No. 17/452,305 entitled "Devices, systems, and methods for treatment of heart failure by splanchnic nerve ablation," filed Oct. 26, 2021.
Gelfand et al.; U.S. Appl. No. 17/644,998 entitled "Methods, systems and devicesfor endovascular electroporation of a greater splanchnic nerve," filed Dec. 17, 2021.
Burchell et al.; Chemohypersensitivity and autonomic modulation of venous capacitance in the pathophysiology of acute decompensated heart failure; Current Heart failure Reports; 10(2); pp. 139-146; Jan. 2013.
Puntawangkoon et al.; Reduced peripheral arterial blood flow with preserved cardiac output during submaximal bicycle exercise in elderly heart failure; Journal of Cardiovascular Magnetic Resonance; 11(1); pp. 1-11; Dec. 2009.
Piciucchi et al.; The azygos vein pathway: an overview from anatomical variations of pathological changes; Insights Imaging; 5(5); pp. 619-628; Oct. 2014.
Iranitalab et al.; U.S. Appl. No. 18/057,482 entitled "Methods and devices for endovascular ablation of a splanchnic nerve," filed Nov. 21, 2022.
Koutsouflianiotis et al.; A left-sided azygos vein in a cadaver: anatomical and surgical considerations; Cureus Journal of Medical Science; 10(5); 4 pages; May 10, 2018.

* cited by examiner

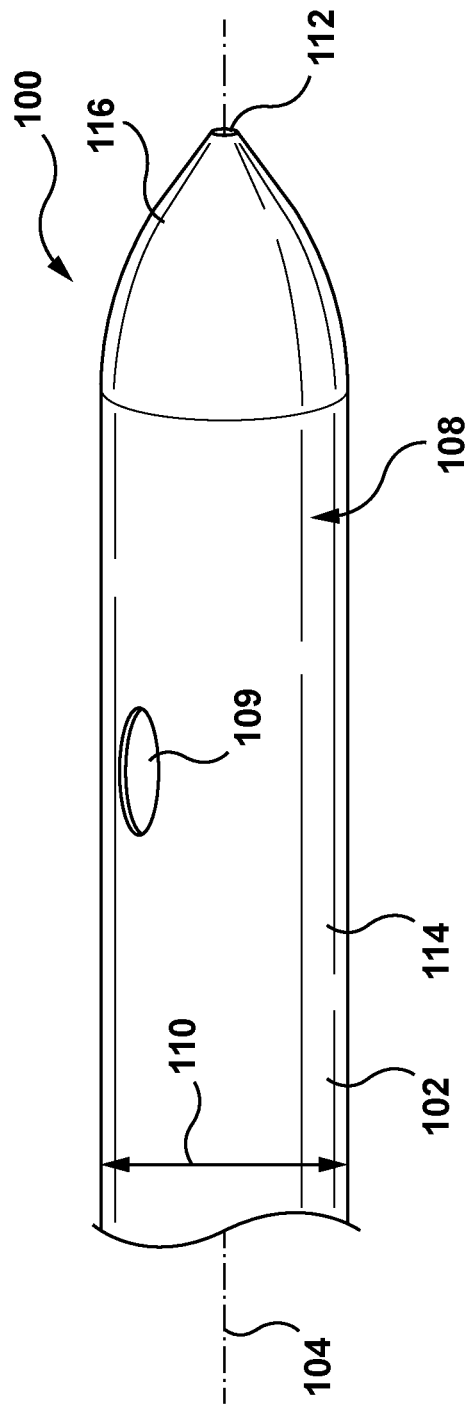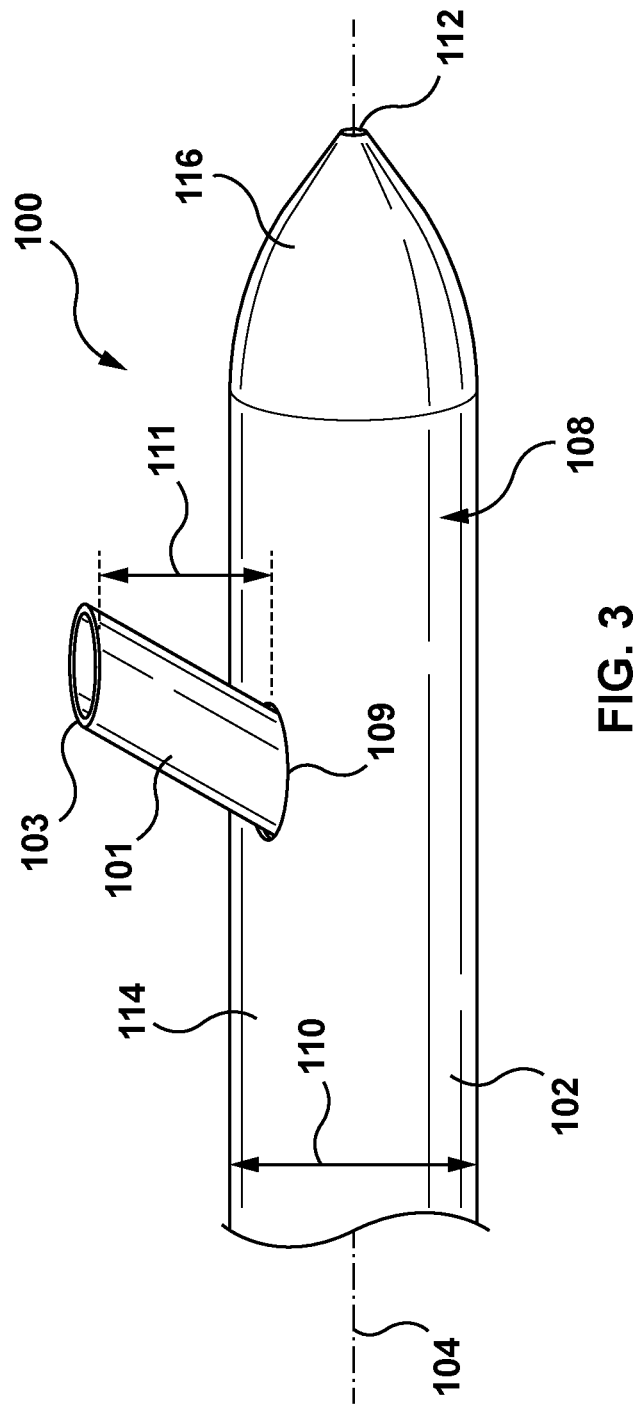

METHODS AND DEVICES FOR ENDOVASCULAR ABLATION OF A SPLANCHNIC NERVE

CROSS REFERENCE TO RELATED APPLICATIONS

This application claims priority to the following U.S. provisional applications, which are fully incorporated by reference herein for all purposes: App. No. 62/622,407, filed Jan. 26, 2018, App. No. 62/625,183, filed Feb. 1, 2018, and App. No. 62/625,195, filed Feb. 1, 2018.

INCORPORATION BY REFERENCE

All publications and patent applications mentioned in this specification are herein incorporated by reference to the same extent as if each individual publication or patent application was specifically and individually indicated to be incorporated by reference.

This document is related by subject matter to US Pub. No. 2018/0110561, PCT Pub. No. WO2018/023132, and PCT Application No. PCT/US2018/066047 (filed Dec. 17, 2018), all of which are incorporated by reference herein in their entireties for all purposes.

BACKGROUND

Heart failure (HF) is a medical condition that occurs when the heart is unable to pump sufficiently to sustain the organs of the body. Heart failure is a serious condition and affects millions of patients in the United States and around the world.

One common measure of heart health is left ventricular ejection fraction (LVEF) or ejection fraction. By definition, the volume of blood within a ventricle immediately before a contraction is known as the end-diastolic volume (EDV). Likewise, the volume of blood left in a ventricle at the end of contraction is end-systolic volume (ESV). The difference between EDV and ESV is stroke volume (SV). SV describes the volume of blood ejected from the right and left ventricles with each heartbeat. Ejection fraction (EF) is the fraction of the EDV that is ejected with each beat; that is, it is SV divided by EDV. Cardiac output (CO) is defined as the volume of blood pumped per minute by each ventricle of the heart. CO is equal to SV times the heart rate (HR).

Cardiomyopathy, in which the heart muscle becomes weakened, stretched, or exhibits other structural problems, can be further categorized into systolic and diastolic dysfunction based on ventricular ejection fraction.

While a number of drug therapies successfully target systolic dysfunction and HFrEF, for the large group of patients with diastolic dysfunction and HFpEF no promising therapies have yet been identified. The clinical course for patients with both HFrEF and HFpEF is significant for recurrent presentations of acute decompensated heart failure (ADHF) with symptoms of dyspnea, decreased exercise capacity, peripheral edema, etc. Recurrent admissions for ADHF utilize a large part of current health care resources and could continue to generate enormous costs.

While the pathophysiology of HF is becoming increasingly better understood, modern medicine has, thus far, failed to develop new therapies for chronic management of HF or recurrent ADHF episodes. Over the past few decades, strategies of ADHF management and prevention have and continue to focus on the classical paradigm that salt and fluid retention is the cause of intravascular fluid expansion and cardiac decompensation.

Thus there remains a need for improved therapies for heart failure patients that are safe and effective, and devices and systems that are adapted and configured to perform those therapies.

SUMMARY OF THE DISCLOSURE

The following first part of the summary is intended to introduce the reader to various aspects of methods for endovascular ablation of one or more thoracic splanchnic nerves or nerve roots (e.g., greater splanchnic nerves or nerve roots), but not necessarily to define or delimit any invention, or limit the disclosure.

The disclosure is related to methods of, devices for, and approaches for ablating one or more thoracic splanchnic nerves or thoracic splanchnic nerve roots. The ablations can be performed to treat at least one of hypertension and heart failure, but the general methods may also be used for other treatments as well. For example, the methods herein can be used in the treatment of pain, or even to generally benefit the subject to reducing the amount of blood that is expelled from the splanchnic bed into the central thoracic veins.

The treatments herein may be accomplished by increasing splanchnic capacitance. The therapies generally include ablating one or more of a patient's preganglionic thoracic splanchnic nerves or thoracic splanchnic nerve branches to increase splanchnic capacitance, and thereby treat at least one of hypertension and heart failure.

Methods herein describe ablating thoracic splanchnic nerves, such as a greater splanchnic nerve or greater splanchnic nerve roots. While methods herein may provide specific examples of targeting greater splanchnic nerve or greater splanchnic nerve roots, it may be possible to alternatively, or in addition to, ablate other thoracic splanchnic nerves (e.g., lesser, least) to perform one or more treatments herein.

One aspect of the disclosure is a method of ablating tissue by positioning a medical device intravascularly in the vicinity of target tissue and using the medical device to ablate tissue and create a lesion. One aspect of the disclosure is a method of ablating tissue by positioning a medical device intravascularly into one or more target vessels and using the medical device to ablate tissue and create a lesion. The methods herein can thus be described as methods that position a medical device near target tissue to be ablated and/or methods that position a medical device in one or more vessels, where the target tissue is relatively near to the target regions within the one or more vessels. Any of the method steps herein (including, for example without limitation, in the claims or the Description section) can be incorporated into any other method of use herein unless specifically indicated to the contrary herein.

One aspect of the disclosure is a method of ablating a greater splanchnic nerve or a greater splanchnic nerve root to increase splanchnic venous blood capacitance, the method including advancing a medical device into a first vessel, advancing the medical device into a second vessel, and delivering ablation energy from the medical device to create a lesion in tissue surrounding the first vessel.

In some embodiments the first vessel is an azygous vein and the second vessel is an intercostal vein.

In some embodiments an intercostal vein is one of the three lowest intercostal veins.

In some embodiments an intercostal vein is a T9, T10, or T11 intercostal vein.

The methods can include positioning a distal end of an ablation element in the second vessel and no more than 30 mm (e.g., 20 mm, 15 mm, 12 mm) from a junction between the first vessel and the second vessel when delivering the energy.

The methods can include a proximal portion of an ablation being disposed in the second vessel when delivering energy.

The methods can include delivering fluid from a fluid lumen of the medical device into a membrane, wherein the membrane at least partially defines a fluid chamber. Delivering the fluid can inflate the membrane and cause it to change configuration to an expanded configuration or state. Expanding the membrane may cause the membrane to have an outer diameter larger than a size of the vessel.

The methods can include positioning the ablation element into contact with a wall of the second vessel, optionally along the entire length of the ablation element, or at least along an active ablation length of the ablation element.

The methods can include expanding the membrane so that it has an outer diameter from 2 mm to 4 mm.

Creating the lesion can include creating a lesion that has a depth of at least 5 mm around the ablation element.

Creating the lesion can include ablating a portion of a thoracic splanchnic nerve or a thoracic splanchnic nerve root, e.g., a greater splanchnic nerve or GSN root.

The lesion may be a continuous lesion. The lesion may have a length from 5 mm to 20 mm, such as 10 mm to 20 mm, such as 12 mm to 18 mm.

The lesion may be a circumferential lesion all the way around the second vessel. The lesion may be less than circumferential all the way around the second vessel, such as 225 degrees or less, 180 degrees or less, 135 degrees or less, 90 degrees or less, 45 degrees or less.

The methods can include positioning an entire ablation element in the second vessel, while the method can also include positioning less than the entire length of the ablation element in the second vessel.

The methods can include performing an ablation process in more than one target vessel, such as an intercostal vein or an azygous vein. The methods of ablation herein can also be performed in the second vessel.

The methods can include performing an ablation confirmation test, such as any of the tests herein. If desired or needed, an ablation element may be repositioned into a second target vessel, which may be an azygous vein or a different intercostal vein.

The methods can create a continuous lesion that has a length from 1 mm to 20 mm, such as from 5 mm to 20 mm, such as from 10 mm to 20 mm.

The methods can also include, prior to, during, and/or subsequent to delivering the ablation energy, delivering stimulation energy to at least one of first and second stimulation electrodes carried by the medical device. Delivering stimulation energy may help determine if the ablation element is in a target location within the intercostal vein, and/or if an ablation procedure was effective.

One aspect of the disclosure is a method of ablating a thoracic splanchnic nerve or a thoracic splanchnic nerve root to treat at least one of hypertension and heart failure, comprising: advancing an elongate medical device into an intercostal vein, the elongate medical device comprising an ablation member disposed at a distal region of the medical device; expanding the ablation member within the intercostal vein; activating the ablation member to create an electromagnetic field in tissue around the intercostal vein. The method can include heating tissue surrounding the intercostal vein to a temperature of up to 99 degrees C. and ablating a thoracic splanchnic nerve or a thoracic splanchnic nerve root.

One aspect of the disclosure is a method of transvascular ablation of target tissue, the method include delivering an ablation catheter through a patient's vasculature to a first vessel, the ablation catheter comprising at least one energy delivery element; advancing the at least one energy delivery element into a second vessel, the second vessel directly connecting to the first vessel; and delivering ablation energy from the at least one energy delivery element to the target tissue. The ablation catheter can include at least one RF electrode that has a diameter that is within 1 mm of the diameter of the second vessel (e.g., within 1 mm less than or greater than the diameter of the second vessel).

The energy delivery element can include an RF electrode, microwave antenna, ultrasound transducer, cryogenic applicator, and/or thermal element. The step of advancing the at least one energy delivery element can include advancing a distal end of the energy delivery element no more than 30 mm, such as no more than 20 mm, into the second vessel from the first vessel. In an embodiment the at least one energy delivery element has the same diameter during the step of advancing and the step of delivering ablation energy. In some embodiments the at least one energy delivery element has a greater diameter during the step of delivering ablation energy than the advancing step.

Any of the other method steps herein that are described in the context of other methods can be performed with this exemplary method.

Another aspect of the disclosure is a method of transvascular ablation of a greater splanchnic nerve comprising the following steps: delivering an ablation catheter comprising a distal region, an ablation element on the distal region, and two nerve stimulation electrodes positioned distal and proximal to the ablation element to an intercostal vein; positioning the ablation element in a target region within the intercostal vein; measuring a first physiological condition without delivering energy from the ablation catheter to establish a baseline response; delivering a nerve stimulation signal in bipolar mode to the two nerve stimulation electrodes; measuring a second physiological condition during the nerve stimulation signal delivery; if the second physiological condition shows an increased sympathetic response compared to the first physiological condition, then delivering ablation energy from the ablation element; following or during ablation energy delivery, delivering a second nerve stimulation signal and measuring a third physiological condition; if the third physiological condition shows a decreased sympathetic response compared to the first physiological condition, removing the catheter from the patient; adjusting the position of the ablation element within the intercostal vein or moving it to a different intercostal vein and repeating the steps between delivering the nerve stimulation signal to delivering ablation energy if the second physiological condition does not show an increased sympathetic response compared to the first physiological condition; moving the ablation element to an adjacent intercostal vein and repeating the steps between delivering the nerve stimulation signal to delivering ablation energy if the third physiological condition does not show a decreased sympathetic response compared to the first physiological condition.

A physiological condition may be, for example, venous compliance and the measuring may comprise a leg raise test, a hand-grip test, and/or a test that activates SNS.

Any nerve stimulation signals herein may comprise, for example, 50 Hz and 1 V

One aspect of the disclosure is a method that includes delivering an ablation catheter comprising an energy delivery element (or member) through a venous system of the patient, positioning the energy delivery element at least partially (optionally completely) inside a vein selected from T9, T10 and T11 intercostal veins, delivering ablation energy from the energy delivery element to create a continuous lesion having a depth of at least 5 mm and a length from to 20 mm. The continuous lesion and its parameters can be formed by selecting or choosing certain energy delivery parameters that will create the lesion. In some embodiments, the lesion can extend from an ostium of an azygos vein to up to 20 mm along the intercostal vein.

Any of the other method steps herein that are described in the context of other methods can be performed with this exemplary method.

In some alternative methods herein, a plurality of ablations (i.e., from ablation energy on to energy ablation off) can be performed within a single target vessel (e.g., an intercostal vein) to create a total lesion made from two or more lesions made from the plurality of ablations. The total lesion made from the plurality of lesions can have any of characteristics of the other lesions herein. For example, the total lesion can be continuous (made by the connection of a plurality of lesions created during different ablations), can be up to 20 mm long, can be circumferential (or not), etc. After a first ablation, the ablation device can be moved within the same vessel and create a second lesion, which may or may not overlap with a first lesion. This can be repeated as many times as desired. Any of the stimulation or testing steps herein can be performed before, during, or after any ablation step, even if a plurality of ablations are performed in a single vessel.

One aspect of the disclosure is an ablation device (e.g., an ablation catheter) adapted for endovascular ablation of a patient's greater splanchnic nerve or a greater splanchnic nerve root. The device may include a flexible shaft having a distal section and a proximal section, at least one ablation element carried by the distal section (directly or indirectly), wherein the at least one ablation element has an active ablation length from 1 mm to 20 mm (optionally from 5 mm to 20 mm) and an outer diameter from 2 mm to 4 mm. The active ablation length may be from 10 mm to 20 mm, e.g., 12 mm to 18 mm.

One aspect of the disclosure is an ablation device for endovascular ablation of a patient's greater splanchnic nerve or a greater splanchnic nerve root, including a flexible shaft having a distal section and a proximal section; a fluid lumen extending through at least a portion of the flexible shaft; and at least one ablation element disposed at the distal section, the at least one ablation element comprising a membrane with an active ablation length from 1 mm to 20 mm (e.g., from 5 mm to 20 mm) and an outer diameter from 2 mm to 4 mm, the membrane defining an interior volume in fluid communication with the fluid lumen.

With any of the ablation devices herein, the ablation element can be adapted and configured to create a circumferential lesion around a blood vessel in which it is placed.

With any of the ablation devices herein, the ablation element can be adapted and configured to create a lesion less than circumferential around a blood vessel in which it is placed.

With any of the ablation devices herein, an active ablation length of the at least one ablation element can be from 10 mm to 20 mm, such as from 12 mm to 18 mm.

With any of the ablation devices herein, a distal section of a flexible shaft can be adapted and configured to bend at a bend angle of at least 90 degrees and with a bend radius of between 4 mm and 15 mm.

With any of the ablation devices herein, the at least one ablation element can be adapted and configured to have a delivery configuration with a length from 5 mm to 20 mm and an outer diameter from 1.5 mm to 2.5 mm.

With any of the ablation devices herein, the device can further include a proximal stimulation electrode positioned proximal to an ablation element, and a distal stimulation electrode positioned distal to an ablation element, optionally wherein each of the proximal stimulation electrode and the distal stimulation electrode are no more than 5 mm from the ablation element.

With any of the ablation devices herein, the device can further include a proximal stimulation electrode positioned proximal to an ablation element, and a distal stimulation electrode positioned distal to an ablation element, wherein the proximal stimulation electrode and the distal stimulation electrode can be separated by a distance of no more than 25 mm.

With any of the ablation devices herein, an active ablation length may be between 12 and 18 mm.

With any of the ablation devices herein, a distal section of said flexible shaft may be configured to bend according to a bend angle of at least 90 degrees and a bend radius of between 4 mm and 15 mm.

With any of the ablation devices herein, the device may further include at least one temperature sensor, optionally positioned inside an ablation element. The at least one ablation element and the at least one temperature sensor may be connectable to an ablation energy source.

With any of the ablation devices herein, one or more nerve stimulation electrodes may be 1.5 mm+/−0.5 mm long.

With any of the ablation devices herein, the device may further comprise a temperature sensor exterior to the ablation element, which can include being carried by a surface of an ablation element.

With any of the ablation devices herein, an ablation element can be configured to emit ablative energy from a segment of the circumference of the distal region. For example, the segment may be a percentage of the circumference selected from a list of 50%, 40%, 30%, or 25% of the circumference. The segment can also be described as an angle, such as less than 225 degrees, 180 degrees or less, 135 degrees or less, 90 degrees or less, or 45 degrees or less. The remainder of the circumference not adapted to emit ablative energy may optionally comprise an electrically resistive material (e.g., disposed on or within a membrane layer). Optionally, the segment can be defined by a fenestration in a sheath. The distal region of the device may further comprise a radiopaque marker configured to indicate radial orientation. For example, the radiopaque marker may be radially aligned with the segment adapted to emit ablative energy.

With any of the ablation devices herein, a distal tip may be tapered to facilitate delivery from a first vessel to a second vessel having a smaller lumen diameter.

With any of the ablation devices herein, the device can further comprise a distal tubular extension having greater flexibility than an elongate tubular shaft, and wherein a guidewire lumen optionally extends through the distal tubular extension.

With any of the ablation devices herein, the active ablation length of the ablation element is considered the length of the ablation element that is in contact with, or configured to be in contact with, tissue during an ablation step.

The following second part of the summary is intended to introduce the reader to various aspects of devices for endovascular vein puncture, but not to define or delimit any invention.

According to a 1st aspect of a device for endovascular vein puncture, the device includes an elongate catheter extending along a longitudinal catheter axis and having a catheter proximal portion and a catheter distal portion. The device further includes a needle guide having a needle guide distal end.

In a 2nd aspect according to the 1st aspect the needle guide has a blunt needle guide distal end.

In a 3rd aspect according to any one of the preceding aspects, the needle guide is deployable from the catheter from a needle guide storage position to a needle guide working position. In the needle guide working position, the needle guide distal end is radially spaced from the catheter, and in the needle guide storage position, the needle guide distal end is withdrawn towards the catheter relative to the needle guide working position.

In a 4th aspect according to any one of the preceding aspects the device further includes a needle having a sharp puncturing end. The needle is deployable from within the needle guide from a needle storage position to a puncturing position. In the needle storage position, the puncturing end is shy of the needle guide distal end, and in the puncturing position, the puncturing end extends proud of the needle guide distal end.

In a 5th aspect according the 3rd aspect in combination with any one of the other preceding aspects, the catheter has a catheter outer diameter. In other words, the cross section of the catheter may present an outer perimeter of substantially circular shape having said outer diameter.

In a 6th aspect according to the preceding aspect, in the puncturing position, the puncturing end is spaced from the needle guide distal end by a needle deployed distance that is less than the catheter outer diameter.

In a 7th aspect according to the preceding aspect the needle deployed distance can be less than 2 mm, or less than 1 mm.

In an 8th aspect according to any one of the preceding three aspects, in the needle guide working position, the needle guide distal end is spaced from the catheter in the radial direction by a needle guide deployed distance that is less than the catheter outer diameter.

In a 9th aspect according to the preceding aspect, the needle guide deployed distance can be between about 0.5 mm and 6 mm, or between about 0.5 mm and about 3 mm, or between about 2 mm and about 6 mm.

In a 10th aspect according to the 3rd aspect in combination with any one of the other preceding aspects, the catheter has a circumferential outer surface and a first side port in the circumferential outer surface, and the needle guide is deployable from the first side port.

In an 11th aspect according to the 4th aspect in combination with any one of the other preceding aspects, the device further includes a delivery device deployable from within the needle from a delivery device storage position to a delivery device treatment position.

In a 12th aspect according to the preceding aspect, the delivery device can be at least one of a fluid delivery device, a thermal energy delivery device, a radiofrequency energy delivery device, a cryogenic energy delivery device, and an electrical energy delivery device.

In a 13th aspect according to any one of the preceding two aspects, the delivery device can have a blunt delivery device distal end.

In a 14th aspect according to any one of the preceding three aspects, in the delivery device treatment position, the delivery device distal end can extend proud of the puncturing end by a delivery distance that is greater than the puncturing distance.

In a 15th aspect according to the preceding aspect, the delivery distance can be up to 15 mm, or between about 3 mm and about 7 mm, or between about 4 mm and about 6 mm.

In a 16th aspect according to any one of the preceding aspects, the catheter includes a guidewire lumen extending therethrough, along the catheter axis, and the catheter distal portion has a guidewire exit port.

In a 17th aspect according to the preceding aspect, the catheter includes a distal end surface and a circumferential outer surface, and the guidewire exit port is a notch that is open at and between the distal end surface and the circumferential surface.

In a 18th aspect according to the 3rd and the 17th aspects, the needle guide is deployable from the catheter at a first circumferential position on the catheter, and the notch is open at the circumferential surface at a notch circumferential position that is within 30 degrees of the first circumferential position. Optionally, the notch circumferential position can be aligned with the first circumferential position.

In a 19th aspect according to any one of the preceding aspects from the 3rd to the 18th, the device further includes a second needle guide deployable from the catheter, and a second needle deployable from within the second needle guide.

In a 20th aspect according to the preceding aspect, the needle guide is deployable from the catheter at a first longitudinal position on the catheter, and the second needle guide is deployable from the catheter at a second longitudinal position on the catheter.

In a 21st aspect according to the preceding aspect, the second longitudinal position is spaced from the first longitudinal position.

In a 22nd aspect according to any one of the preceding three aspects, the needle guide is deployable from the catheter at a first circumferential position on the catheter, and the second needle guide is deployable from the catheter at a second circumferential position on the catheter. Optionally, the second circumferential position can be aligned with the first circumferential position.

In 23rd aspect according to any one of the preceding aspects, the device includes at least a first radiopaque marker. The first radiopaque marker can be on the catheter, the needle guide, or the needle.

In a 24th aspect according to the preceding aspect, the first radiopaque marker is on the catheter and is configured to indicate a rotational orientation of the catheter.

In a 25th aspect according to any one of the preceding two aspects, the first radiopaque marker is made from a radiopaque material.

In a 26th aspect according to any one of the preceding three aspects, the first radiopaque marker is asymmetric in shape, optionally the first radiopaque marker is N-shaped.

In a 27th aspect according to any one of the preceding four aspects, the device further includes an additional radiopaque marker on the catheter and configured to visually indicate when the rotational position of the catheter is within a set tolerance.

In a 28th aspect according to the preceding aspect, the additional radiopaque marker includes two lines the center of which is circumferentially spaced from the first radiopaque marker by about 180 degrees, so that the first radiopaque marker appears between the lines of the additional radiopaque marker when the orientation is within the set tolerance.

In a 29th aspect according to any one of aspects from the 3rd to the 28th, in the needle guide working position, the needle guide is either straight or curved and is inclined with respect to the catheter axis.

In a 30th aspect according to any one of the preceding aspects from the 3rd to the 29th, the device comprises a controller configured for:

causing deployment of the needle guide from the needle guide storage position to the needle guide working position;

causing deployment of the needle from the needle storage position to a puncturing position.

In a 31st aspect according to the preceding aspect, in combination with any one of aspects from the 11th to the 15th, wherein the controller is further configured to cause deployment of the delivery device from the delivery device storage position to the delivery device treatment position.

In a 32nd aspect according to any one of the preceding two aspects, the controller is be an analog or a digital circuit or a combination thereof; the controller is connected to appropriate actuators (such as electric motors, pneumatic or hydraulic actuators or other type of actuators or motors) configured to cause deployment of the above mentioned deployable components upon command from the controller.

In a 33rd aspect according to any one of aspects from the 11th to the 15th, the delivery device is a cryogenic energy delivery device including a first lumen for delivery of a cryogenic fluid from a source to the distal end of the cryogenic energy delivery device, and a second lumen for return of the cryogenic fluid to the source.

In a 34th aspect according to the preceding aspect, the source of cryogenic fluid includes a fluid reservoir, a supply valve between the fluid reservoir and the first lumen, a pressure release valve at the exit of the second lumen for venting the returned cryogenic fluid to atmosphere, and a controller or said controller configured for controlling the supply valve and the pressure release valve.

In a 35th aspect according to the preceding aspect, the or a controller is in communication with a temperature sensor at the distal end of the delivery device and is configured to control supply of the cryogenic fluid in response to temperature sensed by the temperature sensor.

In a 36th aspect according to any one of the preceding aspects, the device is used to ablate a thoracic splanchnic nerve, a thoracic splanchnic nerve root, or a greater splanchnic nerve.

The following third part of the summary is intended to introduce the reader to various aspects relating methods of endovascular vein puncture, but not to define or delimit any invention. Optionally the methods described in this third part of the summary may use the devices according to any one of the preceding aspects.

According to some aspects, a method for endovascular puncture and treatment includes a. advancing a catheter distal portion through a venous system of a patient to a target location within a vein; b. deploying a needle guide from the catheter in a direction that is transverse to a longitudinal axis of the catheter; c. contacting a vein wall with a blunt distal end of the needle guide and continuing to deploy the needle guide to force the blunt distal end against the vein wall; d. deploying a needle from the distal end of the needle guide to puncture the vein wall with a sharp puncturing end of the needle; and e. delivering a treatment to a region exterior to the vein via the sharp puncturing end.

In some examples, the catheter has a catheter outer diameter, and step b. includes deploying the needle guide to a deployed distance that is less than the catheter outer diameter. The deployed distance can be between 0.5 mm and 6 mm, or between 0.5 mm and 3 mm, or between 2 mm and 6 mm.

In some examples, the catheter has a catheter outer diameter, and step d. includes deploying the needle to a puncturing distance that is less than the catheter outer diameter. The puncturing distance can be less than 2 mm, or less than 1 mm.

In some examples the method includes, prior to step e., delivering a nerve stimulation test pulse via the blunt distal end or the sharp puncturing end.

In some examples step e. includes deploying a delivery device from the puncturing end and using the delivery device to deliver the treatment. Step e. can include deploying the delivery device by a delivery distance that is greater than the puncturing distance. The delivery distance can be up to 15 mm, or between 3 mm and 7 mm, or between 4 mm and 6 mm.

In some examples, step e. includes ablating a nerve.

In some examples, step e. includes delivering at least one of a fluid, a thermal energy treatment, a cryogenic energy treatment, and a radiofrequency energy treatment.

In some examples, the target location is within an azygos vein or an intercostal vein. The target location can be within a T9, T10, or T11 intercostal vein. The target location can be within an azygos vein between a T11 and T9 intercostal vein.

In some examples, step e. includes delivering a treatment to a thoracic splanchnic nerve or a thoracic splanchnic nerve root.

In some examples, step e. includes delivering a treatment to a greater splanchnic nerve.

In some examples, step e. includes delivering a treatment for heart failure.

In some examples, the method includes coordinating step e. with the patient's breathing to avoid damaging a lung of the patient with the treatment. The method can include monitoring a proximity of the needle to the patient's lung.

In some examples, step a. includes advancing the catheter over a guidewire. The target location can be in an azygos vein, and the guidewire can extend beyond the azygos vein into an intercostal vein. The method can include, prior to step b., orienting the catheter at a target orientation by rotating the catheter until the guidewire is positioned in an orienting notch of the catheter distal portion. Step b. can include deploying the needle guide from a side port in a circumferential outer surface of the catheter. The notch can be at a notch circumferential position, and the side port can be at a first circumferential position that is within 30 degrees, or within 20 degrees, or within 10 degrees of the notch circumferential position.

In some examples, the method includes, after step a., deploying a second needle guide from the catheter in a second direction transverse to the longitudinal axis of the catheter, contacting the vein wall with a second blunt distal end of the second needle guide and continuing to deploy the second needle guide force the second blunt distal end against the vein wall, deploying a second needle from the second distal end of the second needle guide to puncture the vein wall with a second puncturing end of the second needle, and delivering a second treatment via the second puncturing end. The needle guide can be deployed from a first side port in the catheter distal portion, the second needle guide can be deployed from a second side port in the catheter distal portion, and the first side port and second side port can be longitudinally spaced apart. The first side port and second side port can be longitudinally spaced apart by between 3 cm and 5 cm. The first side port and second side port can be circumferentially aligned.

In some examples, step c. includes continuing to deploy the needle guide to force the catheter away from the vein wall and abut an opposing vein wall.

One aspect of the disclosure is an ablation method that includes intravascularly puncturing at least one of an intercostal vein and an azygous vein with a medical ablation device; and ablating a thoracic splanchnic nerve or a thoracic splanchnic nerve root using the medical ablation device. The medical device can be any of the medical devices described herein.

One aspect of the disclosure is an intravascular medical device configured to be intravascularly advanced into at least one of an azygous vein and an intercostal vein, the medical device including a puncturing element adapted to be deployed from an outer shaft of the intravascular medical device to puncture at least one of the azygous vein and an intercostal vein, such as any of the relevant medical devices herein.

The following fourth part of the summary is intended to introduce the reader to various aspects relating transvascular nerve ablation embodiments, but not to define or delimit any invention. Optionally the methods described in this fourth part of the summary may use the devices according to any one of the preceding or following aspects.

One aspect is an ablation catheter configured for intravascular nerve ablation, in particular for intravascular splanchnic nerve ablation, comprising: an elongated shaft, an ablation assembly carried by a portion of the elongated shaft, wherein the ablation assembly is configured to form either a circumferential ablation pattern having at least, for example, 12 mm length or a directional ablation pattern having at least, for example, 12 mm length.

The ablation assembly may be configured to form either a circumferential ablation pattern having a length between 12 and 30 mm, optionally between 12 and 20 mm, or a directional ablation pattern having a length between 12 and 30 mm, optionally between 12 to 20 mm.

The ablation assembly may be carried by a distal straight portion of the elongated shaft.

The ablation assembly may further comprise an expandable member carried by the elongate shaft and having an unexpanded state and an expanded state, wherein the ablation assembly is mounted to the expandable member.

The catheter can be configured for insertion in a human arterial vein.

The expandable member, in the unexpanded state, can be configured for insertion in an intercostal vein of a human patient and, in the expanded state, can be configured for abutting against a vessel wall of said intercostal vein.

The expandable member, in the expanded state, can comprises a circumferential treatment zone configured to contact a vessel wall and have a length in a range of 12 to 30 mm, optionally of 12 to 20 mm, extending along a longitudinal axis of the catheter, the circumferential treatment zone.

The expandable member can have, in the unexpanded state, a diameter in a range of about 1 mm to 2.5 mm and a circumference in a range of about 3.14 mm to 7.85 mm.

The expandable member can have, in the expanded state, a diameter in a range of about 3 mm to 5 mm and a circumference in a range of about 9.4 mm to 15.7 mm.

The ablation assembly and the expandable member can be configured such that, with the expandable member in the expanded state, the ablation assembly forms a circumferential ablation pattern of at least 12 mm length, preferably of a length between 12 and 30 mm.

The expandable member can comprise a deployable balloon attached to the distal portion of the elongated shaft and optionally made of compliant material or non-compliant material that flexibly folds to contract.

The elongated shaft can comprise a flexible neck located within 10 mm proximal to the expandable member or within 10 mm proximal to the ablation assembly. The flexible neck can be capable of bending according to a minimum curvature radius of 4 mm to allow orientation of a distal portion of the elongated shaft and facilitate insertion of the same in an intercostal vein's natural orientation. The flexible neck can be be made of a softer durometer polymer, optionally Pebax, compared to the material used for the portion of the elongated shaft proximal to the flexible neck. A wire coil can be embedded in the material of the flexible neck.

The ablation assembly can comprise a plurality of electrode pad assemblies mounted on an external surface of the expandable member and configured, when the catheter is inserted in a patient's blood vessel, to come into direct contact with a blood vessel wall. Each electrode pad assembly can include a plurality of electrodes in the form of electrode pads, the electrode pads being electrically interconnected by an electrical trace, optionally wherein the electrode pads and the traces of a same electrode pad assembly are formed by a common electrically conductive supporting substrate. The electrode pads and electrical traces of a same electrode pad assembly can be aligned substantially parallel to the longitudinal axis of the catheter. The electrode pad assemblies can be mounted to the expandable member defining a plurality of electrode pads positioned around the expandable member forming a circumferential ablation pattern that is up to 20 mm long, optionally wherein the circumferential ablation pattern has a length comprised between 12 and 18 mm. Each electrode pad can be circumferentially separated by a distance of less than 5 mm, optionally less than 2.5 mm, from an angularly adjacent electrode pad. Each electrode pad can extend around the expandable member along an arc length in a range of 3 mm to 3.5 mm. Each electrode pad can have a length, measured parallel to the catheter longitudinal axis, of about 3 to 5 mm. Each electrode pad assembly can develop substantially rectilinearly along the catheter and comprises a row of electrical pads separated by respective electrical traces.

The catheter can include a plurality of electrode pad assemblies, each arranged with multiple electrode pads, the plurality of electrode pad assemblies forming rows of electrode pads, optionally at least four rows of electrode pads connected together by electrical traces. The rows of electrode pads can be evenly spaced around the circumference of the expandable member. The electrode pads on one row can be longitudinally offset from the electrode pads of adjacent rows. A space between adjacent electrode pads when the expandable member in its unexpanded state can be smaller than the space between adjacent electrode pads when the expandable member in its expanded state. Each electrode pad, when the expandable member is expanded, can be circumferentially separated from an adjacent electrode pad by a distance comprised between 0 and 1 mm. Adjacent rows of electrode pads can interlock with one another when the expandable member in its unexpanded state. When the expandable member is in its expanded state, each electrode pad can be circumferentially separated from an adjacent electrode pad by a distance comprised between about 2 mm and 5 mm.

Electrical traces that connect two consecutive electrode pads can comprise a narrow electrically conductive strip presenting width, measured circumferentially around the expandable member, significantly smaller than the arc length of the electrode pads, optionally wherein the width of each electrical trace is smaller than 0.5 mm.

Electrode pad assemblies can be configured to position electrode pads only on one side of the expandable member, optionally covering between 25% and 50% of the expandable member circumference, to generate a directional ablation pattern that is all toward the same side and of a length of a target ablation zone.

The ablation assembly can comprise a plurality of electrodes in the form of axially spaced tubular electrodes mounted on the elongated shaft. Tubular electrodes can have an external diameter in the range of 2 to 3 mm. Tubular electrodes can be consecutively mounted on the elongated shaft and have spacing between two consecutive tubular electrodes in the range of 2 to 4 mm. Each of the tubular electrodes can have a length in the 1 to 4 mm range. The catheter can include a plurality of tubular electrodes positioned along a straight section of the elongated shaft. A plurality of tubular electrodes can be positioned along a straight section of the elongated shaft and can span a distance of comprised between 12 and 20 mm. The elongated shaft can have a loop shaped section that is proximal to the straight section. The loop shaped section can comprises a plurality of tubular electrodes. The tubular electrodes or sections of shaft between the tubular electrodes can include irrigation ports configured for delivering fluid and connectable to a fluid source.

The ablation assembly can comprise at least one straight electrode parallel to the axis of the expandable member having length in a range of 12 to 20 mm. The straight electrode can cover a segment of at least 25% of the expandable member circumference. The catheter can comprise a plurality of straight electrodes positioned around the expandable member for circumferential ablation. The catheter may include exclusively one single straight electrode that covers a segment in the range between 25% and 50% of the expandable member circumference for directional ablation. Each straight electrode can be in the form of an electrode strip. Each straight electrode can contain one or more irrigation ports configured to be connected to a source of fluid.

The catheter can comprise a plurality of ultrasound transducers positioned inside the expandable member. Ultrasound transducers can be carried by a support shaft centered in the expandable member. Transducers can be placed serially spanning a length that is in a range of 12 to 20 mm to generate an ablation of a similar length. Struts or protrusions can be positioned between the transducers and the expandable member. Struts can comprise polymer strands elastically pre-shaped to radially expand away from the transducers. The transducers, optionally at least 4 mm long, are spaced apart with flexible gaps between them. The ultrasound transducers can be cylindrical for producing circumferential ablation around a target vessel. The ultrasound transducers can be flat or hemicylindrical to produce an ablation that is a partial segment of the circumference of a target vessel.

The ablation assembly can comprise a plurality of electrodes and wherein the expandable member can comprise a basket of elastic struts, optionally including 3 or more rows of struts, each strut having at least one electrode mounted to it. The basket can have a contracted delivery state with a diameter of below 2.00 mm, optionally of about 1.7 mm. The basket can have an expanded ablation state having a diameter in a range of about 2.5 mm to 4 mm. The catheter can comprise a non-occluding, radially expandable, tubular membrane associated to the struts, with the electrodes on the outer surface of the tubular membrane. The tubular membrane can be an electrically insulating material. The tubular membrane can be connected to, and optionally positioned over, the struts. The catheter can also include a coolant delivery port configured for injecting a coolant in a volume externally delimited by the tubular membrane to allow cooling of the electrodes with convection. The coolant delivery port can be at the distal end of the basket. The struts can comprise narrowed sections between mounted electrodes that have greater flexibility than the rest of the struts to facilitate bending. The basket and position of the electrodes can be configured to form an ablation pattern that is in a range of 12 to 20 mm long, optionally 15 mm long. The basket and position of the electrodes can be configured to generate to create a circumferential ablation pattern substantially along the full length of basket. The electrodes can be mounted only on one or two struts of the basket to ablate only a circumferential segment of the vessel for directional ablation. The catheter can also include a radiopaque marker that identifies a radial direction of the basket positioned on the catheter's distal region, optionally on the struts. Each of the struts can have a cross section with a respective maximum width and maximum thickness and wherein each of the electrodes has a cross section with a respective maximum width and maximum thickness, wherein the maximum thickness of the electrodes is bigger than the maximum thickness of the struts and wherein the maximum with of the electrodes is bigger than the maximum width of the struts. Each of the struts can have a cross section with a width of about 0.5 mm and thickness of about 0.13 mm. Each of the electrodes can have a cross section with a width of about 1 mm and a maximum thickness of about 0.33 mm tapered to narrower thickness at the edges of about 0.25 mm.

A power source can be connected to the ablation assembly, and a control unit can control the power source and be configured to command the power source to deliver ablation energy, in particular RF ablation energy, to the ablation assembly. The control unit can be configured to control the power source such that a larger amount of ablation power, optionally RF energy, is delivered to proximal electrode(s) than the rest of the electrode(s) to compensate for the blood flow cooling. The control unit can be configured to control the power source such that a longer duration of ablation power, optionally RF energy, is delivered to proximal electrode(s) than to the rest of the electrode(s) to compensate for the blood flow cooling. The control unit can be configured to control the power source to deliver RF ablation energy in at least one of unipolar mode sequentially, unipolar mode simultaneously, and bipolar mode. The control unit can be configured to control the power source to deliver RF ablation energy with a pulsing waveform. The control unit can be configured to control the power source and drive bipolar energy, in particular bipolar RF ablation energy, between pair of electrodes, in particular between pair of electrode pads of different electrode pad assemblies. A coolant source can be connected or connectable to a coolant injection port of the catheter, which can be in fluid communication with an inside of the expandable member. A control unit can also control the coolant source and can be configured to command the coolant source to inject coolant fluid through said coolant injection port into the expandable member. The catheter can also include a coolant exit port that is either connected to an exit lumen extending within the catheter elongated shaft or directly communicating with the outside of the catheter such that coolant may be deposited into blood stream. A coolant exit port can be smaller than the coolant injection port to allow pressure to increase in the expandable member to inflate it.

The catheter can also include a radiopaque marker positioned on a distal region of the catheter to indicate radial direction, optionally a radiopaque marker is asymmetric and positioned on the same side or opposing side as the electrodes.

The catheter can also include one or more temperature sensors, each disposed between pairs of electrodes. A temperature sensor can be configured to directly contact a blood vessel wall when the catheter is inserted in a blood vessel and the expandable member is in its expanded state. A control unit can be configured to receive a temperature signal from the temperature sensor and control the coolant source to inject coolant fluid based on said temperature signal and/or control the power source emission of ablation energy based on said temperature signal.

The following fifth part of the summary is intended to introduce the reader to various aspects relating dual electrode transvascular nerve ablation embodiments, but not to define or delimit any invention. Optionally the methods and devices described in this fifth part of the summary may use the devices or methods according to any one of the preceding aspects.

One aspect of this part is a transvascular ablation device adapted and configured for transvascular ablation of a preganglionic TSN or TSN nerve root, comprising: a proximal portion adapted to remain outside of a patient and a distal portion sized for insertion through the patient's vasculature, the distal portion comprising an elongate shaft, a first ablation member carried by the elongate shaft, a second ablation member carried by the elongate shaft, and an occlusion member carried by the elongate shaft and axially in between the first and second ablation members, the occlusion member adapted to have a delivery configuration and an expanded configuration.

The second ablation member may be axially spaced from the first ablation member by a distance of 3 mm to 6 mm.

At least one of the first ablation member and the second ablation member can have a length from 3 mm to 5 mm.

An outer diameter of the first ablation member can be from 1.5 mm to 3 mm, and an outer diameter of the second ablation member can be from 1.5 mm to 3 mm.

The occlusion member can have an axial length of 1 mm to 6 mm.

A diameter of the occlusion member in the expanded configuration can be from 3 mm to 5 mm, and optionally has a diameter in the delivery configuration from 1.5 mm to 2 mm.

The device can further comprise a guidewire lumen extending from the proximal portion to a guidewire exit port in the distal portion.

The first ablation member can be in electrical communication with a first electrical conductor, and the second ablation member can be in electrical communication with a second electrical conductor that is different than the first electrical conductor.

The first and second ablation members can each comprise an irrigation exit port in fluid communication with at least one irrigation lumen passing though the elongate shaft to the proximal portion where it is connectable to an irrigation fluid supply.

The first and second ablation members can each comprise an irrigation exit ports in fluid communication with an independent irrigation lumen passing though the elongate shaft to the proximal portion where they are connectable to an irrigation fluid supply.

Any irrigation exit port may have a diameter of 0.020"+/−0.005". Any of the irrigation exit ports can be positioned on a side of the first or second ablation members, respectively.

The first ablation member can comprise an electrode, the electrode comprising at least one irrigation exit port positioned in at least one channel that spans the length of the electrode. The first ablation member can comprise an electrode, the electrode comprising at least one irrigation exit port positioned in at least one scallop that spans a portion of a length of the electrode to at least a distal or proximal end of the electrode.

At least one of the first and second ablation members can comprise a cavity in fluid communication with at least two irrigation lumens passing though the elongate shaft to the proximal portion where a first of the at least two irrigation lumens can be connectable to an irrigation fluid supply and a second of the at least two irrigation lumens can be connectable to a fluid return receiver.

At least one of the first and second ablation members can comprise a temperature sensor.

The occlusion member can be an inflatable occlusion balloon.

The occlusion balloon can comprise a chamber, and the chamber can be in fluid communication with an inflation lumen passing through the elongate shaft to the proximal portion where it is connectable to an inflation fluid supply. A temperature sensor can be positioned within the chamber, and the temperature sensor can be adapted to monitor a temperature of fluid within the chamber.

One aspect of this part is a transvascular ablation device adapted and configured for transvascular ablation of a preganglionic greater splanchnic nerve or nerve root, comprising: a proximal portion adapted to remain outside of a patient and a distal portion sized for insertion through the patient's vasculature, the distal portion comprising an elongate shaft, a first ablation member carried by the elongate shaft, a second ablation member carried by the elongate shaft and axially spaced from the first ablation member, and an occlusion member carried by the elongate shaft and axially in between the first and second ablation members, the occlusion member adapted to have a delivery configuration and an expanded configuration.

At least one of the first and second ablation members can have an outer diameter from 1.5 mm to 3 mm. The occlusion member may have a diameter in the expanded configuration from 3 mm to 5 mm.

At least one of the first and second ablation members can have a length from 3 mm to 5 mm.

One aspect of this part is a transvascular ablation device adapted and configured for transvascular ablation of a preganglionic greater splanchnic nerve or nerve root, comprising: a proximal portion adapted to remain outside of a patient and a distal portion sized for insertion through the patient's vasculature, the distal portion comprising an elongate shaft, a first ablation member carried by the elongate shaft, a second ablation member carried by the elongate shaft and axially spaced from the first ablation member, wherein the first and second ablation members both have outer dimensions, optionally diameters, that are less than a diameter of the elongate shaft.

The outer dimensions can be from 1.5 mm to 2.5 mm.

The diameter of the elongate shaft can be from 2 mm to 3 mm.

The outer dimensions can be less than the diameter by 0.2 mm to 1 mm.

A portion of each of the first ablation member and the second ablation member can be electrically insulated and a remaining portion of each is electrically conductive, wherein the electrically conductive portion comprises a segment that is less than or equal to 50% of the circumference, less than 40%, less than 30%, or less than 25%.

The device can be adapted to be connected to an ablation console, the ablation console adapted to operate the ablation device in at least one of bipolar mode, monopolar mode, and a combination of bipolar and monopolar modes.

One aspect of this part is a method of ablating a TSN or TSN nerve root (e.g., a greater splanchnic nerve or a greater splanchnic nerve root) to increase splanchnic venous blood capacitance, comprising: advancing an elongate medical device into an azygous vein, the elongate medical device including a distal region, the distal region including a flexible shaft, a first ablation member carried by the shaft, and a second ablation member carried by the shaft that is axially spaced from the first ablation member, advancing the first ablation member from the azygous vein into a T9, T10, or T11 intercostal vein; delivering ablation energy from the first ablation member; and creating an ablation lesion and thereby ablating a portion of a great splanchnic nerve or a greater splanchnic nerve root.

The method can further comprise advancing the second ablation member from the azygous vein into the T9, T10, or T11 intercostal vein, and delivering ablation energy from the second ablation member.

The delivering steps can comprise delivering energy from the first and second ablation members in monopolar modes.

The delivering steps can comprise delivering energy from the first and second ablation members in a bipolar mode.

The delivering steps can comprise delivering energy from the first and second ablation members in a combination monopolar-bipolar mode.

The method can also include advancing an occlusion member into the T9, T10, or T11 intercostal vein in between the first and second ablation members. The occlusion member can be carried by the elongate shaft in between the first and second ablation members. The method can further comprise expanding the occluding member in the T9, T10, or T11 intercostal vein. The method can further comprise completely occluding the T9, T10, or T11 intercostal vein with the occlusion member.

Advancing the second ablation member can comprise positioning a proximal end of the second ablation member at an ostium of the azygous vein and the intercostal vein.

Advancing a first ablation member from the azygous vein into a T9, T10, or T11 intercostal vein can comprise advancing the first ablation member into the T9, T10, or T11 intercostal vein up to 20 mm from an ostium of the azygous to the intercostal vein, and wherein delivering ablation energy from the first ablation member can occur when the first ablation member is positioned up to 20 mm from the ostium.

When energy is delivered from the first ablation member, the second ablation member can be positioned in the azygous vein.

The method can further comprise expanding an occluding member at an ostium of the azygous vein and the intercostal vein, and wherein expanding the occluding member directs blood flow away from the ostium.

Energy can be delivered from the first ablation member in monopolar mode.

Creating the lesion may not include delivering ablation energy from the second ablation member.

The first and second ablation members can be operated in bipolar mode when the second ablation member is positioned in the azygous vein.

Creating an ablation lesion can comprise creating an ablation region that has a depth of at least 5 mm from the intercostal vein.

Creating an ablation lesion can comprise creating a circumferential ablation region.

The method can further comprise advancing the first ablation member from the azygous vein into one of the other of the T9, T10, and T11 intercostal veins and delivering ablation energy from the first ablation member when in the other of the T9, T10, and T11 intercostal veins.

Creating the lesion may not include delivering ablation energy from the second ablation member.

The method can further comprise delivering a stimulation signal from at least one of the first and second ablation members. Delivering a stimulation signal can comprise delivering a stimulation signal between the first and second ablation members in bipolar mode. The method can further comprise measuring a response to a stimulation signal. Delivering a stimulation signal and measuring a response can occur before delivering ablation energy from the first ablation member. Delivering a stimulation signal and measuring a response can occur after delivering ablation energy from the first ablation member.

The method can further comprise advancing an occlusion member into the T9, T10, or T11 intercostal vein proximal to the first ablation member. The occlusion member can be carried by the elongate shaft. The method can further comprise expanding the occluding member in the T9, T10, or T11 intercostal vein. The method can further comprise completely occluding the T9, T10, or T11 intercostal vein with the occlusion member. Expanding the occluding member can comprise delivering fluid into the occluding member.

The method can further comprise delivering irrigation fluid to at least one of the first and second ablation members. The method can include monitoring for irrigation fluid that is above a threshold temperature. The method can further comprise altering an energy delivery parameter if a monitoring step indicates irrigation fluid is above the threshold temperature. The method can further comprise controlling an irrigation fluid flow rate.

BRIEF DESCRIPTION OF THE DRAWINGS

The drawings included herewith are for illustrating various examples of articles, methods, and apparatuses of the present specification and are not intended to limit the scope of what is taught in any way. In the drawings:

FIG. 2 is an enlarged perspective view of the distal portion of the catheter of the device of FIG. 1.

FIG. 3 is an enlarged perspective view of the distal portion of the catheter of the device of FIG. 1, showing a needle guide in a working position.

DETAILED DESCRIPTION

Figure 1:
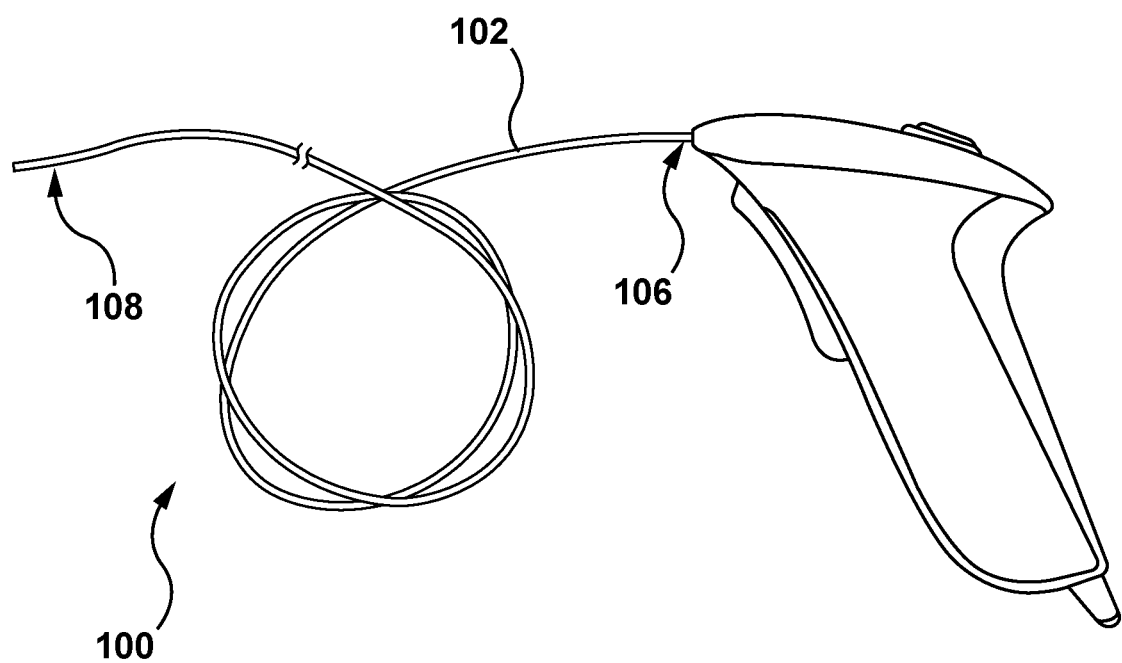
FIG. 1 is a perspective view of an example device for endovascular vein puncture.

This disclosure is related by subject matter to the disclosure in U.S. Pub. No. 2018/0110561, PCT Pub. No. WO2018/023132, and PCT Application No. PCT/US2018/066047 (filed Dec. 17, 2018), all of which are incorporated herein by reference in their entireties for all purposes.

The disclosure herein is generally related to methods of treating at least one of heart failure and hypertension by increasing splanchnic capacitance. Some approaches include systems, devices, and methods for transvascular (e.g., transvenous) ablation of target tissue to increase splanchnic capacitance. The devices and methods may, in some examples, be used for ablating one or more splanchnic nerves to increase splanchnic capacitance. For example, the devices disclosed herein may be advanced endovascularly to a target vessel in the region of a target nerve including a thoracic splanchnic nerve ("TSN"), such as a preganglionic greater splanchnic nerve ("GSN"), lesser splanchnic nerve, or least splanchnic nerve or one of their roots (a TSN nerve root). The target vessel may be, for example, an intercostal vein or an azygos vein (or both) or a vein of the azygos vein system, preferably, one or more of the lowest (i.e., most caudal) three intercostal veins (which may be T9, T10, and T11). A target region in a target vein for example may include a lumen in an intercostal vein, and can be a region that does not extend more than 30 mm into the vein from the adjoining azygos or hemiazygos vein, and optionally does not extend more than 20 mm into the vein from the adjoining azygos or hemiazygos vein. The target region thus has a distal end that is not further than a particular distance (or range of distances) from the ostium. Methods of use herein that position an ablation element (or ablation member generally) in a target region of a vessel are therefore not limited to requiring that the entire length of the ablation element is positioned in the target vessel, but rather they include methods in which a proximal portion, perhaps a relatively small portion thereof (e.g., less than 25% of the length) is still positioned in an adjacent vessel (e.g., an azygous vein). Methods herein that describe placing an ablation element or member in a target vessel within a certain distance from an ostium are therefore generally describing positioning a distal end of the ablation element within the target region of the target vessel, regardless of whether the entirety of the ablation element is within the same vessel (e.g., intercostal vein) or whether a portion is disposed in an adjacent vessel (e.g., azygous vein). In any of the methods herein, less than 50% of the length of the ablation element may be positioned in the adjacent vessel, such as less than 45%, or less than 40%, or less than 35%, or less than 30%, or less than 25%, or less than 20%, or less than 15%, or less than 10%.

A TSN may be up to 5 mm from a target intercostal vein in most humans. Intercostal veins at the lower levels (e.g., T9, T10, T11 levels) may have inner lumens in the target regions having a diameter range of 2 to 3.5 mm. A TSN, in particular a fully formed GSN, may traverse a target intercostal vein in the target region between an adjoining azygos or hemiazygos vein and a distance of no more than 15 mm from the adjoining azygos or hemiazygos. Beyond a distance of 20 mm from the adjoining azygos or hemiazygos a sympathetic trunk may traverse the intercostal vein.

Ablation of a TSN by thermal coagulation may involve heating tissue with an ablation element positioned in the target intercostal vein, which presents various technical challenges. Thermal ablation from a small vein can cause the vessel to shrink during energy delivery, which can drastically alter the thermal and electrical environment of an ablation element, particularly if the vessel shrinks around the ablation element, for example caused by a significant change in tissue contact or blood flow, making energy delivery erratic and ablation less predictable or controlled.

With devices and methods disclosed herein, the TSN may be ablated in a relatively safe manner, with minimal or reduced adverse effects (such as damage to the lungs or other nerves). Some method of use embodiments herein may temporarily occlude blood flow and reduce an effect of vein collapse, thus advantageously avoiding challenges of a changing thermal and electrical environment during the heating process. Some method of use embodiments herein may ablate a nerve up to 5 mm from the target vessel. Some of the devices herein are dimensioned and configured for delivery and positioning in vasculature specified for ablating a target nerve (e.g., TSN, GSN).

Some of the devices herein may have one or more features that provides for a safe delivery to the target vessel.

Some of the devices and methods of use herein may safely deliver energy with temperature monitored energy delivery.

Some of the methods of use herein may generate a lesion capable of targeting a nerve up to 5 mm away from the target vessel and within a target region having a continuous lesion length of up to 20 mm (e.g., 15 mm, 12 mm) with a single positioning and delivery of energy.

Some of the devices and methods herein are adapted to avoid risks of boiling, hot spots, or erratic energy delivery that could decrease ablation efficacy. Furthermore, some embodiments may include nerve stimulation to identify a target nerve or non-target nerve to confirm positioning prior to ablation, or to confirm technical success during or following ablation.

Studies performed to inform this disclosure indicated that the lowest three intercostal veins are likely best positioned for the placement of the medical ablation devices because the TSN, GSN or GSN roots (target nerves) are very likely to cross one or more of the lowest three intercostal veins between the ostium to the azygous vein and within a particular distance from the ostium. One aspect of this disclosure is thus a preferred method that includes positioning the medical devices (at least an ablation member portion thereof) in one of a particular number of intercostal veins, and additionally within a particular distance from the ostium of the azygous vein. This location and placement will provide the highest likelihood that, when activated, the medical device will effectively ablate the target nerves, described in more detail below.

It may be preferred, but not required, that the methods of ablation create a continuous ablation zone (i.e., not having separate, discrete regions of ablated tissue that are not connected to each other). This ensures that the region of tissue where the target GSN nerve or GSN nerve root is likely to be located is most likely to be effectively ablated by the ablation energy. The continuous ablation zone may be circumferential, or less than circumferential.

It may also be preferred, but not required, that the methods of ablation create an ablation zone that has a depth of at least 5 mm and a length in a range of 5 to 20 mm, and preferably in the range of 10 to 20 mm. Ablation regions or zones with these parameters increase the likelihood that the ablation region will include the target GSN or GSN root. While this disclosure generally describes lesions with a length in the range of 5-20 mm, it may be possible to effectively ablate a target nerve with a lesion that has a length of less than 5 mm, such as between 1 mm and 5 mm. For example, some target nerves may be quite close to an ostium between, for example, an azygous vein and an intercostal vein, and it may be acceptable to create an ablation region or zone with a length of less than 5 mm and still effectively ablate the target nerve. Unlike treatments that are targeting nerves that innervate a vessel (e.g., some renal denervation approaches), these exemplary methods of treatment are targeting one or more target nerves that are in relatively close proximity to the intercostal vein and traverse or cross, rather than follow, the vein. Traverse in this context does not mean the nerve passes through the vein structure in any way, but rather refers to the general relative orientation of the nerves and veins.

It is understood that while some methods herein create a lesion that has a length within a particular range, the methods may inherently create these ablation lengths even if the length of the ablation zone is not a direct input to a procedure. For example, if a console or energy generator is used to deliver energy, one or more delivery parameters may be selected as part of the procedure (e.g., time, power, etc.), and ablation length is not necessarily an input to the procedure. This means that the ablation zone length may occur as a result of a procedure, even if the length is not particularly selected by a user or is not input to an energy generating device such as a generator. If a result of a procedure is that a lesion is created with a length in the ranges herein (or even likely to be created with a length in the ranges herein, then the method is understood to fall within the scope of a claim that includes an ablation zone length.

Endovascular Vessel Puncture Embodiments

Disclosed herein are devices and methods for endovascular vein puncture, and subsequent treatment of a target structure (e.g., a nerve) that is exterior to the vein. The devices and methods may, in some examples, be used for splanchnic nerve ablation for treatment of heart failure. For example, the devices disclosed herein may be advanced endovascularly to a target vein in the region of a thoracic splanchnic nerve (TSN), such as a greater splanchnic nerve (GSN) or a TSN nerve root. The target vein may be, for example, an intercostal vein or an azygos vein or a vein of the azygos vein system. The device may then be activated or deployed to puncture the vein wall of the target vein. The device may then be activated or deployed again to treat the TSN, for example by temporarily blocking the TSN or permanently ablating the TSN. Ablation of the TSN may be carried out, for example, by radiofrequency (RF) ablation, cryoablation, thermal ablation, chemical ablation, or pharmaceutical ablation. Ablation of the TSN may affect circulating blood volume, pressure, blood flow and overall heart and circulatory system functions, as described in Patent Application No. PCT/US2017/044747, in order to treat heart failure. Ablation of the TSN may also have therapeutic benefits such as treating intractable abdominal pain or motility. With the devices and methods disclosed herein, the TSN may be ablated in a relatively safe manner, with minimal or reduced adverse effects (such as damage to the lungs or other nerves).

Endovascular Vessel Puncture Devices

Referring to FIG. 1, a first example of a device 100 for endovascular vein puncture is shown. The device 100 includes an elongate catheter 102, which extends along a longitudinal axis 104 (also referred to herein as a 'catheter axis') (shown in FIG. 2) and has a catheter proximal portion 106 and a catheter distal portion 108. The catheter distal portion 108 may generally function as the working end of the device 100. The catheter proximal portion 106 may generally remain exterior to a patient in use, and may be manipulated by a physician or other professional. The catheter 102 has a catheter outer diameter 110 (shown in FIG. 2).

In some examples, the catheter can include a braided shaft to facilitate torqueability (i.e., transmission of torque from the catheter proximal portion 106 to the catheter distal portion 108), particularly over a tortuous delivery path.

Referring to FIG. 2, in the example shown, the catheter 102 includes a guidewire lumen (not shown) extending therethrough (along the catheter axis 104), and the catheter distal portion 108 includes a guidewire exit port 112, so that the catheter 102 can be advanced into the venous system along a guidewire. The catheter 102 has a circumferential outer surface 114 and a distal end surface 116, and in the example shown the guidewire exit port 112 is at the distal end surface 116.

In alternative examples, the guidewire lumen and exit port may be omitted, and the catheter may be advanced into a patient's cardiovascular system (e.g., into a vein or artery) without the aid of a guidewire.

The catheter outer diameter 110 may be sized to pass into the azygos vein of a patient, and optionally into the intercostal veins of a patient. For example, the catheter outer diameter 110 may be between about 1 mm and 5 mm, or between about 1 mm and 3 mm.

Referring to FIGS. 2 and 3, in the example shown, the device 100 further includes a needle guide 101, which has a distal end 103 (also referred to herein as a "needle guide distal end") that is blunt. The needle guide 101 is deployable from the catheter 102, from a needle guide storage position (shown in FIG. 2, in which the needle guide 101 is not visible) to a needle guide working position (shown in FIG. 3).

In general, the needle guide storage position can be any position in which the needle guide distal end 103 is withdrawn towards the catheter 102, relative to the needle guide working position. Referring still to FIGS. 2 and 3, in the example shown, when the needle guide 101 is in the storage position, the needle guide distal end 103 is nested within the catheter. The needle guide 101 is deployable from the catheter 102 via a side port 109 in the circumferential outer surface 114 of the catheter. When in the deployed position, the needle guide 101 extends from the side port 109, so that the needle guide distal end 103 is radially spaced from the catheter 102 (i.e., spaced from the catheter 102 in a direction transverse to the catheter axis 104). In the example shown, when in the needle guide working position, the needle guide 101 is generally straight, and is inclined with respect to the catheter axis 104. In alternative examples, the needle guide can be bent or curved, and/or can be perpendicular with respect to the catheter axis 104.

Referring still to FIG. 3, in the example shown, the needle guide 101 is relatively short. That is, in the example shown, when the needle guide 101 is in the needle guide working position, the needle guide distal end 103 is radially spaced from the catheter by a needle guide deployed distance 111. In some examples, the needle guide deployed distance 111 is selected so that when the needle guide 101 is in the deployed position and abuts a vein wall (e.g., an intercostal vein wall, an azygos vein wall, or a wall of a vein of the azygos vein system), the needle guide distal end 103 is forced against the vein wall with some pressure (as will be described below). For example, when the needle guide 101 is in the deployed position and abuts a vein wall, it can push the catheter 102 to abut an opposing vein wall, which then in turn forces the needle guide distal end 103 against the vein wall. To facilitate the application of sufficient pressure by the needle guide distal end 103 to the vein wall, the catheter diameter 110 plus the needle guide deployed distance 111 may be equal to or slightly larger than the inner diameter of a targeted vein, when the needle guide is fully deployed. In situations where a patient's vein diameter is a little smaller than the combined distance of the catheter diameter 110 and the needle guide deployed distance 111, the vein may stretch to accommodate full deployment of the needle guide 101. For example, such a catheter configured to be used in a human's T10 or T11 intercostal vein may have a catheter diameter 110 plus needle guide deployed distance 111 equal to a distance in a range of 2 mm to 4 mm (e.g., in a range of 2.5 mm to 3.5 mm). In another example, such a catheter configured to be used in a human's azygos or hemiazygos vein at a level of T10 or T11 may have a catheter diameter 110 plus needle guide deployed distance 111 equal to a distance in a range of 3.5 mm to 6.5 mm (e.g., in a range of 4 to 5 mm). Optionally, a user may size a target vessel prior to delivering an ablation catheter (e.g., with CT angiography or other medical imaging modality) and select a suitable ablation catheter depending on the diameter of the target vein. In some examples the needle guide deployed distance 111 is less than the catheter outer diameter 110. For example, the needle guide deployed distance 111 can be between about 0.5 mm and about 6 mm or between about 0.5 mm and about 3 mm, or between about 2 mm and about 6 mm.

Figure 4:
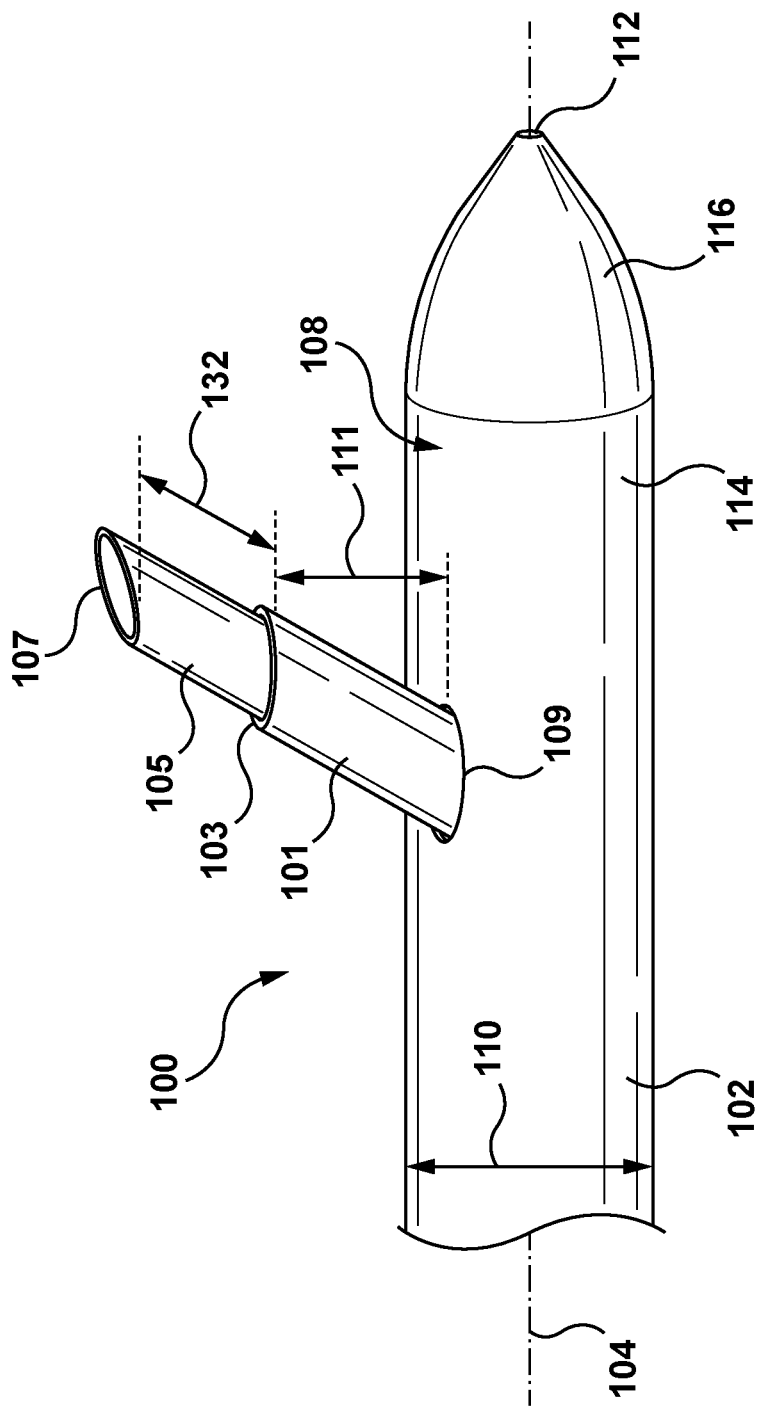
FIG. 4 is an enlarged perspective view of the distal portion of the catheter of the device of FIG. 1, showing a needle in a puncturing position.

Referring to FIGS. 3 and 4, in the example shown, the device further includes a needle 105, which has a sharp puncturing end 107. The needle 105 is deployable from within the needle guide 101, from a needle storage position (shown in FIG. 3, in which the needle 105 is not visible) to a puncturing position (shown in FIG. 4).

Referring still to FIGS. 3 and 4, in the example shown, when the needle 105 is in the needle storage position, it is within the needle guide 101, so that the puncturing end 107 is shy of the needle guide distal end 103. When in the puncturing position, the needle 105 protrudes from the needle guide 101, so that the puncturing end 107 extends proud of the needle guide distal end 103.

Referring to FIG. 4, in the example shown, the needle 105 is relatively short. That is, in the example shown, when the needle 105 is in the puncturing position, the puncturing end 107 is spaced from the needle guide distal end 103 by a needle deployed distance 113. In some examples, the needle deployed distance 113 is selected to be long enough to just puncture a vein wall, such as an intercostal vein wall or an azygos vein wall, without protruding significantly beyond the vein wall. This can allow for accurate puncture of a vein while minimizing or reducing the risk of damaging nearby tissue, such as lung tissue. For example, the needle deployed distance 113 can be less than 2 mm, or less than 1 mm, or about 0.5 mm. In some examples, the needle deployed distance 113 is less than the catheter outer diameter 110.

Figure 5:
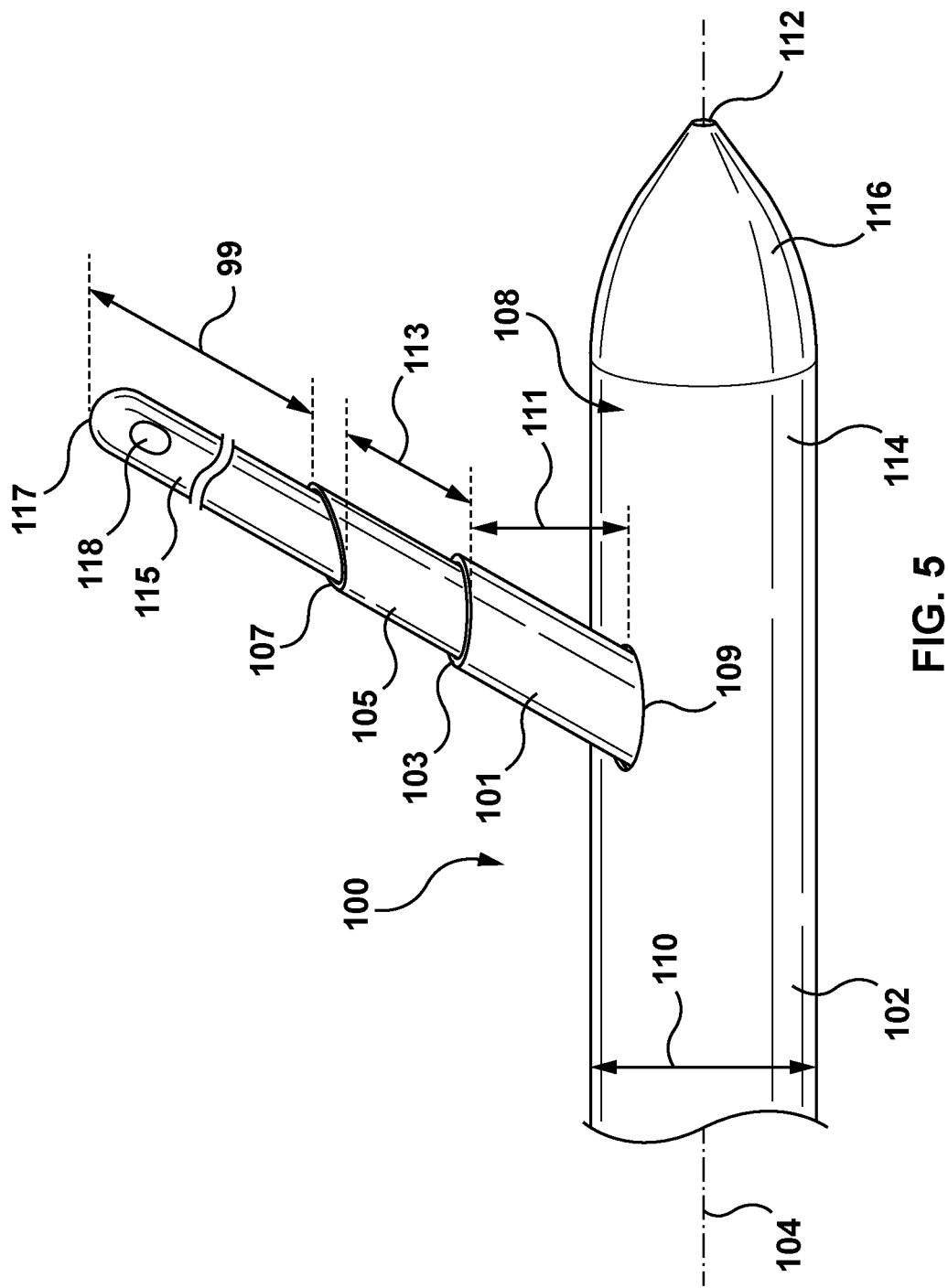
FIG. 5 is an enlarged perspective view of the distal portion of the catheter of the device of FIG. 1, showing a delivery device in a treatment position.

Referring to FIG. 5, in the example shown, the device 100 further includes a delivery device 115, which can deliver a treatment to a patient. The treatment can in some examples be for nerve ablation, such as TSN nerve ablation. For example, the delivery device 115 can be a fluid delivery device (for delivery of an ablative chemical or pharmaceutical), a thermal energy delivery device (for delivery of heat), a cryoablative energy delivery device, an electrical energy delivery device, and/or an RF energy delivery device. The treatment can be delivered circumferentially from the delivery device 115, or longitudinally (also referred to as 'directionally') from the delivery device 115.

Referring still to FIG. 5, in the example shown, the delivery device 115 is a probe that has a blunt distal end 117 (also referred to herein as a 'delivery device distal end'), which is generally rounded. The delivery device 115 further includes a fluid port 118, which is located proximally of the blunt distal end 117, on a side wall of the delivery device 115. The fluid port 118 can be for delivering a fluid, such as a chemical or pharmaceutical ablative agent, an anesthetic, a cooling fluid, or another fluid.

Referring still to FIGS. 4 and 5, in the example shown, the delivery device 115 is deployable from within the needle 105, from a delivery device storage position (shown in FIG. 4, in which the delivery device 115 is not visible), in which it is housed within the needle 105 and the needle guide 101, to a delivery device treatment position (shown in FIG. 5), in which the delivery device distal end 117 extends proud of the puncturing end 107 of the needle. In the example shown, the fluid port 118 also extends proud of the puncturing end 107 of the needle.

In the example shown, when in the delivery device treatment position, the delivery device 115 extends proud of the puncturing end 107 by a delivery distance 99. The delivery distance 99 can be selected to position the delivery device 115 proximate a treatment location. For example, if the device 100 is being used to ablate the GSN via puncture of an intercostal vein, the delivery distance 99 can be between about 3 mm and about 7 mm, or between about 4 mm and about 6 mm. Alternatively, if the device 100 is being used to ablate the GSN via puncture of an azygos vein or vein of the azygos vein system, the delivery distance 99 can be up to 15 mm.

In alternative examples, the delivery device 115 can be omitted. In such examples, a treatment may be delivered directly from the needle 105. For example, a pharmaceutical agent could be delivered directly from the needle.

The device 100 of FIGS. 1 to 5 may include one or more radiopaque markers, for facilitating advancement, positioning or orientation of the device. The radiopaque marker(s) may be, for example, on the catheter, the needle guide, the needle, or the delivery device. For example, the catheter distal portion 108 may be advanced to a target location in a vessel, and prior to deploying a needle guide 101, the user may visually assess the rotational orientation of the catheter distal portion 108 by imaging the catheter 102, the radiopaque marker, and/or parts of the patient's anatomy, using fluoroscopy. This can indicate the direction in which the needle guide 101 will deploy.

Figure 17:
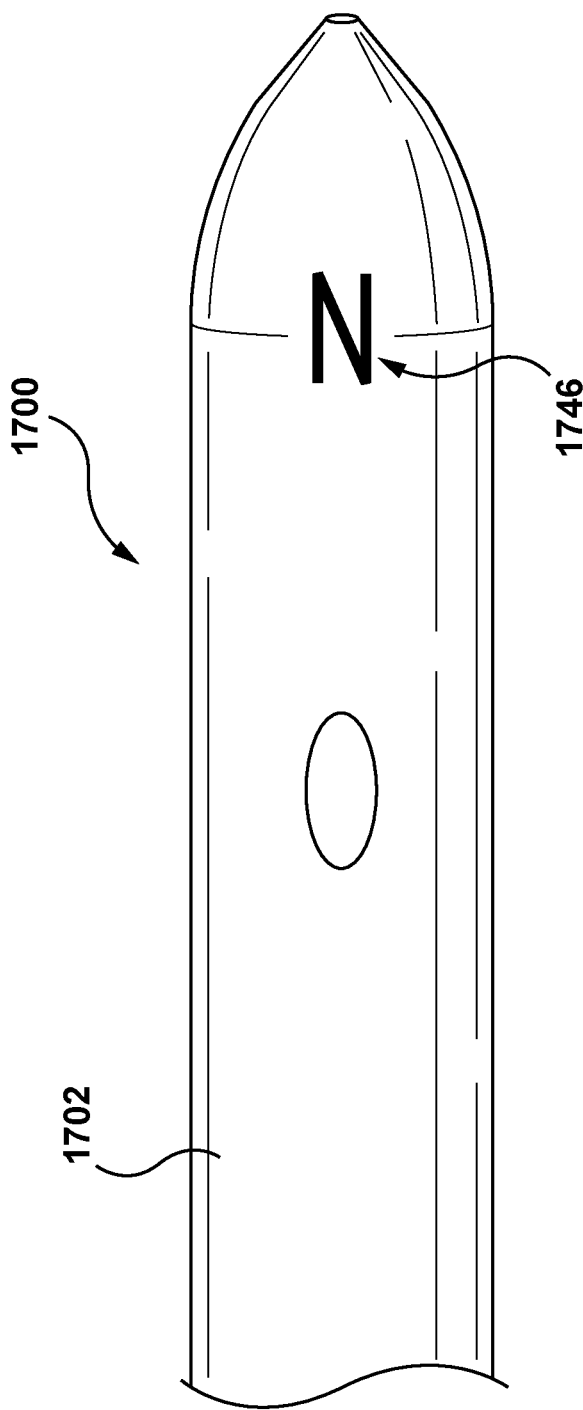
FIG. 17 is an enlarged top plan view of the distal portion of the catheter of an alternative example device for endovascular vein puncture.
Figure 19:
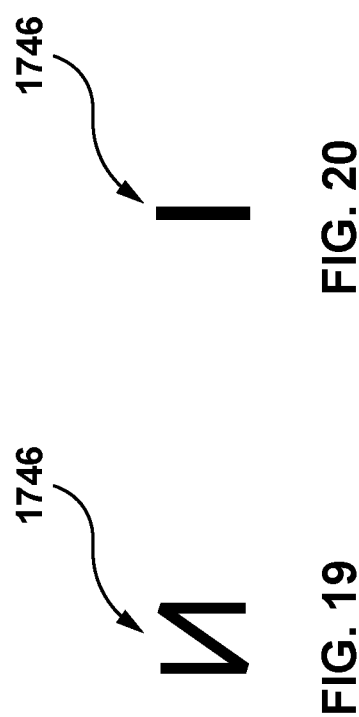
FIG. 19 is a schematic view showing the appearance of the radiopaque marker of the device of FIG. 17 under fluoroscopy, when the device is at a rotational orientation opposite to the desired rotational orientation.
Figure 20:
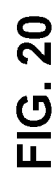
FIG. 20 is a schematic view showing the appearance of the radiopaque marker of the device of FIG. 17 under fluoroscopy, when the device is at a sideways rotational orientation with respect to the desired rotational orientation.
Figure 18:
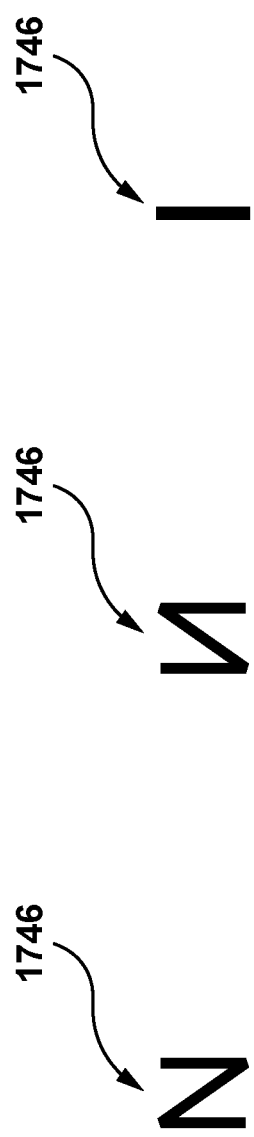
FIG. 18 is a schematic view showing the appearance of the radiopaque marker of the device of FIG. 17 under fluoroscopy, when the device is at a desired rotational orientation.

Referring to FIG. 17, a device 1700 that includes a radiopaque marker 1746 that is configured to facilitate placement of a catheter 1702 at a desired orientation is shown. The device 1700 is similar to the device 100, and for simplicity, features that are like those of the device 100 will not be described in detail. In the device 1700, the radiopaque marker 1746 is configured to distinguish when the radiopaque marker 1746 is rotationally aimed at a C-arm head. Since the position of the radiopaque marker 1746 is circumferentially aligned with the direction of deployment of the needle guide (not shown), the radiopaque marker 1746 can be used to indicate when the needle guide is aimed at a C-arm head. In the example shown, the radiopaque marker 1746 is made from a radiopaque material and is asymmetric in shape. Specifically, the radiopaque marker 1746 is N-shaped. If the radiopaque marker 1746 is facing towards the C-arm head, the radiopaque marker 1746 will appear as the letter N, as shown in FIG. 18. If the radiopaque marker 1746 is facing away from the C-arm head (e.g., toward the vertebra), the radiopaque marker 1746 will appear as a backwards letter N, as shown in FIG. 19. If the radiopaque marker 1746 is sideways, the radiopaque marker 1746 will appear as a line, as shown in FIG. 20.

Figure 21:
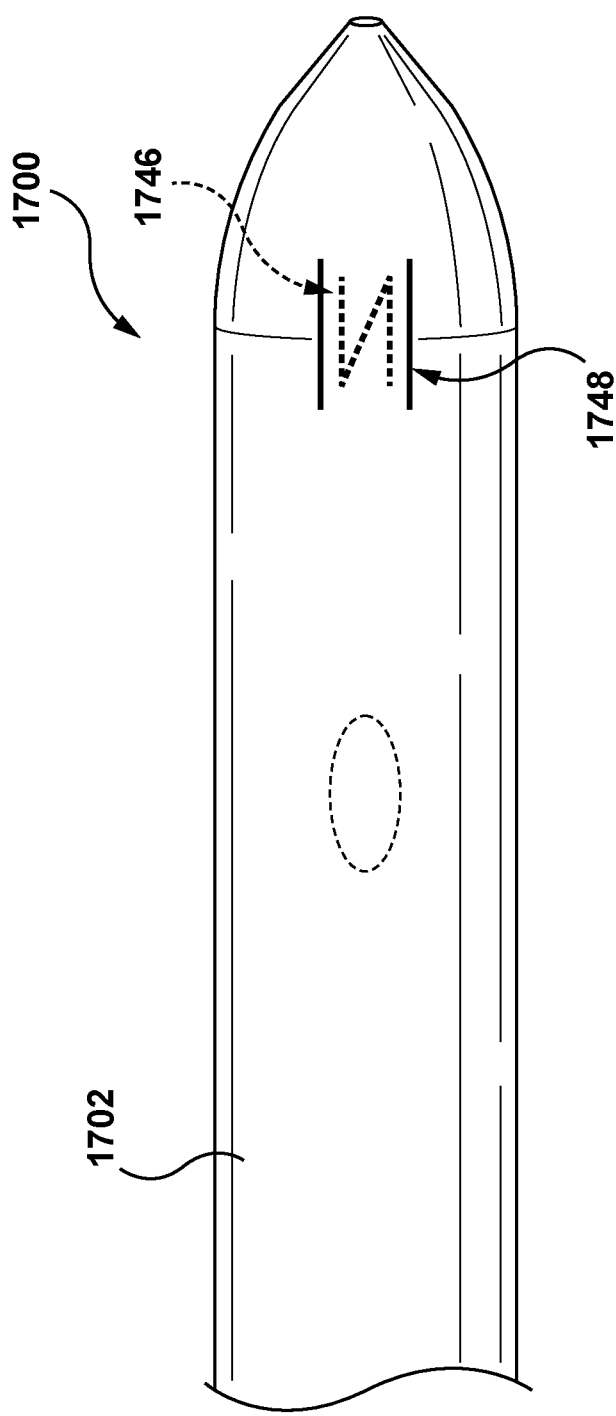
FIG. 21 is an enlarged bottom plan view of the distal portion of the catheter of the device of FIG. 17.
Figure 23:
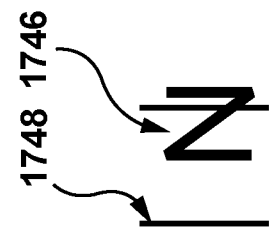
FIG. 23 is a schematic view showing the appearance of the additional radiopaque marker of the device of FIG. 17 under fluoroscopy, when the device is not within a desired rotational tolerance.
Figure 22:
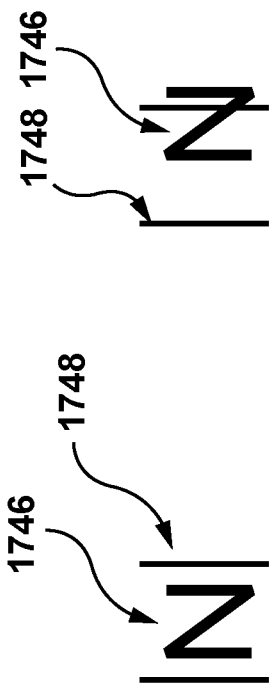
FIG. 22 is a schematic view showing the appearance of the additional radiopaque marker of the device of FIG. 17 under fluoroscopy, when the device is within a desired rotational tolerance.

Referring to FIG. 21, in the example shown, the device 1700 further includes an additional radiopaque marker 1748 that is configured to visually indicate when the rotational position of the catheter 1702 is within a set tolerance. Particularly, the additional radiopaque marker 1748 includes two lines the center of which is circumferentially spaced from the radiopaque marker 1746 by about 180 degrees, so that the radiopaque marker 1746 appears between the lines of the additional radiopaque marker 1748 when the orientation is within the set tolerance, as shown in FIG. 22. When the orientation is outside the set tolerance, the radiopaque marker 1746 will overlap one of the lines of the additional radiopaque marker 1748 or will be outside of the lines of the additional radiopaque marker 1748, as shown in FIG. 23. For example, the set tolerance may be up to 45 degrees on either side of perfect alignment (e.g., up to 35 degrees, or 25 degrees, or 15 degrees, or 5 degrees).

Figure 6:
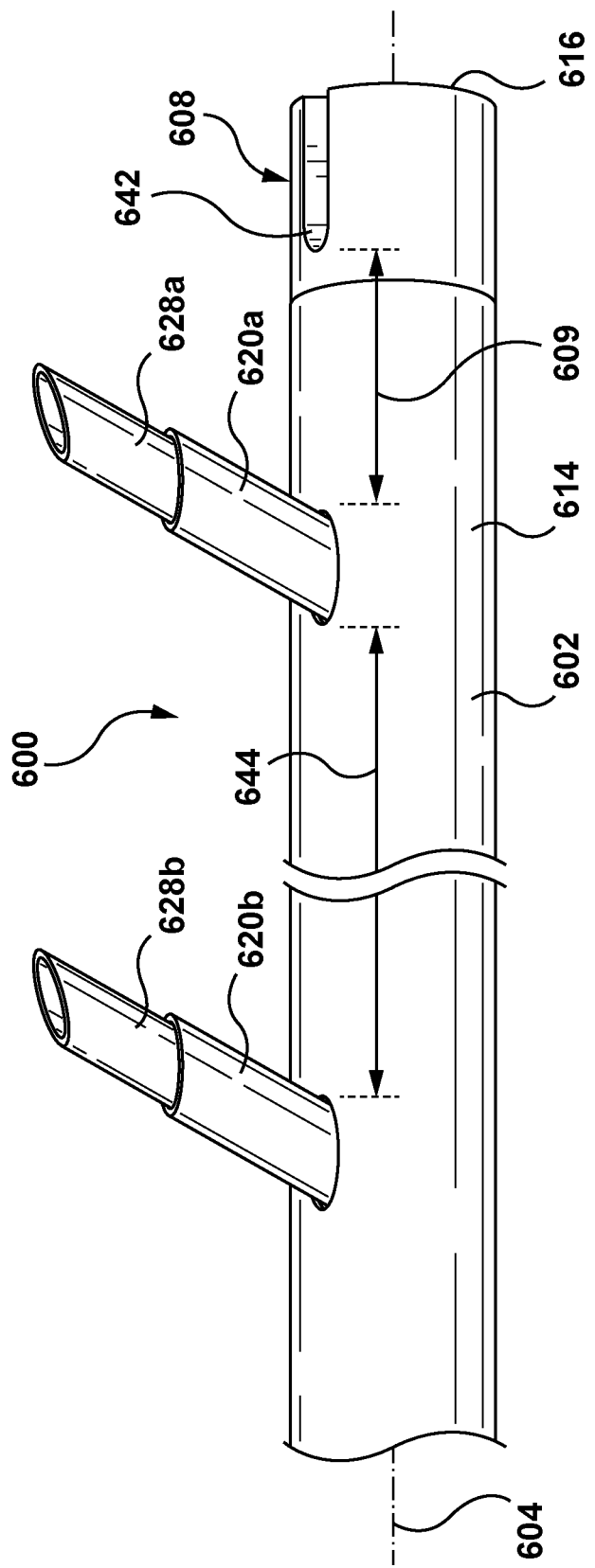
FIG. 6 is an enlarged perspective view of a distal portion of a catheter of another example device for endovascular vein puncture.
Figure 8:
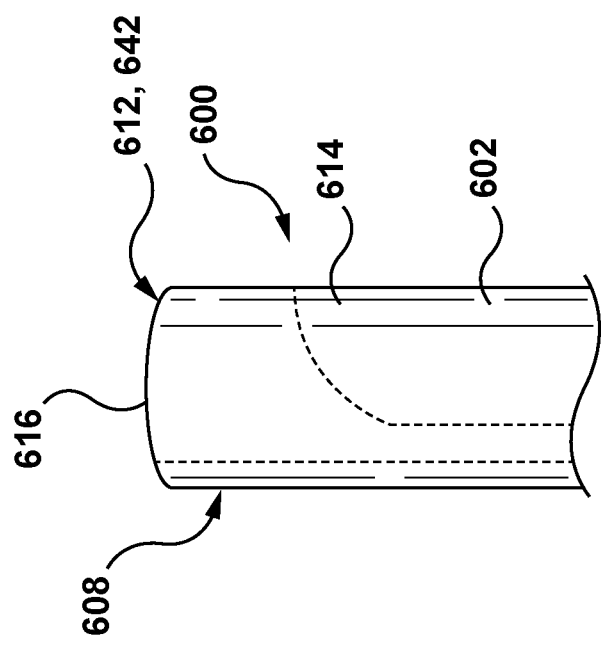
FIG. 8 is an enlarged plan view of the distal portion of the catheter of FIG. 6.
Figure 7:
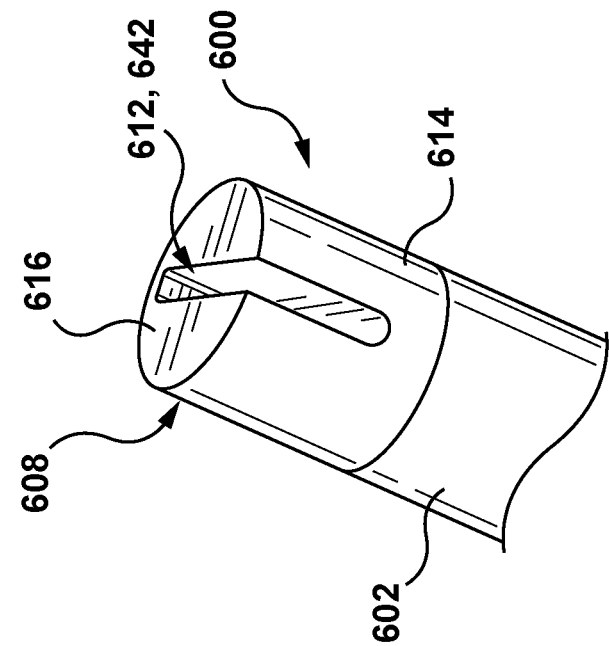
FIG. 7 is a further enlarged perspective view of the distal portion of a catheter of FIG. 6.

Referring now to FIGS. 6 to 8, another example device 600 for endovascular vein puncture is shown. The device 600 is similar to the device 100 of FIGS. 1 to 5, and for simplicity, features that are like those of the device 100 will not be described in detail. Furthermore, in the description of device 600, features that are like those of device 100 will be referenced with like reference numerals to those of device 100, but incremented by 500.

Referring to FIG. 6, similarly to the device 100, the device 600 includes a catheter 602, a needle guide 620*a* (also referred to herein as a 'first needle guide') that is deployable from the catheter 602 in a direction that is transverse to the catheter axis 104, and a relatively short needle 628*a* (also referred to herein as a 'first needle') that is deployable from the needle guide 620. However, the device 600 further includes a second needle guide 620*b* that is deployable from the catheter 602 in a direction that is transverse to the catheter axis 104 (this direction may be referred to herein as a 'second direction' that is transverse to the catheter axis), and a second needle 628b that is deployable from the second needle guide 620b. The second needle guide 620b and second needle 628b are similar in configuration and operation to the first needle guide 620a and first needle 628a, and will not be described in detail.

Referring still to FIG. 6, in the example shown, the first needle guide 620a and first needle 628a are longitudinally spaced apart from a notch 642 at the distal end 608 by a spacing 609 of between 1.5 cm and about 2.5 cm, or about 2 cm to coincide with a distance between an anchoring vein and a first target position (e.g., an anchoring vein may be a T11 intercostal vein in which a guidewire is delivered and a first target position may be in an azygos vein between a T10 and T11 intercostal vein). Furthermore, the first needle guide 620a and first needle 628a are longitudinally spaced apart from the second needle guide 620b and second needle 628b. That is, the first needle guide 620a is deployable from the catheter 602 at a first longitudinal position on the catheter 602, the second needle guide 620b is deployable from the catheter 602 at a second longitudinal position on the catheter 602, and the second longitudinal position is spaced from the first longitudinal position. The second longitudinal position may be spaced from the first longitudinal position by a spacing 644 of between about 3 cm and about 5 cm, or of about 4 cm to coincide with a distance between target positions (e.g., a first target position may be in an azygos vein between a T10 and T11 intercostal vein and a second target position may be in the azygos vein between a T9 and T10 intercostal vein).

Referring still to FIG. 6, in the example shown, the first needle guide 620a and first needle 628a are circumferentially aligned with the second needle guide 620b and second needle 628b. That is, the first needle guide 620a is deployable from the catheter 602 at a first circumferential position on the catheter, the second needle guide 620b is deployable from the catheter 602 at a second circumferential position on the catheter 602, and the second circumferential position is aligned with the first circumferential position.

The device of FIG. 6 may allow for the treatment of a relatively large anatomical area with simplicity, and/or in a relatively short time frame. That is, a treatment (e.g., an ablative treatment) can be delivered simultaneously from the first needle 628a and the second needle 628b, to ablate a large area.

Similar to the device 100, the first needle 628a and second needle 628b can each optionally house a respective delivery device for delivering a treatment.

Referring to FIGS. 7 and 8, similarly to the device 100, the device includes a guidewire lumen, and a guidewire exit port 612 at the catheter distal end 608. However, the guidewire exit port 612 is a notch 642 (also referred to herein as an 'orienting notch'), and the notch 642 is open at both the distal end surface 616 and the circumferential outer surface 614, and between these two surfaces.

In the example shown, the notch 642 is open at a notch circumferential position on the catheter. The notch circumferential position can in some examples be within 30 degrees of the first circumferential position and/or the second circumferential position. In the example shown, the notch circumferential position is aligned with the first circumferential position and the second circumferential position.

The circumferential positioning of the notch 642 with respect to the first 620a and second 620b needle guides can be used to facilitate positioning of the first 620a and second 620b needle guides at a desired orientation in use. For example, as will be described in detail below, in use, a guidewire can be directed in a particular direction, for example laterally from a first vessel (e.g., a vein or artery) into a second vessel. The catheter 602 can then be advanced over the guidewire, stopping in the first vein. The catheter 602 can then be rotated about the catheter axis 604 until the guidewire falls into the notch 642. When the guidewire falls into the notch 642, the first 620a and second 620b needle guides will be pointed laterally in the same direction as the second vein.

The device of FIGS. 6 to 8 may include one or more radiopaque markers, for facilitating advancement, positioning and/or orientation of the device. The radiopaque marker(s) may be, for example, on the catheter, the needle guide(s), the needle(s), or the delivery device(s). In the example shown, the distal tip of the catheter (including the distal end surface 616 and the portion of the circumferential outer surface 614 adjacent the notch 642) is radiopaque.

Figure 24:
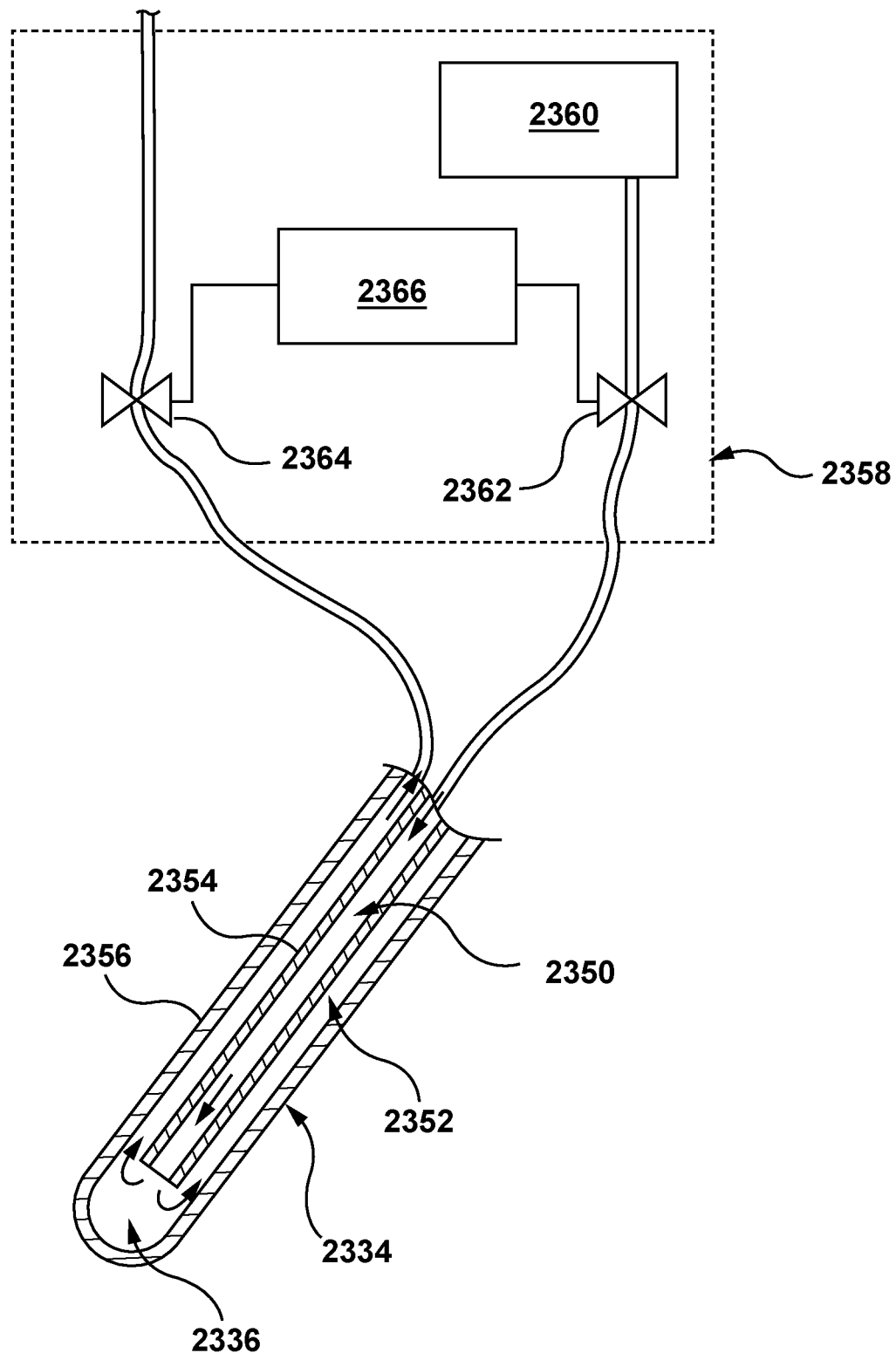
FIG. 24 is a schematic view of a delivery device of an alternative example device for endovascular vein puncture.

As mentioned above, the devices described herein may include a delivery device for delivering a treatment, and the delivery device can deliver cryogenic energy (also referred to as cryoablative energy). The use of cryogenic energy for ablation may be in some examples beneficial, as it may allow for a controlled and predictable ablation zone (e.g., a zone extending circumferentially around the delivery device by about 3 to 5 mm), may obviate the need to keep freely delivered fluid in a target zone, may allow for treatment to be better visualized (e.g., because ice can be seen on medical imaging), may be less painful than other ablation modes, and may be used for temporary nerve blocking. Referring now to FIG. 24, an example cryogenic energy delivery device 2334 is shown. For simplicity, in FIG. 24, the other features of the device, such as the needle guide and needles, are not shown.

In the example shown, the cryogenic energy delivery device 2334 includes a first lumen 2350 (also called a supply lumen) for delivery of a cryogenic fluid (e.g., liquid nitrogen, such as supercritical liquid nitrogen as described in U.S. Pat. No. 7,921,657) from a source 2358 to the distal end 2336 of the cryogenic energy delivery device 2334, and a second lumen 2352 (also called a return lumen) for return of the cryogenic fluid to the source 2358 (e.g., for recycling or for eventual disposal or venting). In the example shown, the first lumen 2350 is formed by a central tube 2354 within the cryogenic energy delivery device 2334, and the second lumen is formed between the central tube 2354 and the outer wall 2356 of the cryogenic energy delivery device 2334, so that the first lumen 2350 and second lumen 2352 are coaxial. In alternative examples, the first 2350 and second 2352 lumens may be formed in another manner, for example, by two adjacent tubes within the cryogenic energy delivery device 2334.

In some examples the central tube 2354 and the outer wall 2356 may be formed by stainless steel hypodermic tubes. The distal end 2336 of the delivery device 2334 may have a dome welded end.

In some examples, the distal end 2336 of the delivery device 2334 may include one or more temperature sensors (not shown). In some examples, the delivery device 2334 may include one or more stimulation electrodes (not shown). For example, the delivery device 2334 may include two spaced apart band electrodes, which may be used in a bipolar mode.

In some examples (not shown), the catheter and/or needle and/or needle guide may be thermally insulated, so that the cryoablation is delivered only from the delivery device 2334, and not from other parts of the device.

In examples wherein the device includes two needles, two needle guides, and two cryogenic energy delivery devices (such as the device 600), a single supply lumen may supply both cryogenic energy delivery devices.

Referring still to FIG. 24, in the example shown, the source 2358 of cryogenic fluid includes a fluid reservoir 2360, a supply valve 2362 between the fluid reservoir 2360 and the first lumen 2350, a pressure release valve 2364 at the exit of the second lumen 2352 for venting the returned cryogenic fluid to atmosphere, and a controller 2366 for controlling the supply valve 2362 and the pressure release valve 2364. The controller 2366 may be in communication with a temperature sensor at the distal end 2336 of the delivery device 2334, and supply of the cryogenic fluid may be automatically controlled in response to the sensed temperature. Alternatively, supply of the cryogenic fluid may be manually controlled.

In some examples, the delivery device 2334 may cyclically deliver cryogenic energy and thermal energy (e.g., using RF). This may be used for reversible blocking of a myelinated nerve by delivering thermal energy to reversibly block the nerve (i.e., by delivering thermal energy for a relatively short time at a relatively low temperature, e.g., between 1 min and 4 mins, below 60 power of 2 to 50 W, or below 20 W), then delivering cryogenic energy to reversibly block the nerve (i.e., by delivering cryogenic energy for a relatively short time and at a relatively high temperature, e.g., above 15 degrees Celsius). The RF energy may be delivered via the outer wall 2356 of the delivery device 2334. Alternatively, the delivery device can include one or more electrodes (e.g., two band electrodes) on the outer wall 2356, and the outer wall 2356 can be electrically insulative.

In some examples (not shown), a delivery device similar to delivery device 2334 may be used in a device that does not include a needle guide or a needle, in order to deliver cryogenic energy without puncturing a vein. In such a device, RF energy may be used to warm the vein and shrink it around the cryogenic energy delivery device before cooling, so that blood flow is reduced (which impedes cooling power). Alternatively, occluding balloons may be deployed distal and proximal to the cryogenic energy delivery device, to stop blood flow from impeding cooling.

The devices described above can optionally include various sensors and electrodes. For example, the devices 100 and/or 600 can include one or more temperature sensors and/or bio-impedance sensors. For further example, the devices 100 and/or 600 can include one or more electrical stimulation electrodes. Such sensors and electrodes can be positioned on the catheter, the needle guide(s), the needle(s), and/or the delivery device(s). Such sensors and electrodes are described in detail in Patent Application No. PCT/US2017/044747.

In any of the above examples, the delivery devices (e.g., delivery device 115) can be configured to be flexible, so that if contact with a lung occurs, the delivery device can bend to accommodate movement of the lung, to minimize or reduce damage to the lung. For example, if a flexible delivery device contacts or even punctures the lung, movement of the lung can result in flexing of the delivery device, instead of tearing of the lung. For example, a flexible delivery device may include a flexible shaft with sufficient axial compression strength to allow it to be advanced through soft tissue, such as fat, as it is advanced toward a target, and the flexible shaft may be a coiled spring.

Methods of Using Endovascular Vessel Puncture Devices

Certain anatomical structures of the thorax will be referenced below. These anatomical structures are described and shown in detail in US Pub. No. 2018/0110561, PCT Pub. No. WO2018/023132, and PCT Application No. PCT/US2018/066047 (filed Dec. 17, 2018), which are fully incorporated by reference herein for all purposes.

In the context of this document, the TSN can mean right or left thoracic splanchnic nerve and their contributing nerves, and endovascular puncture and treatment (e.g., ablation) can be performed from the azygos vein or one or more intercostal veins to access the right thoracic splanchnic nerve, or from the hemiazygos vein or intercostal veins to access the left thoracic splanchnic nerve, or from their respective tributaries, or a bilateral treatment can be performed from both the azygos and hemiazygos veins and their tributaries to access both right and left thoracic splanchnic nerves.

A first example method for endovascular puncture and treatment will be described with reference to FIGS. 9 to 13. The method will be described with reference to the device 100 of FIGS. 1 to 5. However, the method is not limited to the device 100, and the device 100 is not limited to use according to the method.

In the example shown, the method is for endovascular puncture of an intercostal vein, and treatment of the GSN by ablation. The method is shown in the T10 intercostal vein. In alternative examples, the method may be carried out in other intercostal veins, such as the T9 or T11 intercostal vein, examples of which are described herein. Ablation of the GSN may be for the purpose of treating heart failure or other related conditions, as described in US Pub. No. 2018/0110561, PCT Pub. No. WO2018/023132, and PCT Application No. PCT/US2018/066047 (filed Dec. 17, 2018). In alternative examples, similar methods can be used for endovascular puncture of other vessels, for other treatment purposes.

The intercostal vein may be accessed endovascularly by several approaches, including from a subclavian vein, a jugular vein, or a femoral vein. Various approaches are described in US Pub. No. 2018/0110561, PCT Pub. No. WO2018/023132, and PCT Application No. PCT/US2018/066047 (filed Dec. 17, 2018), and will not necessarily be described in detail herein.

Figure 9:
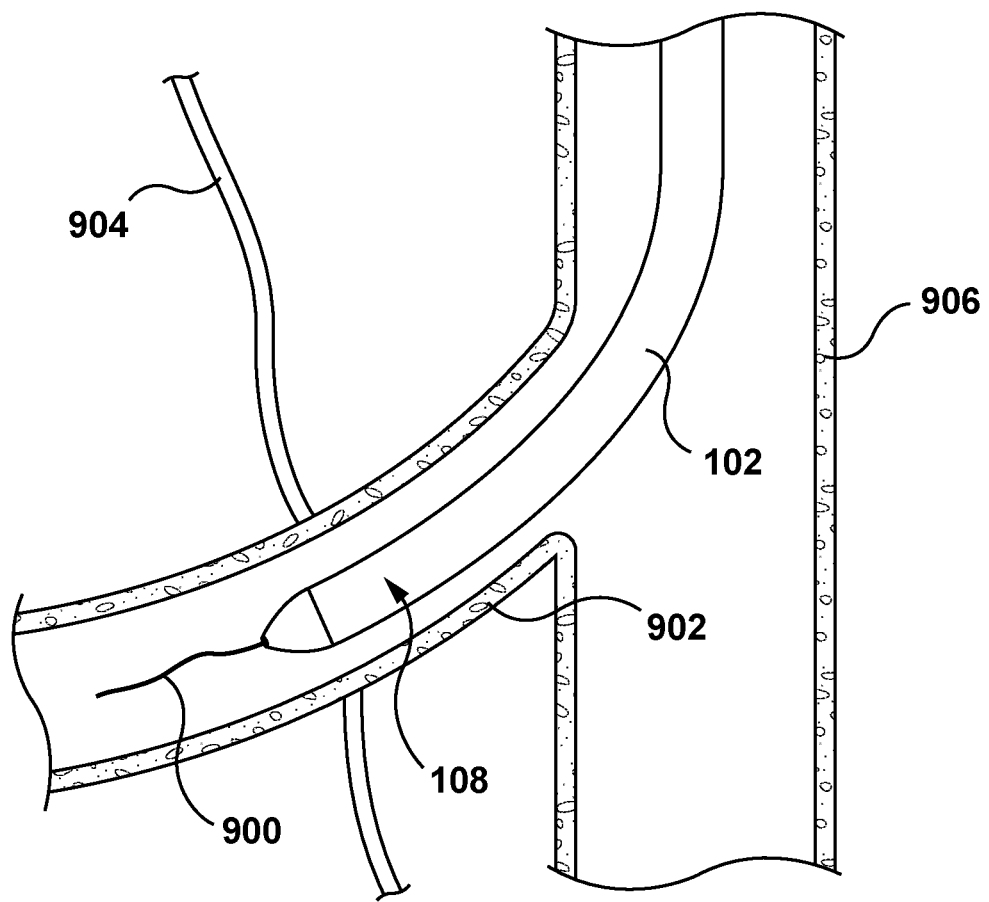
FIG. 9 is a schematic view of a portion of the thorax of a patient, with a guidewire in position in a T10 intercostal vein of the patient, and with the device of FIG. 1 advanced over the guidewire to a target location.

Referring now to FIG. 9, as a first step, a guidewire 900 may be advanced through the patient's venous system, into the T10 intercostal vein 902. The catheter distal portion 108 may then be advanced over the guidewire 900 through the venous system and into the T10 intercostal vein 902, to a target location within the T10 intercostal vein 902. In some examples, the target location is up to about 3 cm into the T10 intercostal vein 902. In some examples, wherein the treatment is for ablation of the GSN 904, and wherein damage to the sympathetic chain is to be avoided, the target location may be up to about 1.5 cm into the T10 intercostal vein 902 from the azygos vein 906, or up to about 1 cm into the T10 intercostal vein 902. In some examples, the catheter 102 may be advanced by about 3 cm or greater into the T10 intercostal vein, and then a stimulation pulse may be applied from the catheter 102. If the pulse stimulates the sympathetic chain, the catheter can be withdrawn slightly. Stimulation and withdrawal can be repeated until the stimulation pulse stimulates the GSN without stimulating the sympathetic chain.

In some examples (not shown), a radiopaque marker (such as radiopaque markers 1746 and 1748 described above) of the catheter 102 may be used to facilitate placement of the catheter 102 at a desired rotational orientation. The desired orientation may be the orientation in which the needle guide 101 will deploy in a radial direction that is away from the vertebra (e.g., opposite the vertebra) and towards the TSN. For example, if the target vessel is a right T11 intercostal vein, a C-arm fluoroscope may be centered on a T11 vertebra, and optionally rotated from an anterior-posterior center position (AP position) to the patient's right side to obtain an angle that is approximately orthogonal to the tangent of the vertebra. In this position, it can be desired to have the needle guide 101 deploy in a radial direction toward the C-arm head, which is where the GSN often traverses the intercostal vein. The catheter 102 may be torqued to rotate the catheter distal portion 108 within the intercostal vein until the radiopaque marker indicates that the needle guide 101 will be deployed toward the C-arm and thus toward the target nerve.

Since the GSN is often between the intercostal vein and the parietal pleura, and the pleura in this location often has approximately the same contour as the vertebral column, deploying the needle guide 101 orthogonal to the tangent of the vertebra can direct the needle guide orthogonal to the pleura. Even though the needle 105 punctures only a slight amount past the vein wall, and the delivery device 115 can have a blunt end, there may still be a small risk of puncturing through the parietal pleura, in which case the fluid or energy may not be effectively delivered to the GSN. By delivering the needle 105 or delivery device 115 at an oblique angle (e.g., about 45 degrees) instead of orthogonal, the risk of puncturing the pleura can be reduced. Thus, in alternative examples, a catheter may include a radiopaque marker that is circumferentially spaced from the needle guide, so that when the radiopaque marker is aimed at the C-arm head, the needle guide deploys in a direction that is not aimed at the C-arm head (e.g., degrees away from the C-arm head.

Figure 10:
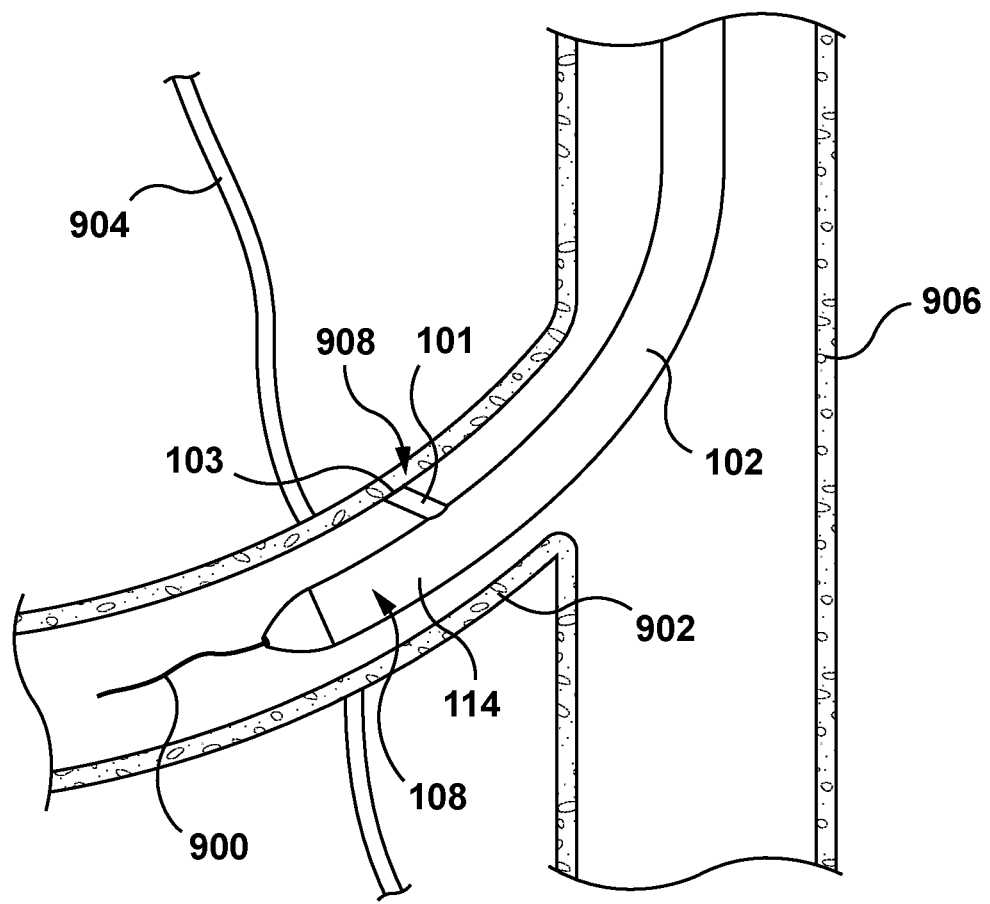
FIG. 10 is the schematic view of FIG. 9, with the needle guide of the device being advanced towards a working position.
Figure 11:
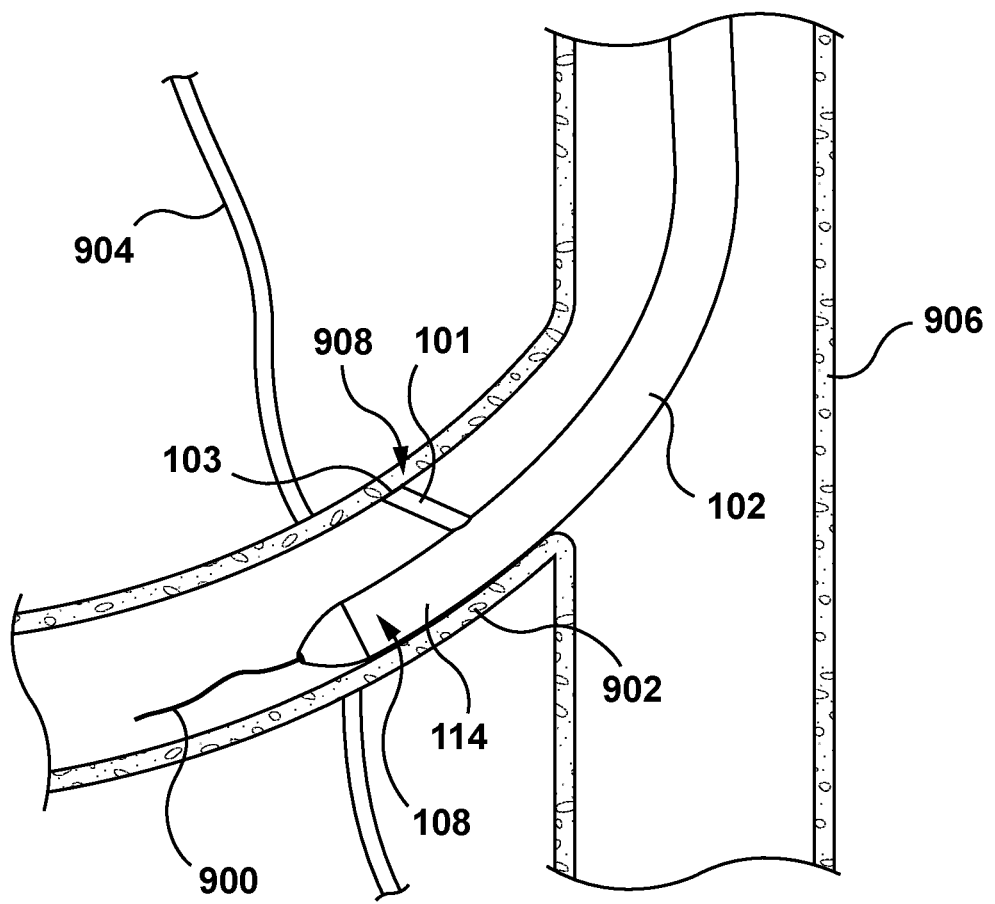
FIG. 11 is the schematic view of FIG. 10, with the needle guide of the device in the working position.

Referring to FIGS. 10 and 11, the needle guide 101 may then be deployed from the catheter 102. As discussed above in the "Devices" section, the needle guide 101 can be deployed in a direction that is transverse to the catheter axis 104 (shown in FIG. 1), so that the needle guide distal end 103 is radially spaced from the circumferential outer surface 114 of the catheter 102. The needle guide 101 can be deployed until the needle guide distal end 103 contacts the vein wall 908, as shown in FIG. 10. Continued deployment can cause the needle guide distal end 103 to be forced against the vein wall 908 (in preparation for deployment of the needle 105). For example, continued deployment can cause the catheter 102 to be pushed away from the vein wall 908, so that the catheter 102 abuts the opposing wall 910 of the vein 902 (also referred to herein as an 'opposing vein wall'), as shown in FIG. 11, or contacts another anatomical structure. Alternatively, continued deployment can cause other movement of the catheter 102 which results in the distal end 103 applying pressure to the vein wall 908 in preparation for deploying the needle 105.

Figure 12:
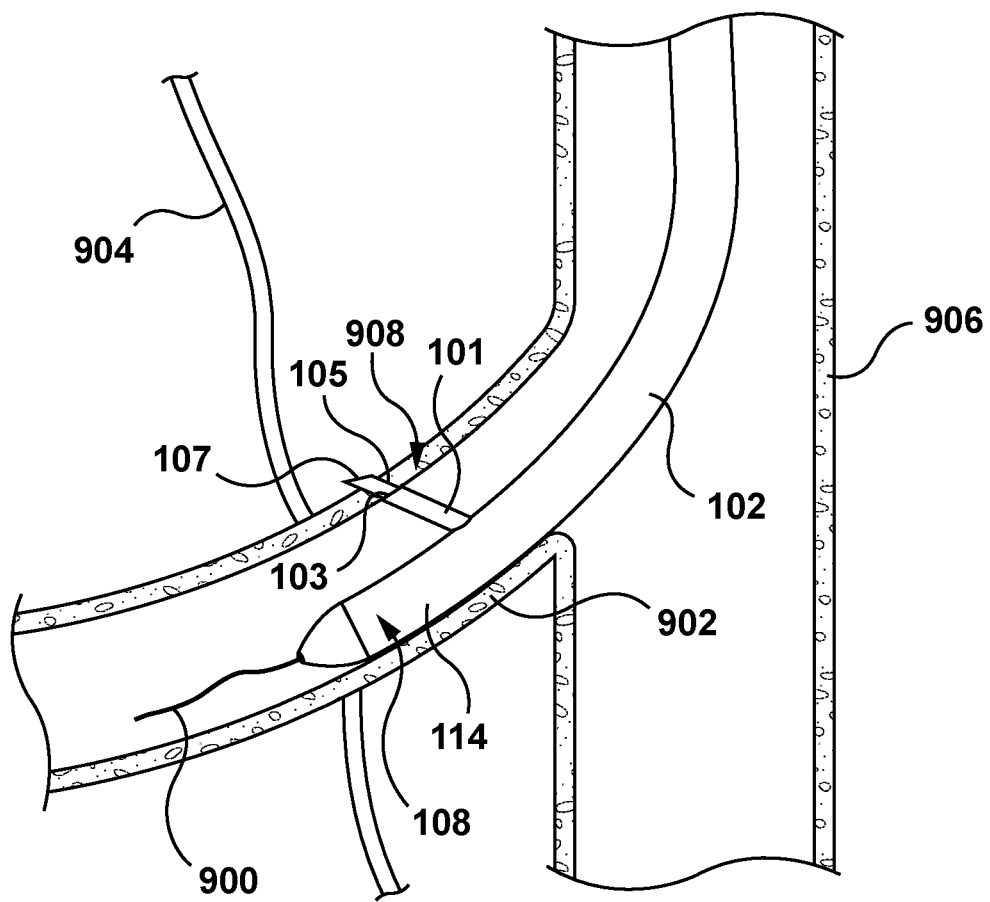
FIG. 12 is the schematic view of FIG. 11, with the needle of the device being in the puncturing position.

Referring to FIG. 12, when the needle guide distal end 103 is forced against the vein wall 908 (e.g., as a result of the catheter 102 abutting the opposing vein wall 910 or another anatomical structure), the needle 105 may be deployed from the needle guide distal end 103, to puncture the vein wall 908 with the sharp puncturing end 107 of the needle 105. Due to the relatively short puncturing distance of the needle 105, the vein wall 908 can be punctured accurately while minimizing or reducing the risk of puncture of the lungs or other nearby tissues. For example, as noted above, the needle 105 can be deployed to a deployed distance that is less the catheter outer diameter 110 (shown in FIG. 2), and/or that is less than 2 mm, or less than 1 mm, or about 0.5 mm.

When the vein 902 has been punctured, various optional steps can be carried out. For example, a nerve stimulation test can be carried out, by delivering an electrical stimulation pulse via the sharp puncturing end 107, in order to confirm the position of the sharp puncturing end 107 with respect to the GSN 904 or other nerves or anatomical structures. For further example, a contrast agent can be delivered to confirm that the lung or parietal pleura has not been punctured.

A treatment may then be delivered to the region exterior to the vein 902, via the sharp puncturing end 107 of the needle 105. In the example shown, the delivery device 115 is deployed from the puncturing end 107 and is used to deliver the treatment. In alternative examples, the needle 105 itself may deliver the treatment. For example, a fluid (such as an ablative fluid) may be delivered via the needle.

Figure 13:
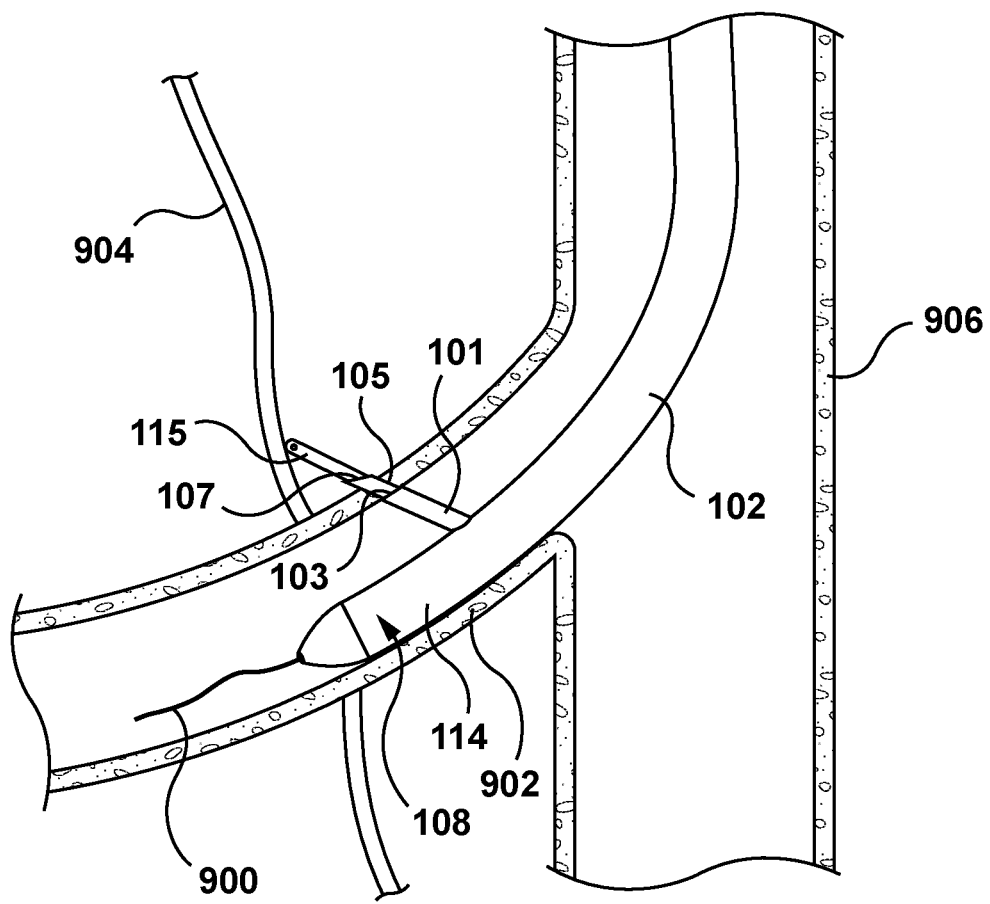
FIG. 13 is the schematic view of FIG. 12, with the delivery device of the device in the treatment position proximate a greater splanchnic nerve.

Referring to FIG. 13, as mentioned above, the delivery device 115 can be deployed from the puncturing end 107 by a delivery distance 99 (shown in FIG. 5). Depending on the mode of treatment, the delivery distance 99 can be, for example, up to 15 mm, or between 3 mm and 7 mm, or between 4 mm and 6 mm. In many situations, in order to ablate the GSN 904 from an intercostal vein using RF energy, the delivery device 115 can be deployed by between 4 mm and 6 mm. Optionally, a nerve stimulation test can be carried out by delivering a pulse via the delivery device 115, in order to confirm the position of the delivery device 115 with respect to the GSN 904 or other nerves or anatomical structures.

A treatment can then be delivered from the delivery device 115. For example, as mentioned above, a treatment fluid can be delivered, or a thermal energy treatment can be delivered, or a cryogenic energy treatment can be delivered, or an RF energy treatment can be delivered.

Upon completion of treatment, the device 100 may be withdrawn from the patient, by retracting the delivery device 115 towards the needle 105, retracting the needle 105 towards the needle guide 101, and retracting the needle guide 101 towards the catheter 102, and then withdrawing the catheter distal portion 108 through the venous system of the patient.

Figure 14:
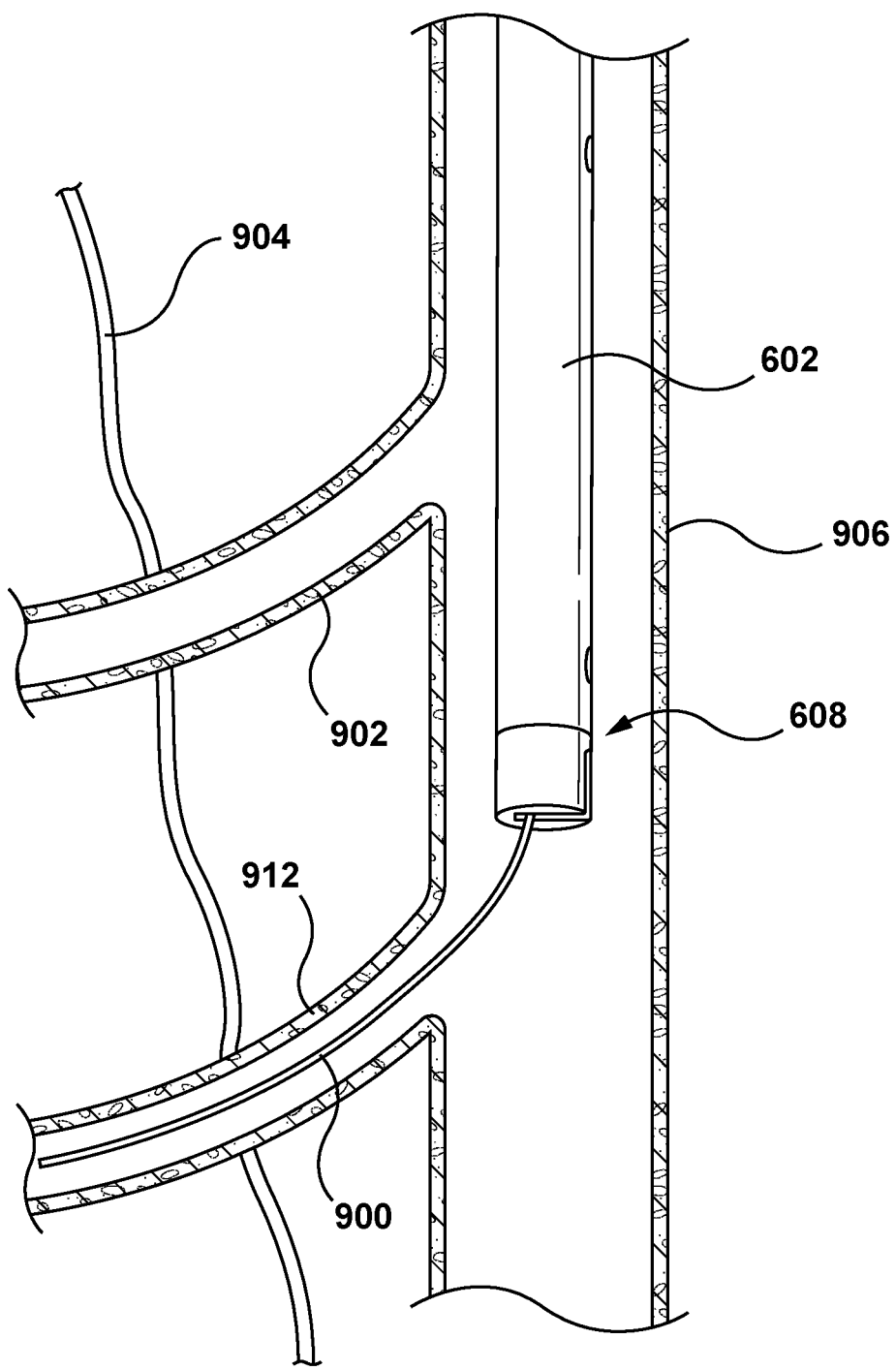
FIG. 14 is a schematic view of a portion of the thorax of a patient, with a guidewire in position in a T11 intercostal vein of the patient, and with the device of FIG. 1 advanced over the guidewire to a target location within the azygos vein.
Figure 15:
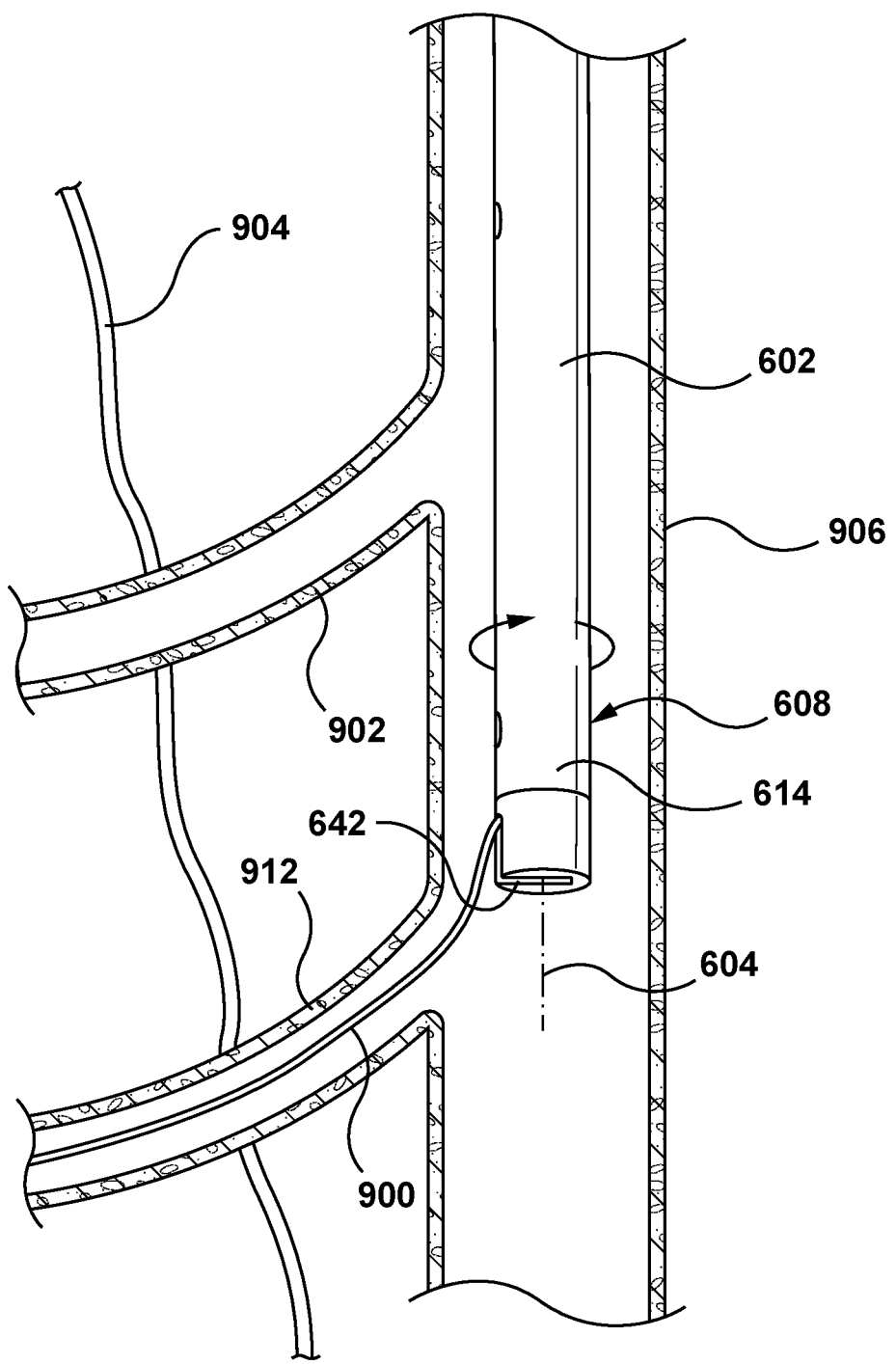
FIG. 15 is the schematic view of FIG. 14, with the catheter of the device rotated to adjust its orientation, until the guidewire falls into the notch of the catheter.
Figure 16:
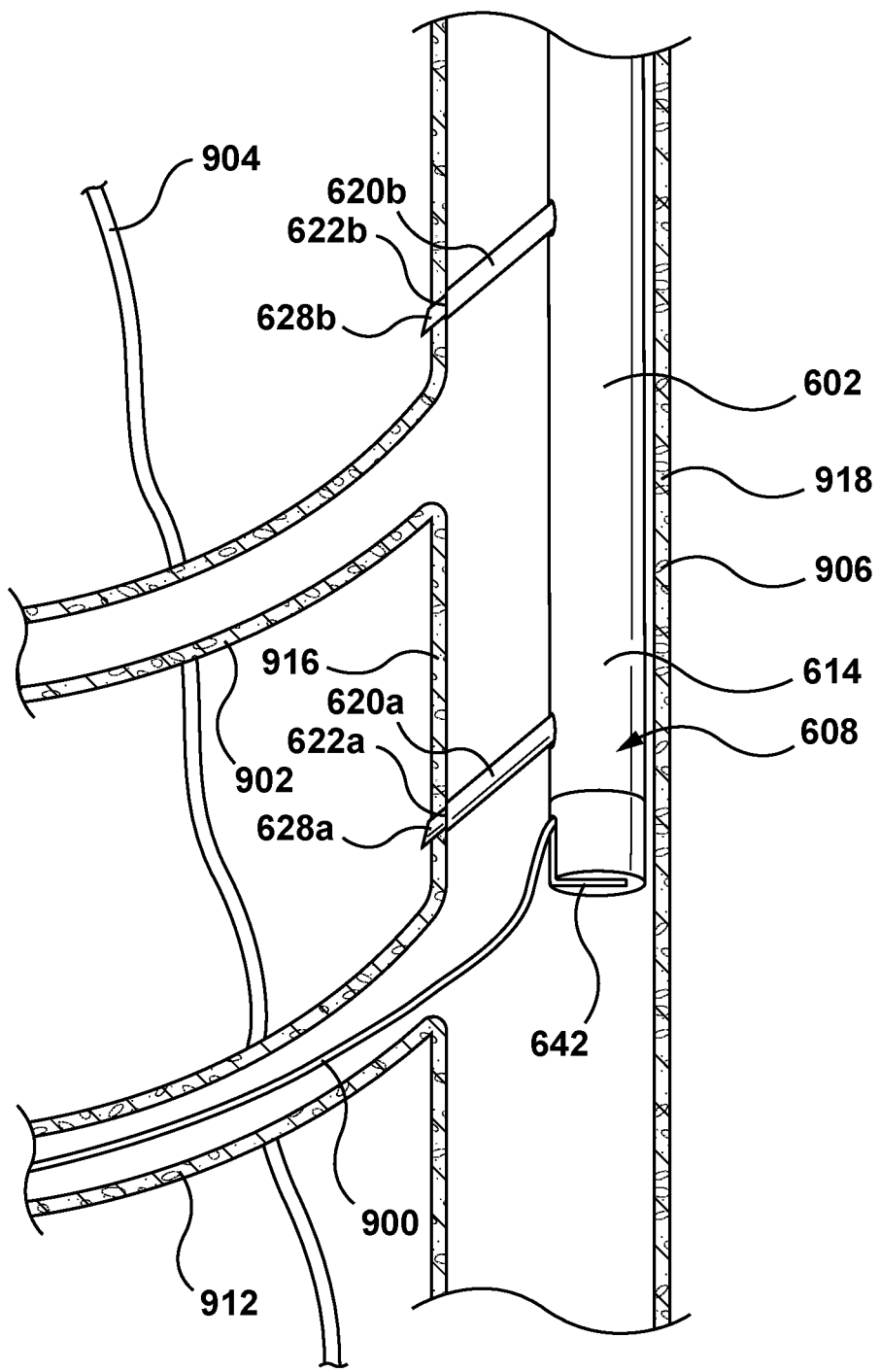
FIG. 16 is the schematic view of FIG. 15, with the needle guides and the needles deployed.

Referring now to FIGS. 14 to 16, another method for endovascular puncture and treatment will be described. The method will be described with reference to the device 600 of FIGS. 6 to 8. However, the method is not limited to the device 600, and the device 600 is not limited to use according to the method.

In the example shown, the method is for endovascular puncture of the azygos vein 906 at the T9 to T11 level on the right side, and treatment of the GSN 904 by ablation. The azygos vein 906 may be accessed endovascularly by several approaches, including from a subclavian vein, a jugular vein, or a femoral vein. Various approaches are described in International Patent Application No. PCT/US2017/044747, and will not be described in detail herein.

Referring now to FIG. 14, in the example shown, as a first step, a guidewire 900 may be advanced through the patient's venous system. Although the azygos vein 906 is the target for puncture, the guidewire 900 may be advanced through the azygos vein 906 and into the T11 intercostal vein 912. The catheter distal portion 608, may then be advanced over the guidewire 900 through the venous system and into the azygos vein 906, to a target location within the azygos vein 906. In some examples, the target location may be between the T9 and T11 level. For example, the catheter distal portion 608 may be positioned so that the first needle guide 620a (shown in FIG. 16), when deployed, is between the T10 intercostal vein 902 and the T11 intercostal veins 912 and so that the second needle guide 620*b*, when deployed, is between the T9 intercostal vein (not shown) and T10 intercostal vein 902.

Referring to FIG. 15, when the catheter distal portion 608 is at the target location, its orientation may be adjusted so that when deployed, the first 620*a* and second 620*b* needle guides (shown in FIG. 16) are directed towards the GSN 904. On the right side of the body, the intercostal veins are generally on the same side of the azygos vein 906 as the GSN 904 and approximately in the same plane as the GSN 904, and the placement of the guidewire 900 in the T11 intercostal vein 912 can facilitate adjustment of the rotational orientation of the catheter 602.

That is, with the guidewire 900 in the T11 intercostal vein 912 and the catheter distal portion 608 at the target location in the azygos vein 906, the catheter 602 can be rotated about the catheter axis 604. When the notch 642 in the catheter distal portion 608 is oriented in the same direction as the T11 intercostal vein 912—i.e., towards the GSN 904—the guidewire 900 will fall into the notch 642, and will nest into the portion of the notch 642 that is open at the circumferential outer surface 614. This positioning of the guidewire 900 (i.e., nested into the portion of the notch 642 that is open at the circumferential outer surface 614) can be confirmed under fluoroscopy.

In alternative examples, a device may be used in which the notch and the first and second needle guides are circumferentially spaced apart by about 30 degrees. This can reduce or minimize the risk of puncturing a lung, since the first and second needle guides will be directed slightly away from the lung and towards the vertebrae.

Referring to FIG. 16, with the orientation of the catheter 602 confirmed, the first 620*a* and second 620*b* needle guides can be deployed from the catheter 602, either sequentially or simultaneously. As described above, the first 620*a* and second 620*b* needle guides can be deployed until the blunt needle guide distal ends 622*a*, 622*b*, respectively, contact the azygos vein wall 916, and until the catheter 602 is pushed to abut the opposing azygos vein wall 918. The first 628*a* and second 628*b* needles can then be deployed, in order to puncture the azygos vein wall 916.

Figure 25:
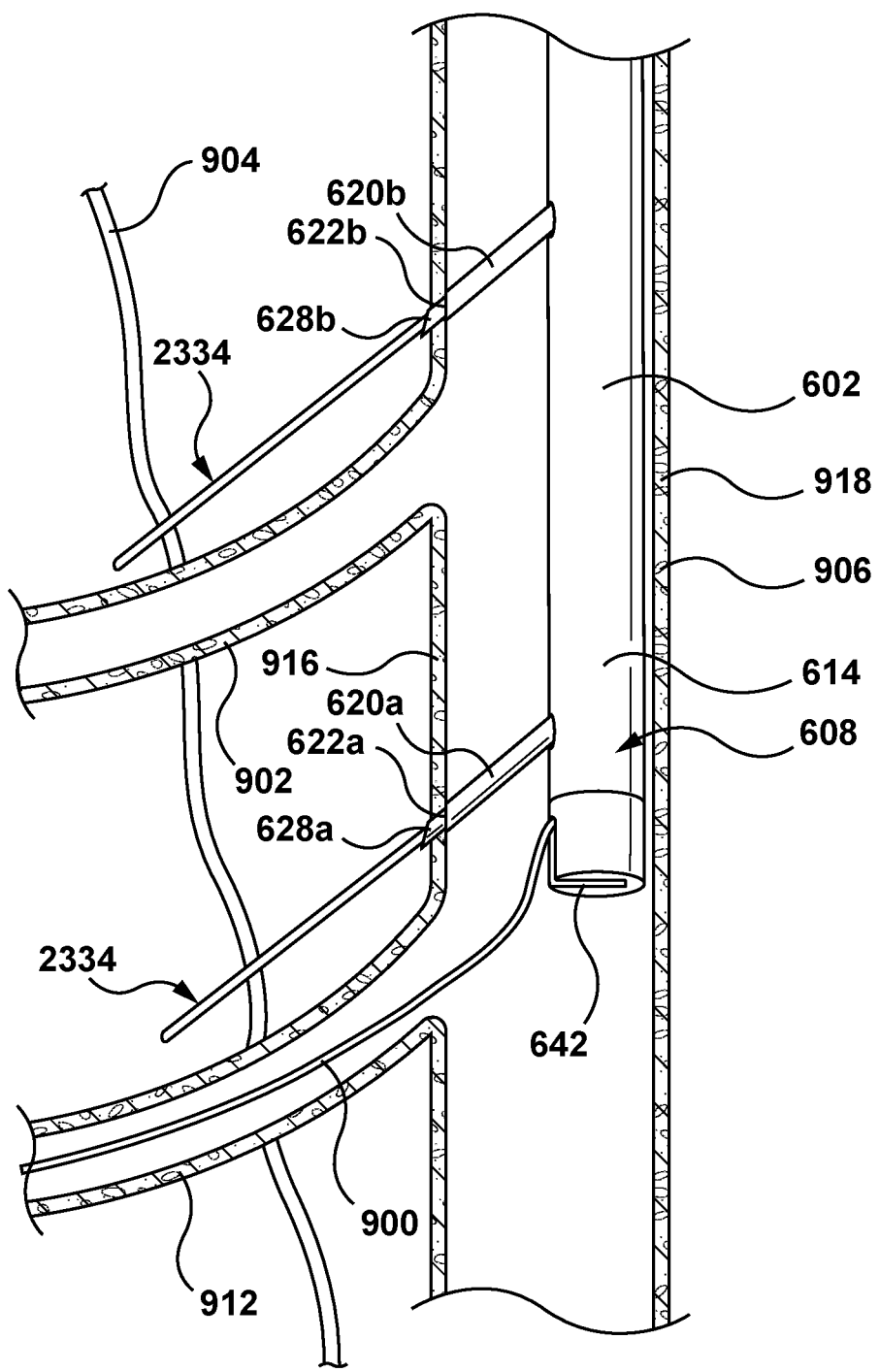
FIG. 25 is a schematic view of the device of FIG. 24, in use.

Optionally, first and second delivery devices can then be deployed from the first 628*a* and second 628*b* needles and can be used to deliver a treatment. For example, referring to FIG. 25, cryogenic energy delivery devices 2334 (as described above with respect to FIG. 24) can be used to deliver cryogenic energy. In some examples, the cryogenic energy delivery devices 2334 can be deployed by a delivery distance of up to 15 mm, in order to treat the GSN 904 from the azygos vein 906.

Alternatively, the first 628*a* and second 628*b* needles themselves can be used to deliver a treatment.

In any of the above examples, various techniques may be employed to avoid puncture of the lungs or other damage to the lungs by the needles or delivery devices. For example, a patient may be instructed to hold their breath briefly during the procedure, to keep the lungs spaced from the device. Alternatively or in addition, various sensors may be employed to detect lung movement (e.g., flow sensors, bioimpedance sensors, pressure sensors). Such techniques are described in US Pub. No. 2018/0110561, PCT Pub. No. WO2018/023132, and PCT Application No. PCT/US2018/066047 (filed Dec. 17, 2018), and will not be described in detail herein.

In any of the above examples, where heat is being used for ablation of the GSN (e.g., by direct thermal treatment or by RF energy treatment), blood flow in the area of the GSN (e.g., blood flow in the azygos vein) may interfere with the treatment by cooling the area. In some such examples blood flow to the area of the GSN may be blocked, or may be directed away from the area of the GSN. For example, a balloon may be inflated in the azygos vein in near the ostium of the intercostal vein. Such techniques are described in US Pub. No. 2018/0110561, PCT Pub. No. WO2018/023132, and PCT Application No. PCT/US2018/066047 (filed Dec. 17, 2018), and will not necessarily be described in detail herein.

In any of the above examples, wherein a treatment fluid is delivered, the fluid can optionally have a viscosity that is or can become relatively high, so that the fluid remains in the area of the GSN. For example, the fluid can have a viscosity that is initially relatively low (e.g., at room temperature or below), but that increases in viscosity at body temperature. Alternatively, the fluid can be provided as two separate components, via two separate lumens in the device. The fluid components may have a relatively low viscosity, but upon being combined, may increase in viscosity.

In any of the above examples, after the ablation treatment is complete, a stimulation may be carried out to confirm that the GSN has been ablated. Such stimulation is described in US Pub. No. 2018/0110561, PCT Pub. No. WO2018/023132, and PCT Application No. PCT/US2018/066047 (filed Dec. 17, 2018), and will not be described in detail herein.

In any of the above examples, the catheter may be advanced through the venous system through a delivery sheath.

In any of the above examples, upon retraction of the device from the patient, a substance may be injected via the device in order to promote healing of the puncture in the vein.

While the above description provides examples of one or more processes or apparatuses, it will be appreciated that other processes or apparatuses may be within the scope of the accompanying claims.

Transvascular Nerve Ablation Embodiments

There are several devices on the market or in development and disclosed in patent applications that are specifically configured for transvascular ablation of nerves for renal denervation for treating hypertension. These devices are designed for use in the renal arteries, and are designed to target nerves that are innervating the renal arteries. Some of the energy modalities that are used in these devices could theoretically be used for GSN ablation from within an intercostal vein. These devices, however, are not suitable for placement in an intercostal vein and for GSN ablation from within an intercostal vein. This disclosure appreciates this and addresses how one or more aspects of these devices and methods of use would need to be modified to perform therapies herein.

For example, a renal artery has a diameter of about 5 mm whereas an intercostal vein has a diameter of about 3 mm. This difference in diameter may require downsizing of device components such as electrodes, catheter shafts or deployable structures such as balloons. Furthermore, the intercostal vein contains significantly lower blood flow than a renal artery. Some renal denervation devices rely on blood flow to cool ablation energy delivery elements so they function properly. Therefore, some devices may need to be modified to consider lower blood flow. For example, a GSN ablation device may require active cooling by irrigating ablation elements or delivering cooling agents to the vessel, or different energy delivery parameters for example lower power for longer duration. Renal denervation devices aim to ablate nerves that reside in the adventitia of the renal artery in an unpredictable pattern around the artery and target ablation zones may only need to be less than 3 mm deep. Conversely, GSN ablation from an intercostal vein aims to ablate a larger nerve that is farther away from the vessel and a target ablation zone may need to be up to 5 mm deep. Furthermore, a renal denervation ablation pattern typically comprises a number of ablations spread apart longitudinally and circumferentially, for example in a helical pattern. Circumferential ablations are generally avoided in renal denervation. Whereas, such patterns deployed in an intercostal vein may miss a target GSN. In transvascular renal denervation a catheter may be advanced from a femoral artery through an aorta and into a renal artery. The size of the aorta and renal artery allow a larger bend radius than the size of an azygos vein and intercostal vein. Thus, a device intended for GSN ablation may need to be more flexible and capable of traversing a smaller bend radius compared to renal denervation devices. Some specific modifications to existing renal denervation devices to make them more suitable for GSN ablation are discussed further herein.

Vessix Vascular has previously disclosed balloon ablation catheters which are described for example in U.S. Pat. Nos. 9,028,472, 9,037,259, 9,174,050, 9,566,114, 9,592,386, 9,072,902, which are incorporated by reference herein and contain many features useful for transvascular ablation of tissue. To be suitable for GSN ablation from within an intercostal vein, modifications to these devices and methods are required.

Figures 26A, 26B:
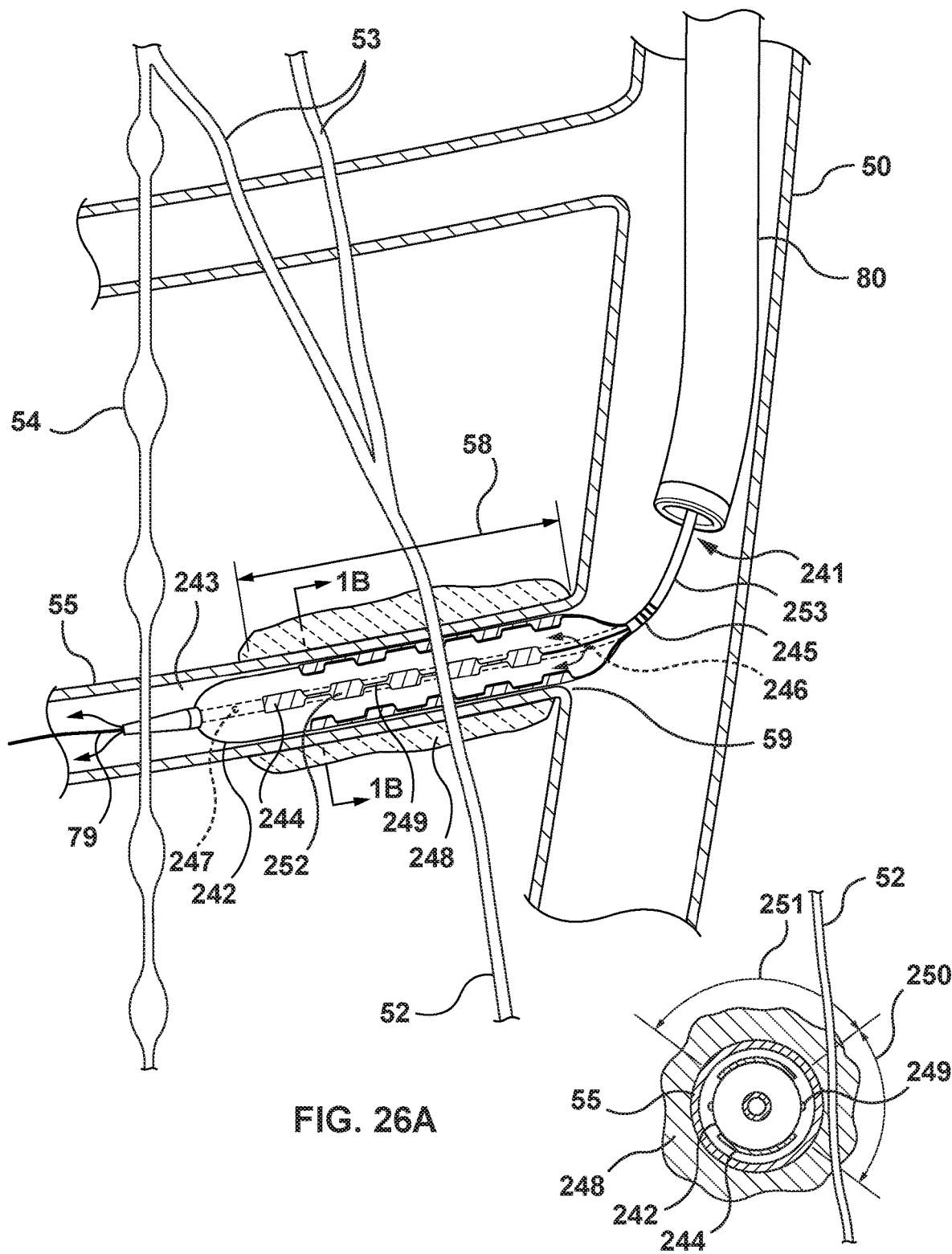
FIG. 26A is a schematic illustration of an ablation catheter having an ablation balloon positioned in an intercostal vein for ablation of a thoracic splanchnic nerve.
FIG. 26B is a cross sectional view of the device of FIG. 26A.

One embodiment of a transvascular ablation catheter 241 for ablating a TSN or GSN from within an intercostal nerve is shown in FIG. 26A. The device 241 may include a catheter extending along a longitudinal axis. An expandable member, for example in the form of a balloon, 242 having an unexpanded state and an expanded state may be coupled to a distal region 243 of the catheter. The expandable member or balloon may have a circumferential treatment zone 248 (e.g., having a length in a range of 12 to 20 mm) extending along the longitudinal axis in the expanded state and surrounding the vessel 55. An electrode assembly 252 comprising a plurality of electrode pads 244 may be mounted to the balloon 242. Each electrode pad assembly may include a substrate supporting first and second electrode pads with each electrode pad having a pair of elongate bipolar electrodes and connected with an electrical trace 249. The electrode pads of each electrode pad assembly may be longitudinally and circumferentially offset from one another. The method may also include expanding the balloon in the intercostal vein so as to electrically couple the electrodes with a wall of the intercostal vein and driving bipolar energy between the electrodes of each bipolar pair so as to therapeutically alter the TSN or GSN within 5 mm of the intercostal vein such that the blood volume of the patient is redistributed for treatment of diseases such as pulmonary hypertension, or heart failure.

Each electrode pad may include a temperature sensor disposed between the electrodes of the pair. The expanding of the balloon may couple the temperature sensors with the wall of the intercostal vein. In some embodiments, the method may further include directing the energy to the bipolar pairs in response to a temperature signal from the temperature sensor so as to heat the wall approximately evenly.

To create an ablation having a depth of 5 mm to target a GSN from an intercostal vein the electrode pads may be cooled to allow greater power to be delivered without desiccating tissue of the vein wall, which impedes ablation depth. The electrodes may be cooled for example, by circulating coolant in the balloon 242. In one embodiment coolant may be injected into the balloon 242 from a coolant injection port 246 at one end of the balloon chamber and the coolant may exit the chamber through an exit port 247 at the opposing end of the chamber and allowed to return through the catheter through an exit lumen.

In another embodiment coolant may be deposited into the blood stream instead of returning through a lumen in the catheter. This embodiment may allow a thinner, more flexible catheter shaft or a larger coolant delivery lumen to increase flow rate of the coolant. A coolant exit port may be smaller than the coolant injection port to allow pressure to increase in the balloon to inflate it. The coolant exit port may be in communication with a lumen that does not pass through the full catheter shaft to the proximal end but instead passes to the distal end of the catheter to deposit the coolant (e.g., normal saline) into the intercostal vein. Optionally the coolant exit lumen may be the same lumen as a guidewire delivery lumen.

Electrode pads may be positioned around the balloon to make a circumferential ablation pattern that is as long as the target ablation zone 58 (e.g., up to 20 mm, about 15 mm, between 12 and 18 mm). For example, as shown in FIG. 26B a balloon with electrode pads mounted to an elongate shaft 253 may have an undeployed state having a diameter of about 1 mm to 2.5 mm and a circumference of about 3.14 mm to 7.85 mm and be expandable to a deployed state having a diameter in a range of about 3 mm to 5 mm and a circumference in a range of about 9.4 mm to 15.7 mm. Electrode pads 244 may be separated by a distance 250 of less than 5 mm (e.g., less than 2.5 mm) and width or arc length 251 in a range of 3 mm to 3.5 mm. Electrode pads 244 may have a length of about 3 to 5 mm each. As shown in FIG. 26A an electrode pad assembly 252 may comprise multiple electrode pads 244 arranged on four separate rows connected together by electrical traces 249, the rows evenly spaced around the circumference of the balloon 242 (e.g., four rows at each 90 degree quadrant). Longitudinally, the pads 244 on one row may be offset from pads of adjacent rows. When the balloon is in its unexpanded state the space between the electrode pads is decreased (e.g., to about 0 to 1 mm) and the adjacent rows interlock with one another. In its expanded state the space 250 between the pads expands due to the expandable balloon 242 to about 2 mm to 5 mm. The balloon 242 may be a compliant material such as latex or a non-compliant material that flexibly folds to contract.

Alternatively, electrode pads may be positioned only on one side (e.g., 50%, 40%, 30%, 25% of the balloon's circumference) to generate a directional ablation pattern that is all toward the same side and of a length of the target ablation zone 58. For a directional ablation catheter a radiopaque marker may be positioned on the distal region of the catheter to indicate radial direction. For example, a radiopaque marker may be asymmetric and positioned on the same side or opposing side as the directional electrode pads to indicate and in use a physician may torque the catheter to aim the radiopaque marker and thus the electrode pads away from the vertebra, which is always toward the GSN. FIG. 26A shows several small electrode pads. Alternatively, the device may have larger and fewer electrode pads, for example two or three directional electrode pads (e.g., 3 to 5 mm long) on the same side of the balloon that span the target ablation zone 58. A gap (e.g., 1 to 3 mm) between electrode pads may facilitate bending of the device to traverse from the azygos vein to the intercostal vein.

Just proximal to the balloon the catheter shaft may comprise a flexible neck 245 that allows the ablation balloon to sit in the intercostal vein's natural orientation. Given the small bend radius at this location a stiff shaft could apply force to the ablation balloon causing it to distort the intercostal vein and reduce predictability of ablation zone. A flexible neck may be made of a softer durometer polymer (e.g., Pebax) and may have a wire coil embedded in the material, which may allow flexible bending while providing pushability.

The electrode(s) that are most proximal are intended to be placed just in the intercostal vein near the ostium. Blood flow through the azygos vein may metabolically cool tissue near it impeding ablation creation. A larger amount of ablation power (e.g., RF) or longer duration may be delivered to this proximal electrode(s) than the rest of the electrode(s) to compensate for the blood flow cooling.

Medtronic/Ardian Inc. has disclosed a catheter for renal denervation having several electrodes mounted along the length of a distal section of a catheter shaft that forms a spiral shape when deployed in a renal artery, for example U.S. Pat. No. 9,125,661, US2012/0143293, the disclosures of which are incorporated by reference herein and contain many features useful for transvascular ablation of tissue. To be suitable for GSN ablation from within an intercostal vein, modifications to these devices and methods are required. This device has electrodes that are quite small and thin which result in ablations no deeper than 3 mm, relies on blood flow similar to renal artery blood flow to avoid tissue charring, electrode spacing and the helical formation of the shaft would create an ablation pattern that is not suitable for GSN ablation because the target nerve could be missed.

Figure 27:
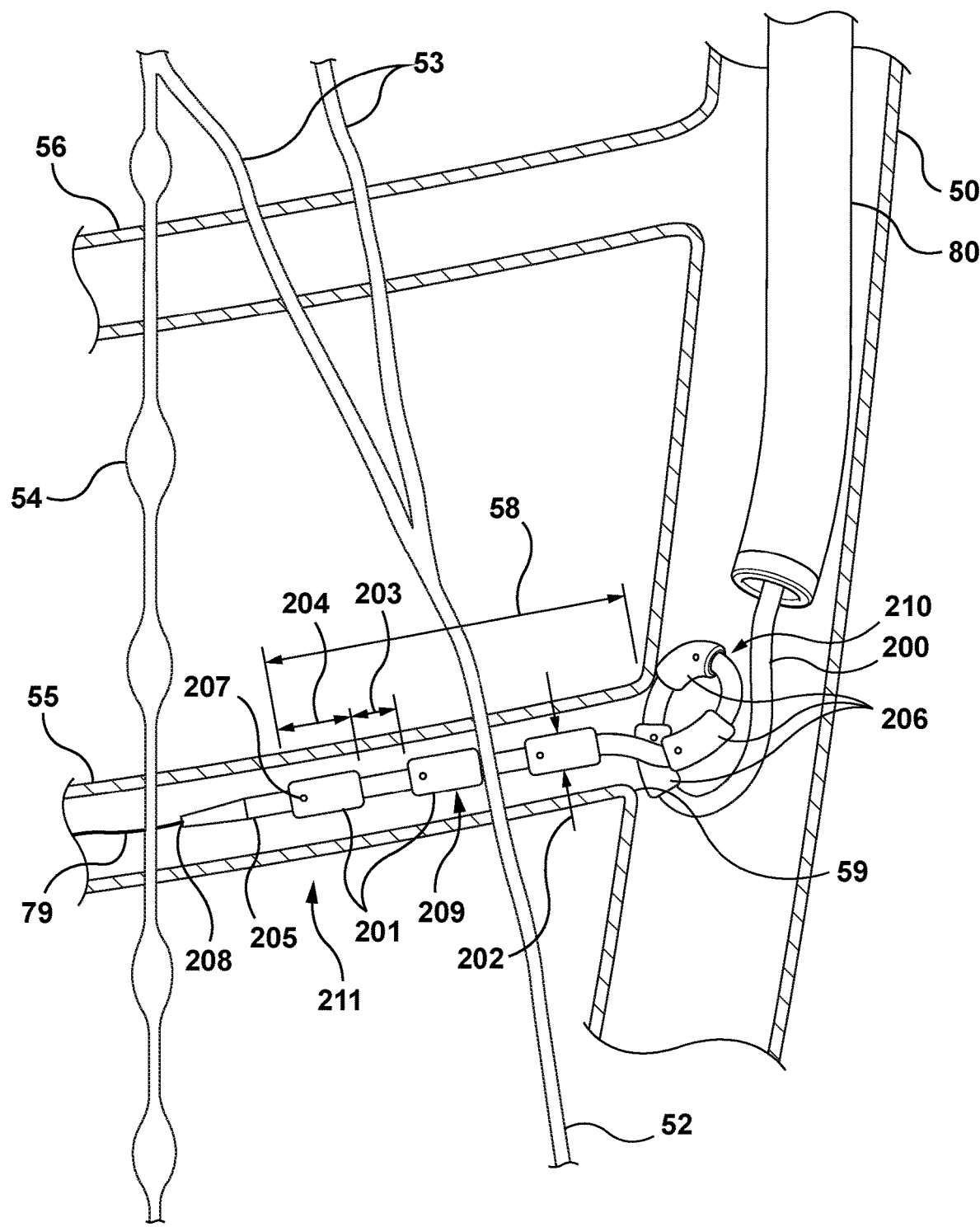
FIG. 27 is a schematic illustration of an ablation catheter positioned in an intercostal vein for ablation of a thoracic splanchnic nerve.

FIG. 27 shows a catheter 200 having an elongated shaft 205 with a proximal region and a distal region and an ablation assembly 211 mounted to the distal region. To modify the catheter 200 to be suitable for GSN ablation, electrodes 201 may be increased in size (e.g., 2 to 3 mm diameter 202), and spacing 203 between electrodes may be decreased (e.g., 2 to 4 mm apart). The length 204 of electrodes may remain in the 1 to 2 mm range or be increased to the 3 to 4 mm range. The helical form of the shaft is not necessary in the intercostal where a straight shaft is preferred when the electrodes have a diameter 202 close to the diameter of the vessel lumen. Electrodes positioned along the straight portion 209 may span a distance of up to 20 mm (e.g., 18 mm, 15 mm) to cover the target ablation zone 58. Electrodes 201 are mounted to a tubular shaft 205. The shaft material in the distal region does not need to be stiff with elastic properties to create a helical preformed shape but instead may be quite flexible to facilitate delivery over the small bend radius from the azygos vein to intercostal vein. Optionally the shaft may have a section 210 that elastically forms a loop shape that is proximal to the straight portion 209 intended to be placed in the intercostal vein 55. The loop shape may comprise electrodes 206 and may be intended to be positioned against the ostium 59, which may ablate tissue around the ostium where a target nerve may reside and also act as a depth stopper to position the straight portion 209 at the correct depth (e.g., 10 to 20 mm) in the intercostal vein 55. RF ablation energy may be delivered in unipolar mode sequentially or simultaneously and optionally may be delivered in bipolar mode as well, to achieve both deep (e.g., 5 mm) ablations and contiguous ablations. Optionally, RF may be delivered with a pulsing waveform that allows surface tissue to cool slightly during pauses while deeper tissue cools slower facilitating ablation depth of the targeted 5 mm. Optionally, the electrodes may be irrigated. For example, the electrodes or sections of shaft between the electrodes may have irrigation ports 207 for delivering fluid such as normal saline. Optionally, the catheter 200 may have a guidewire lumen 208 for delivery over a guidewire 79.

Figure 28:
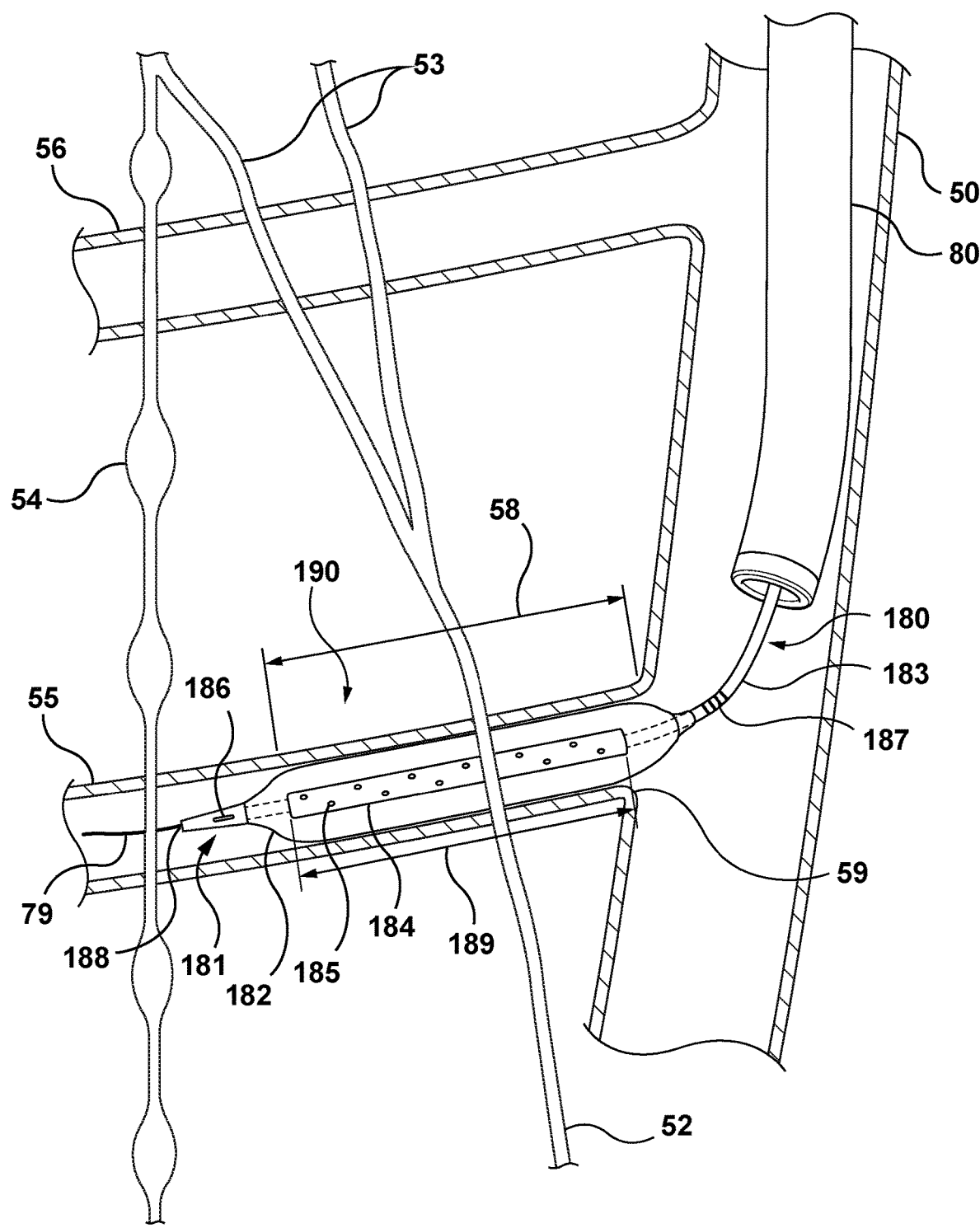
FIG. 28 is a schematic illustration of an ablation catheter having an ablation balloon positioned in an intercostal vein for ablation of a thoracic splanchnic nerve.

Covidien has disclosed a renal denervation catheter and method of use having a deployable balloon with a flexible RF electrode mounted in a spiral configuration to the balloon further comprising apertures that weep liquid such as a cooling saline or anaesthetic, for example US2015/0105659 which is incorporated by reference and contains many features useful for transvascular ablation of tissue. To be suitable for GSN ablation from within an intercostal vein, modifications to these devices and methods are required. An ablation catheter 180 is shown in FIG. 28 positioned in situ. The distal region 181 of the catheter has an ablation assembly 190 wherein an inflatable balloon 182 is mounted to an elongate tubular shaft 183. The dimensions of the balloon may be altered to fit an intercostal vein (e.g., 2.5 to 4 mm diameter in its inflated state) and span a length in a range of 12 to 30 mm. The spiral shape of the electrode of the Covidien device may miss the targeted GSN. The electrode 184 may be altered to be straight and parallel to the axis of the balloon and cover a segment (e.g., 50%, 40%, 30%, 25%) of the balloon's circumference for directional ablation. The electrode 184 may have a length 189 in a range of 12 to 20 mm (e.g., up to 20 mm) capable of creating an ablation the length of the target ablation zone 58. The distal region 181 may have a radiopaque marker 186 that is radially identifiable to confirm the electrode 184 is oriented toward the anterior of the body where the target GSN 52 passes over the intercostal vein 55. Alternatively, one or more electrodes may be positioned around the balloon for circumferential ablation, such as one or more electrodes carried by the balloon and disposed orthogonal to a longitudinal axis of the balloon. The electrode strip 184 may contain Irrigation ports 185 over its surface for weeping of fluid. Fluid apertures may be increased in size to allow greater flow rate. Optionally, the shaft 183 may have a flexible neck 187 within 10 mm proximal of the balloon 182 to allow the distal region 181 to sit well in the intercostal vein. Optionally, the catheter 180 may have a guidewire lumen 188.

Recor Medical has disclosed a renal denervation device and method of use that utilizes ultrasound to ablate tissue around a renal artery, for example US2015/0290427, US2014/0031727, which are incorporated by reference and contain many features useful for transvascular ablation of tissue. The ultrasound transducer is contained in a balloon that centers the transducer in the vessel. The transducer is cylindrical and creates a circumferential ablation around the vessel. Cooling fluid is injected into the balloon to cool the transducer. The ablations made from this device are about 5 mm long.

Ultrasound ablation has a potential to direct energy and is primarily limited by the ultrasonic transducer size in relation to the ablation energy delivery parameters dictating energy dose expressed in terms of frequency, power and time. A frequency between 10 and 30 MHz and power of about 1 to 10 Watts may be required to effectively ablate the nerves in about 2 to 20 seconds from a small transducer (e.g., 5 mm long, 1.5 mm diameter, cylindrical transducer) located in an intercostal vein to ablate a nerve up to 5 mm from the intercostal vein. At these settings significant heating of the ultrasound transducer may be mitigated for example by circulating fluid in an enclosed chamber around the ultrasound transducer, or alternatively by allowing blood flow to contact an open surface biocompatible transducer or a cooling membrane in which local heat generated by the vibrating ultrasound transducer may be used as a part of the controlled ablation cycle. The heat produced by an ultrasound transducer could be dissipated inside the vein and could alter the temperature field around the ultrasound transducer. The resulting effect of combining such conductive heating and active ultrasound ablation may provide an effective way of creating a necrotic region in vicinity of any small vessel. Thermal dissipation is a requirement for proper functioning of an ultrasound transducer and caution should be taken to avoid elevated risk of vessel wall damage. Careful titration of ultrasound energy while taking into account thermal dissipation of local heat constitutes an innovative and more rigorous endovascular ablation approach especially when efficient and collateral damage free ablation of nerves is the procedure goal.

In an alternative embodiment diagnostic and therapeutic ultrasound may be delivered from a transducer extracorporally to the target ablation zone. The vicinity of intercostal veins to the outside of the patient makes feasible the consideration of delivering external ablation through a space between the ribs. The ultrasound transducer may fit in a palm and operate at a frequency window between 3 and 10 MHz by directing energy into the vasculature using a set of anatomical reference points. Specifically, almost 90 degree angle at the ostia of intercostal veins from an azygos vein present reliable references for a Doppler signal visualization of the blood stream normal to the direction of ultrasound pulses emitted by externally placed transducers, which may focus ablative ultrasound energy to the target ablation zone. Thus, ostia locations enable anatomical references for further targeting of the greater splanchnic nerve in between T11 and T10 vertebrae or T9 and T10 vertebrae. Extracorporeal ultrasound may furthermore be used to detect the lung that is in proximity to the target ablation zone and titrate energy delivery to avoid injuring the lung. In one example, ablative energy is delivered when the lung is moved away from the target ablation zone during exhale (e.g., greater than a threshold distance of 10 mm for example) and decreased or paused when the lung is close to the target ablation zone (e.g., within the threshold distance of 10 mm for example).

Figure 29:
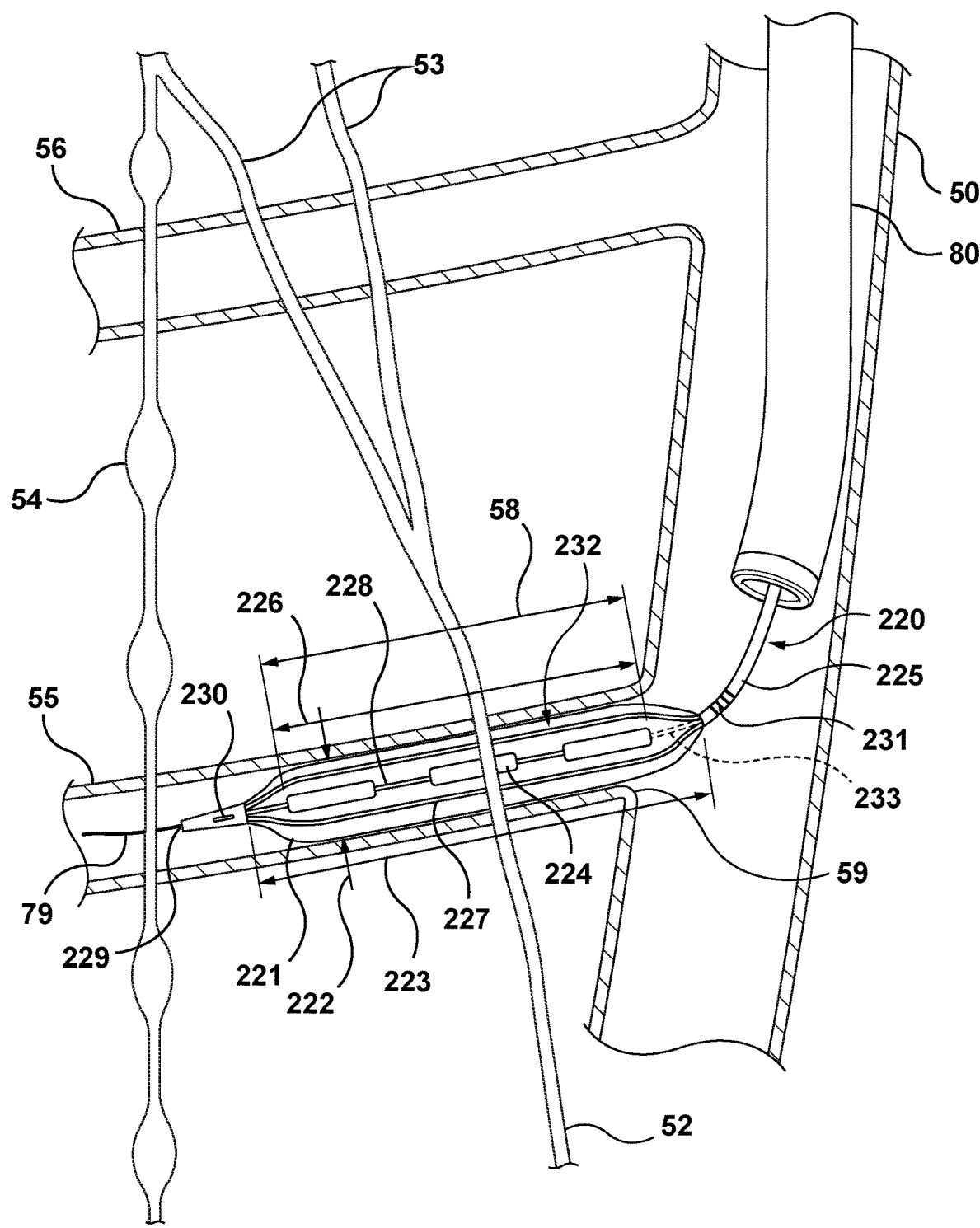
FIG. 29 is a schematic illustration of an ultrasound ablation catheter positioned in an intercostal vein for ablation of a thoracic splanchnic nerve.

FIG. 29 shows a catheter 220 having an elongate shaft 231 with a proximal region and a distal region and an ablation assembly 232 mounted to the distal region. To modify the device for GSN ablation from within an intercostal vein an ultrasound ablation catheter 220 has an inflatable balloon 221 which may have a geometry suitable for expansion in an intercostal vein (e.g., outer diameter 222 in a range of 3 to 4 mm in its inflated state) and a length 223 in a range of 12 to 30 mm. Within the balloon 221 multiple ultrasound transducers 224 are positioned on a shaft 233 centered in the balloon 221. The transducers 224 may be placed serially spanning a length 226 that is in a range of 12 to 20 mm to generate an ablation of a similar length capable of creating an ablation the length of the target ablation zone 58. Due to the small diameter of the intercostal vein the reduced balloon size may risk contacting the transducer or getting over heated by the transducer, which may rupture the balloon or reduce efficacy of the ablation. To remedy this risk struts or protrusions 227 may be positioned between the transducer and balloon. The struts 227 may be for example polymer strands elastically pre-shaped to radially expand away from the transducers 224. To make a longer ablation to span the targeted ablation zone multiple transducers may be incorporated (e.g., three 4 mm long transducers) and spaced apart with flexible gaps 228 between them to facilitate traversing the small bend radius from the azygos vein to intercostal vein. For example, shaft 225 may be a braid reinforced polyimide tube with an optional guidewire lumen 229 for delivery over a guidewire 79 and carry electrical conductors that energize the transducers 224. The ultrasound transducers 224 may be cylindrical for producing circumferential ablation around the target vein. Alternatively, the ultrasound transducers may be flat or hemicylindrical to produce an ablation that is a partial segment of the circumference of the vein and a radially identifiable radiopaque marker 230 may be positioned on the distal region allowing a user to orient the direction of ablation toward the patient's anterior where the GSN passes over the vein 55. Optionally, the ultrasound transducer may be configured to image as well as ablate and the imaging function may be used to assess nearby structures such as the lung, vertebra, ribs. Imaging ultrasound may be used to confirm the transducer is aiming toward the lung, which is the direction of the target GSN. Optionally, the shaft may have a flexible neck 231 within 10 mm proximal of the balloon 221 to allow the distal region to sit well in the intercostal vein.

In an alternative embodiment of an ultrasound ablation catheter, the catheter can be composed of an active ultrasound transducer and an inflatable reflector balloon, which may be on the same catheter or alternatively be on separate catheters. The reflector balloon may have an inflated diameter in a range of 2.5 to 4 mm and on its proximal surface have a shape such as a concave curvature that focuses reflected waves on to the target ablation zone. The reflector balloon is located distal to the transducer and is inserted in the narrower intercostal vein, while the ultrasound transducer remains in the larger azygos vein. The ultrasound transducer may be exposed to blood flow in the azygos vein or alternatively may be contained in a chamber in an inflatable balloon filled with coolant (e.g., circulating coolant such as sterile water or saline). The ultrasound energy is directed toward the distal reflector balloon and reflected and focused into tissue surrounding the splanchnic nerve. The advantage of this approach is that an active ultrasound transducer can be made larger and is not required to go through the sharp turn from azygos to intercostal vein. A second advantage is that several intercostal veins can be used to target ablation with the same catheter.

Figure 30A:
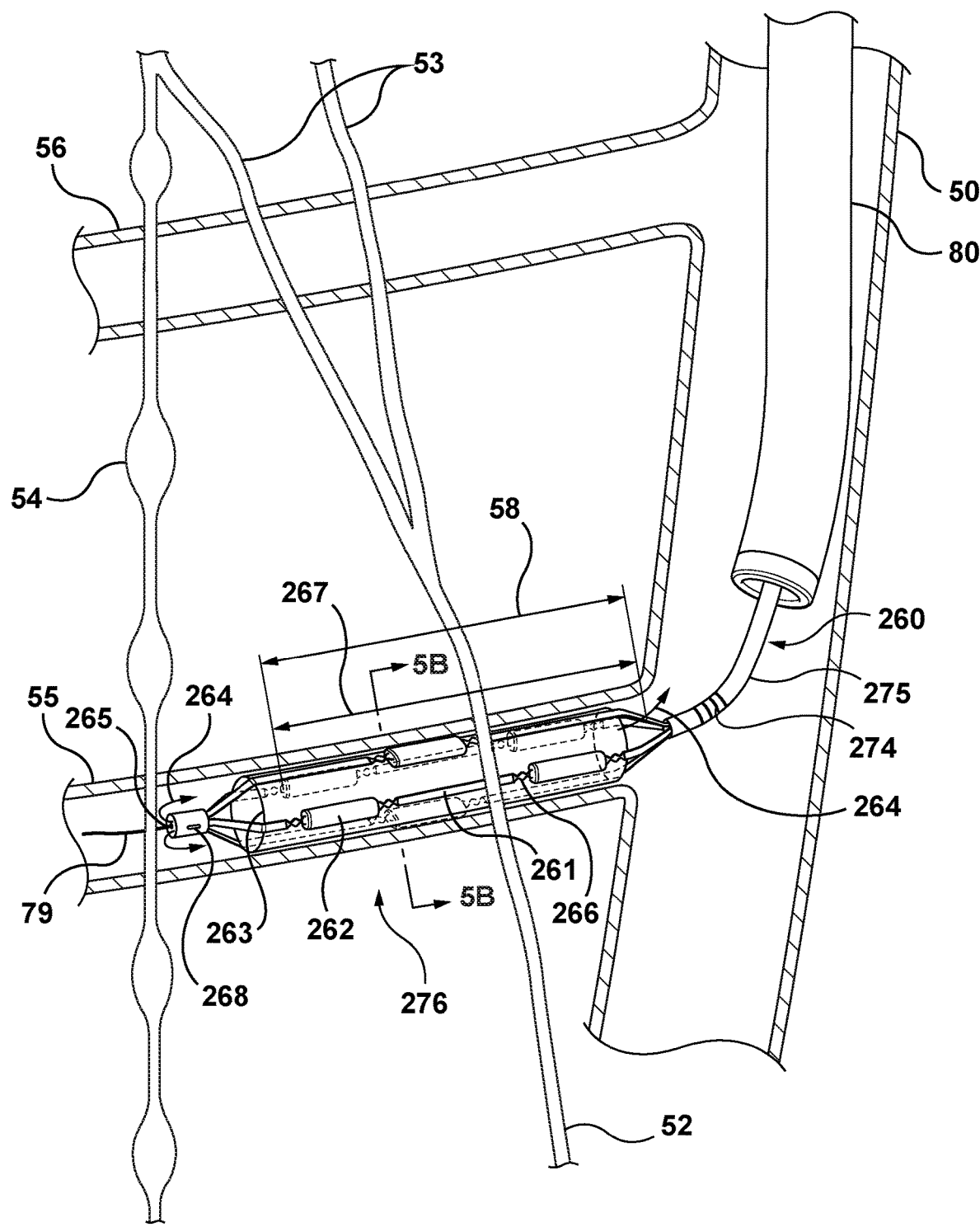
FIG. 30A is a schematic illustration of an ablation catheter having an ablation balloon positioned in an intercostal vein for ablation of a thoracic splanchnic nerve.
Figure 30B:
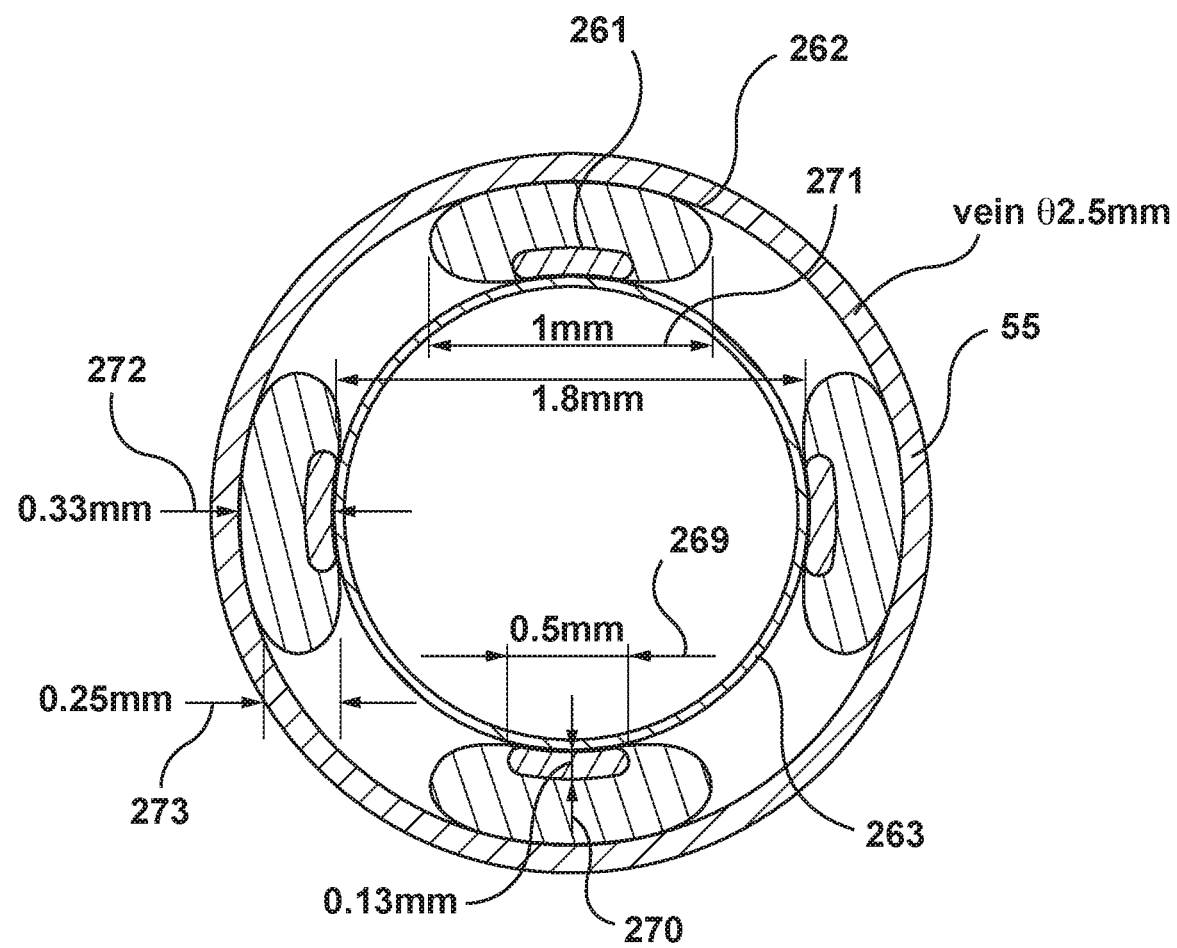
FIG. 30B is a cross section of the device shown in FIG. 30A.

Renal Dynamics has disclosed a renal denervation device and method of use that deploys RF electrodes (e.g., 8 RF electrodes spaced apart in quadrants) mounted to radially expandable struts forming a basket to ablate tissue around a renal artery and also includes a non-occluding membrane intended to isolate blood, minimizing heat loss and enabling deeper tissue ablation, for example EP2934357, WO2016132340, the disclosures of which are incorporated by reference herein and contain many features useful for transvascular ablation of tissue. The device relies on blood flow in a renal artery to provide thermal properties such as electrode cooling for creating ablations. Potentially in some patients there could be sufficient blood flow in an intercostal to cool electrodes however it would be much less than in a renal artery and alternative energy delivery parameters may compensate for the lower blood flow. For example, a pulsed RF waveform that allows surface tissue to cool during amplitude pauses may generate an effective 5 mm deep ablation. FIGS. 30A and 30B show an RF ablation catheter 260 having an elongated shaft 275 with a proximal region and a distal region, and an ablation assembly 276 mounted to the distal region. The ablation assembly 276 is made of a basket of elastic struts 261 (e.g., 3 or 4 rows of struts) each having at least one electrode 262 mounted to it in a configuration that allows the basket to have a contracted delivery state having a diameter of about 1.7 mm and an expanded ablation state having a diameter in a range of about 2.5 mm to 4 mm. A non-occluding, radially expandable, tubular membrane 263 may be electrically insulative and connected to (e.g., positioned over) the struts 261 with the electrodes 262 on the outer surface of the membrane. The membrane 263 may prevent electrical RF energy from shunting through the blood so it is concentrated through the vessel wall to the target ablation zone. Optionally, additional electrode cooling may be achieved through injecting a coolant 264 such a saline through the lumen of the non-occluding membrane to cool electrodes with convection. Since blood flows in the intercostal vein in a direction that is from the distal end of the device toward the azygos vein, coolant may be injected through a coolant delivery port 265 that is at the distal end of the basket so it flows in the same direction as the blood flow. The dimensions of the struts making the basket may be modified to fit a smaller vessel, for example having a maximum diameter in a range of 3 to 4 mm. The struts may comprise narrowed sections 266 between mounted electrodes (e.g., at the same longitudinal distance) that have greater flexibility than the rest of the struts to facilitate bending when delivering over a small bend radius from the azygos vein to intercostal vein. The length 267 of the basket and position of the electrodes may be shortened to generate an ablation along the targeted ablation zone 58 that is in a range of 12 to 20 mm long (e.g., 15 mm long). The electrodes may be arranged to create a circumferential ablation along the full length of the targeted ablation zone. Alternatively, electrodes may be mounted only on one or two struts of the basket to ablate only a segment (e.g., 50%, 40%, 30%, 25%) of the vessel circumference for directional ablation. A radiopaque marker 268 that identifies radial direction of the basket may be positioned on the catheter's distal region (e.g., on the struts, as the struts, using the position of the electrodes which may be radiopaque, on the catheter shaft near the basket). As shown in FIG. 30B, a cross section of FIG. 30A, struts 261 may have a width 269 of about 0.5 mm and thickness 270 of about 0.13 mm. Electrodes 262 may have a width 271 of about 1 mm and a maximum thickness 272 of about 0.33 mm tapered to narrower thickness 273 at the edges of about 0.25 mm. Electrode length may be about 3 to 5 mm. Optionally, the shaft may have a flexible neck 274 within 10 mm proximal of the balloon basket to allow the distal region to sit well in the intercostal vein.

Dual Electrode Embodiments

The disclosure that follows is generally related to systems, devices, and methods for transvascular ablation of target tissue. The devices and methods may, in some examples, be used for splanchnic nerve ablation for treatment of heart failure. For example, the devices disclosed herein may be advanced endovascularly to a target vein in the region of a thoracic splanchnic nerve (TSN), such as a greater splanchnic nerve (GSN) or a TSN nerve root. Any of the disclosure herein related to nerve ablation may apply to the following disclosure, and is incorporated by reference into the disclosure that follows.

Dual Electrode Catheter

Figure 31:
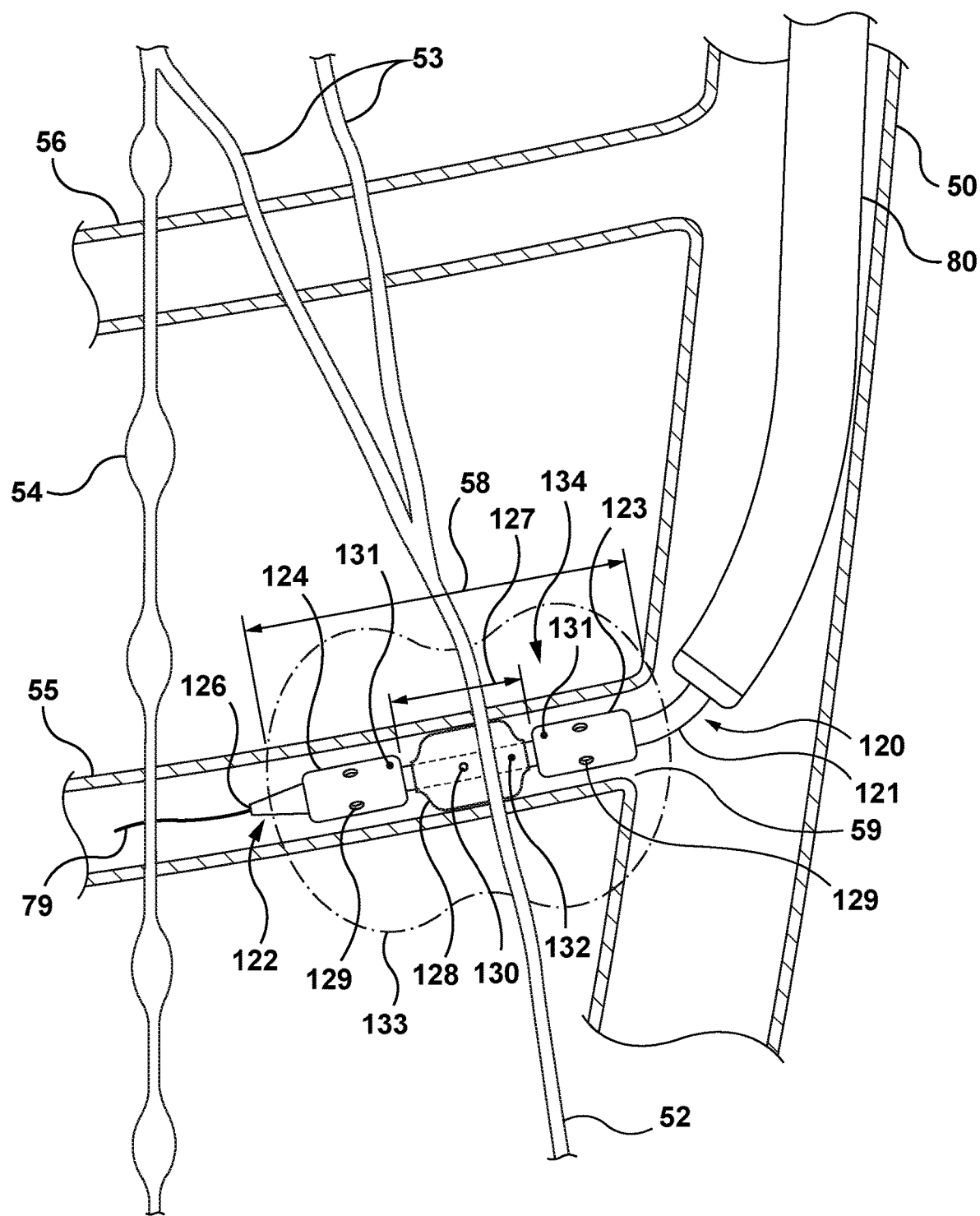
FIG. 31 is a schematic illustration of an ablation catheter positioned in an intercostal vein for ablation of a thoracic splanchnic nerve.

FIG. 31 illustrates an exemplary embodiment of an ablation device in an exemplary position for use. In FIG. 31, device 120 is placed in an exemplary location for transvascular ablation of a target nerve (e.g., GSN 52, GSN roots 53, TSN) from a small vein (e.g., T11 intercostal vein 55, T10 intercostal vein 56, T9 intercostal vein, lower three intercostal veins) is shown. The device 120 includes an elongate shaft 121, a catheter proximal portion (not shown) intended to remain out of the patient in use and may be manipulated by a physician, and a catheter distal portion 122 comprising at least two ablation elements (which may also be referred to herein as ablation members) including a proximal electrode 123 and a distal electrode 124, and an occlusion element 128 there between. Any of the occlusion elements herein may also be referred to as an occlusion member.

In the example shown, the catheter 120 includes a guidewire lumen (not shown) extending therethrough, and the catheter distal portion 122 includes a guidewire exit port 126 positioned at or near the distal end of the distal section 122, so that the catheter 120 can be advanced into the venous system along a guidewire 79. The catheter may be delivered through a delivery sheath 80. In some examples, the elongate shaft 121 can include a braided shaft to facilitate torqueability (i.e., transmission of torque from the catheter proximal portion to the catheter distal portion 122), particularly over a tortuous delivery path. In alternative examples, the guidewire lumen and exit port 126 may be omitted, and the catheter may be advanced into a patient's cardiovascular system (e.g., into a vein or artery) without the aid of a guidewire. For example, a catheter may have a deflectable distal tip controllable by an actuator on a handle on the proximal portion that controls tension of a pull wire connected to the deflectable distal tip that can bend (e.g., a 90 degree deflectable bend with a bend radius in a range of 6 to 15 mm) to facilitate advancement from a first vein into a second vein or an ablation catheter may be advanced through a delivery sheath that may be advanced over a guide wire to a target vessel wherein the guidewire may be removed before advancing the ablation catheter.

The ablation elements 123 and 124 shown in FIG. 31 comprise electrodes that are each connected their own independent conductor that passes through the catheter shaft 121 to the proximal region of the catheter where they are connectable to an energy delivery console, which may operate the two electrodes in bipolar RF mode. Each electrode may have dimensions suitable to fit into a small vessel (e.g., a T10 intercostal vein 56, a T11 intercostal vein 55, a T9 intercostal vein, a human's lower three intercostal veins) and for delivering RF ablation energy. Each electrode 123 and 124 may be cooled with irrigation and optionally comprise irrigation exit ports 129 on their sides or ends in fluid communication with at least one irrigation lumen (not shown) passing though the catheter shaft 121 to the proximal region of the catheter where it is connectable to an irrigation fluid supply. Optionally separate irrigation lumens may be present to separately supply irrigation to each electrode. Separate irrigation lumens may facilitate more precise control of irrigation flow rate to each electrode. The irrigation exit ports 129 may have a diameter of about 0.020"+/− 0.005". Alternatively, irrigation of the electrodes may be closed looped and contained within the catheter instead of delivering irrigation fluid through exit ports into the blood stream. An embodiment with closed-loop irrigation may include at least one irrigation fluid delivery lumen that delivers fluid to a chamber within each electrode and at least one return lumen that returns the fluid to the proximal region of the catheter. Each electrode 123 and 124 may have a length in a range of 3 to 5 mm (e.g., 4 mm) and outer diameter in a range of 1.5 to 3 mm (e.g., 2 mm). The distance 127 between the electrodes may be in a range of 3 to 6 mm (e.g., 4.5 mm). This combination of lengths of the electrodes and distance between them along with suitable ablation energy profiles disclosed herein and an occluding balloon 128 and electrode irrigation may be suitable for creating a desired ablation size capable of covering the target region 58 including a length of up to 20 mm and depth of up to 5 mm. Each electrode 123 and 124 may have an associated temperature sensor 131 (e.g., thermocouple or thermistor electrically connected to conductors passing through the catheter shaft 121 to the proximal region of the catheter and connectable to the ablation energy console) in or on the electrodes, which may be used to control energy delivery. Optionally, the electrodes may be made with a radiopaque material such as platinum iridium.

The device 120 further comprises an inflatable occlusion member 128, in this embodiment ablation balloon 128, positioned on the catheter shaft between the proximal electrode 123 and distal electrode 124. The balloon may be made from a membrane (e.g., compliant, semi-compliant, or non-compliant balloon) and made with techniques known in the medical device industry for making catheter balloons. The membrane may be sealed to the shaft at the balloon's proximal and distal ends and define a chamber within the membrane. A balloon inflation port 130 is positioned within the chamber and is in fluid communication with an inflation lumen (not shown) passing through the catheter shaft 121 to the proximal region of the catheter where it is connectable to an inflation fluid supply (e.g., gas or liquid delivered with a pressurizing device such as a syringe or pump). A temperature sensor 132 may be positioned in the chamber within the balloon 128, which may be used to monitor inflation fluid temperature. The balloon in its uninflated state may have a diameter in a range of 1.5 to 2 mm and in its inflated state may have a diameter in a range of 3 to 5 mm or approximately the size of the target vessel lumen. Optionally, in use a first volume of inflation fluid may be injected into the balloon when placed in a first vessel (e.g., intercostal vein) to increase the balloon's diameter to occlude the first vessel, and a second volume of inflation fluid may be injected when placed in a second vessel (e.g., azygos vein) to increase the balloon's diameter to occlude the second vessel. The balloon may function to occlude blood flow which may provide a more stable ablation environment (e.g., thermal and electrical properties) around the electrodes, to stop the target vessel from shrinking when heated which may provide a more stable ablation environment and maintain vessel patency, or may direct ablation energy into the tissue.

Figure 32A:
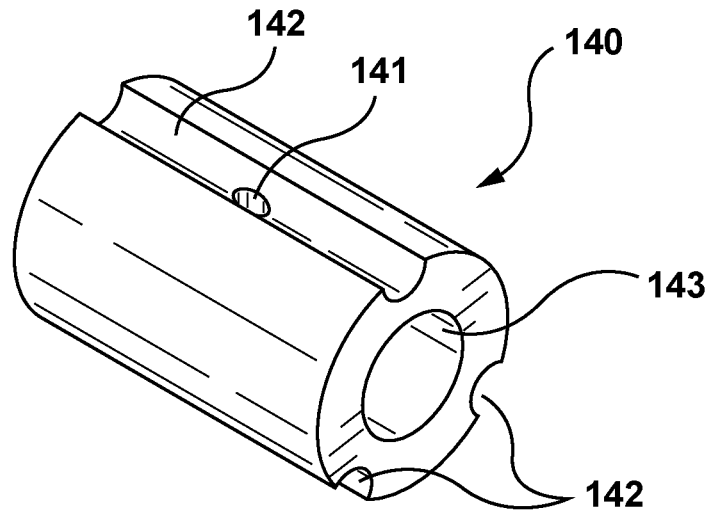
FIGS. 32A and 32B are schematic illustrations of alternative embodiments of electrodes having fluid escape features.
Figure 32B:
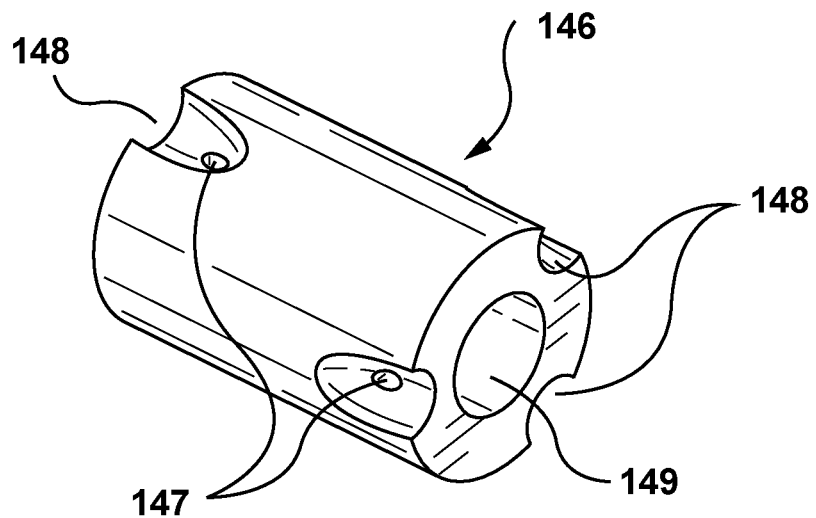

The irrigation ports 129 may be positioned on the sides of the electrodes 123 and 124. Optionally, the irrigation ports may have features that allow irrigation fluid to continue to flow even if the vessel shrinks around the electrodes. FIGS. 32A and 32B are schematic illustrations of single electrodes not connected to a catheter, which may optionally replace either of the proximal and distal electrodes 123 and 124 of FIG. 31 or any other embodiment herein. As shown in FIG. 32A an alternative embodiment of an electrode 140 may comprise an irrigation port 141 positioned in a channel 142 that spans the length of the electrode 140. Multiple ports and channels may be positioned around the catheter, for example three ports and channels as shown. The electrode 140 comprises a central lumen 143 for mounting to the shaft 121 over an irrigation lumen, electrical conductors for ablation energy, or temperature sensors (not shown). FIG. 32B shown an alternative embodiment of an electrode 146 (which may be used as any ablation element or ablation member herein) may comprise an irrigation port 147 positioned in a scallop 148 that spans only a portion of the length of the electrode 146. Multiple ports and scallops may be positioned around the catheter, for example, six ports and channels as shown, although more or fewer may be used. The electrode 146 comprises a central lumen 149 for mounting to the shaft 121 over an irrigation lumen, electrical conductors for ablation energy, or temperature sensors (not shown).

An ablation energy delivery console (not shown) may be connectable to the catheter 120 to delivery radiofrequency (RF) electrical current to one or more of the electrodes 123, 124 to create independent ablations simultaneously or independently to create an overall large ablation spanning the target zone 58. Alternatively, smaller ablations may be made by energizing only one of the electrodes in which case it may be desired to deliver a nerve stimulation signal from the electrode to confirm the target nerve is within the ablation zone of the single electrode. When both electrodes 123 and 124 are energized simultaneously they may be energized with in-phase voltages or currents and the two RF sources energizing each electrode may be floating with respect to each other. Energy delivery parameters such as temperature set point for temperature controlled energy delivery, or power set point for constant power energy delivery can be set to the same values and automatically modified based on response due to differing blood flow rates or impedance, in particular since the proximal electrode 123 may experience greater blood flow from the azygos vein nearby. For example, if the temperature increase during energy delivery is slower for the proximal electrode, that may be an indication of increased convective cooling provided by blood flow. The power delivery algorithm can recognize the slow temperature increase and increase the power set point for the proximal electrode, or a higher temperature set point or duration of energy delivery may be used to compensate. Examples of energy delivery parameters for a constant power mode may have a power set point in a range of 5 to 10 W (e.g., 7 to 8 W); a maximum irrigated electrode temperature to avoid tissue charring may be in a range of 60 to 95 C (e.g., about 85 C); a maximum temperature in the balloon chamber may be less than 100 C; and a duration in a range of 60 s to 240 s.

An alternative energy delivery protocol may include a two-channel combined monopolar-bipolar RF ablation configuration. This configuration comprises delivering RF energy with different voltages to each electrode 123 and 124 in monopolar mode communicating with a dispersive electrode. The difference in applied RF voltages creates a partial bipolar mode effect with energy going from the higher-voltage electrode to the one which has lower voltage associated with it. This results in an intended monopolar-bipolar combo mode. It would be preferable, therefore, that the two sources driving the electrodes have a common ground. This configuration of energy delivery in combination with the electrode size, spacing and balloon of the catheter 120 may have an effect of generating an ablation that spans the target ablation zone 58 and depth of 5 mm to ablate a target nerve in the ablation zone. As described above the energy delivery parameters such as temperature or power set points may be automatically adjusted to compensate for the different thermal and electrical environments of the proximal and distal electrodes.

Optionally, an energy delivery algorithm may monitor for pooling saline that is starting to boil (e.g., via rapid fluctuations in impedance and/or temperature). If boiling is detected (e.g., with a temperature sensor), then the algorithm may reduce power and/or temporarily shut off power and wait a predetermined time or wait until temperature drops below some threshold (e.g., 95 C) then ramp up power again. The algorithm may identify a maximum power where boiling was previously detected and use that value to limit the max power during the resumed power period. Alternately the algorithm may choose a lower temperature set point than the target temperature that previously resulted in the boiling.

The console may also control electrode irrigation by turning an irrigation fluid pump on and off so irrigation is occurring while RF is delivered. The flow rate of the irrigation may be set to a constant rate (e.g., about 2 mL/min). Alternatively, a greater flow rate may be delivered to the distal electrode since it has less cooling from blood flow than the proximal electrode when used as shown in FIG. 31. Alternatively, flow rate may be higher to an electrode that has a higher temperature to power ratio.

Methods of using the device 121 include versatile positioning and energy delivery profiles which may be valuable for use in a range of anatomical variability. In particular when using the device for GSN ablation from within intercostal veins a method of use may comprise ablating a first target region from within a lowest intercostal vein (e.g., T11 intercostal vein) followed by ablating a second target region from within a second lowest intercostal vein (e.g., T10 intercostal vein). A first method of use may comprise fully delivering both electrodes 123 and 124 into the lowest intercostal vein 55 such that the proximal end 129 of the proximal electrode 123 is aligned with the ostium 59 where the intercostal vein connects to the azygos vein 50, performing an ablation procedure, repositioning the distal region 122 to the second lowest intercostal vein 56, and performing a second ablation procedure.

In some patients one or more target intercostal veins may be too narrow or tortuous to deliver both electrodes 123 and 124 fully into the target vein. In this scenario a second method of use may comprise inserting only a distal electrode 124 into the target vein and creating a shorter ablation compared to the first method of use. It may or may not be possible to deliver both electrodes into a second or third lowest intercostal vein and ablate the full target regions. Optionally, when ablating with only the distal electrode 124 in an intercostal vein ablation energy may be delivered only to the distal electrode 124 wherein an electrical circuit is competed by a dispersive electrode optionally elsewhere on the catheter or on the patient's skin. Alternatively, the proximal electrode 123 may complete the circuit in a bipolar mode wherein the proximal electrode is expected to be positioned within the azygos vein where greater blood flow cools the proximal electrode and vessel. The occlusion balloon 128 may be inflated to direct blood flow away from the ostium.

Figure 33:
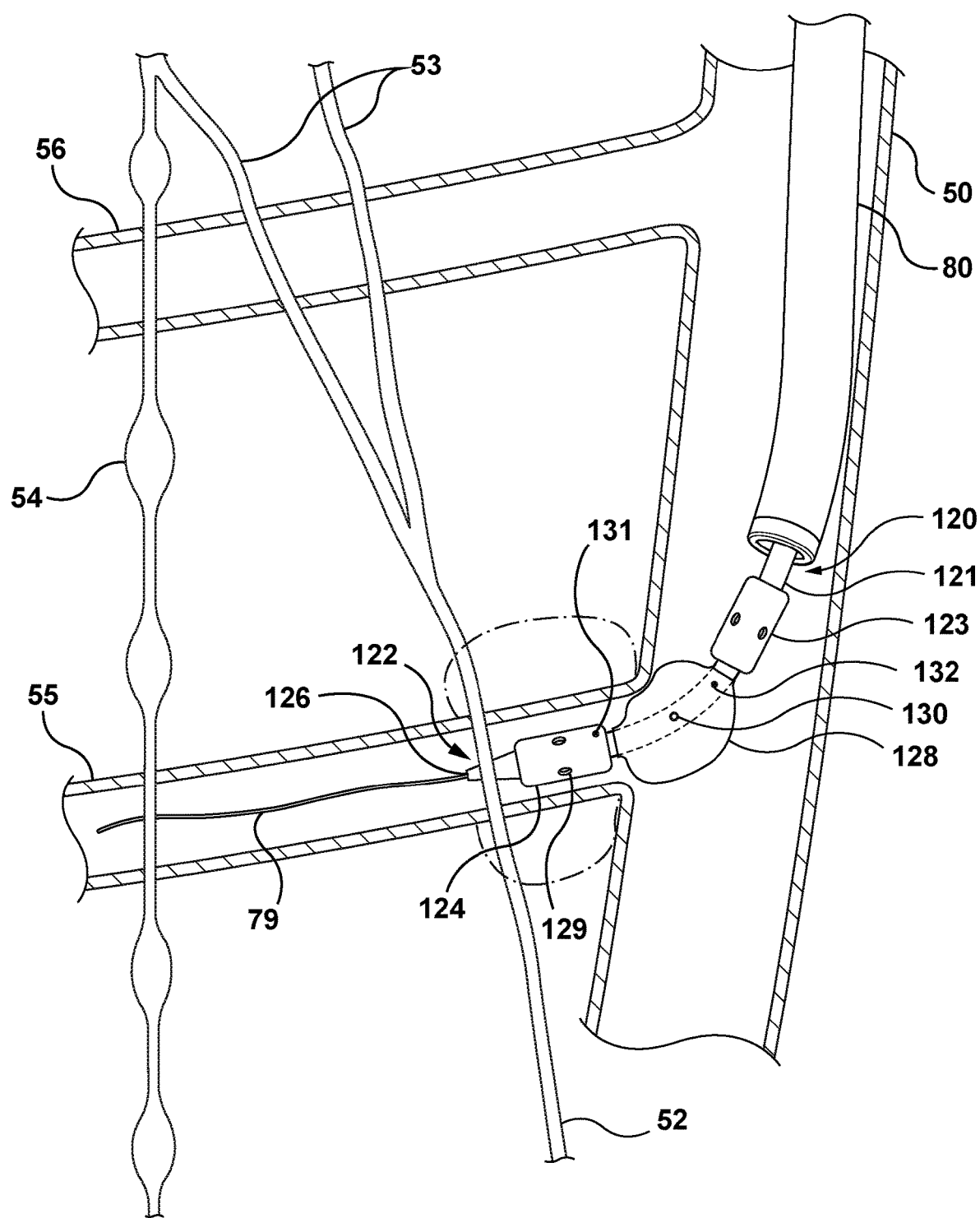
FIG. 33 is a schematic illustration of the ablation catheter of FIG. 31 positioned at an ostium of an intercostal vein for ablation of a thoracic splanchnic nerve.

A third method of use may include conducting the steps of the first method of use and additionally moving the device to a position as shown in FIG. 33 wherein the distal electrode 124 is in the intercostal vein 55 (or other intercostal vein) and the balloon 128 is inflated to direct azygos vein blood flow away from the ablation zone, and creating further ablations around the intercostal veins and within 10 mm (e.g., 6 mm) of the ostium 59. Blood flow in the azygos vein 50 may cool tissue near the ostium that is within the target ablation region 58 potentially impeding an efficacious ablation size.

Any of the methods of use described herein may further comprise a visualization step to determine the location of the device in the target nerve. Medical imaging technology such as fluoroscopy may be used to image the device, in particular radiopaque aspects of the device such as the proximal and distal electrodes 123 and 124 in relation to the patient's vasculature. A radiopaque contrast agent may be injected into the patient's blood stream (e.g., via the delivery sheath 80, guidewire lumen and exit port 126, or electrode irrigation ports 129) to facilitate fluoroscopic imaging.

Dual Electrode Catheter with Recessed Electrodes

Figure 34A:
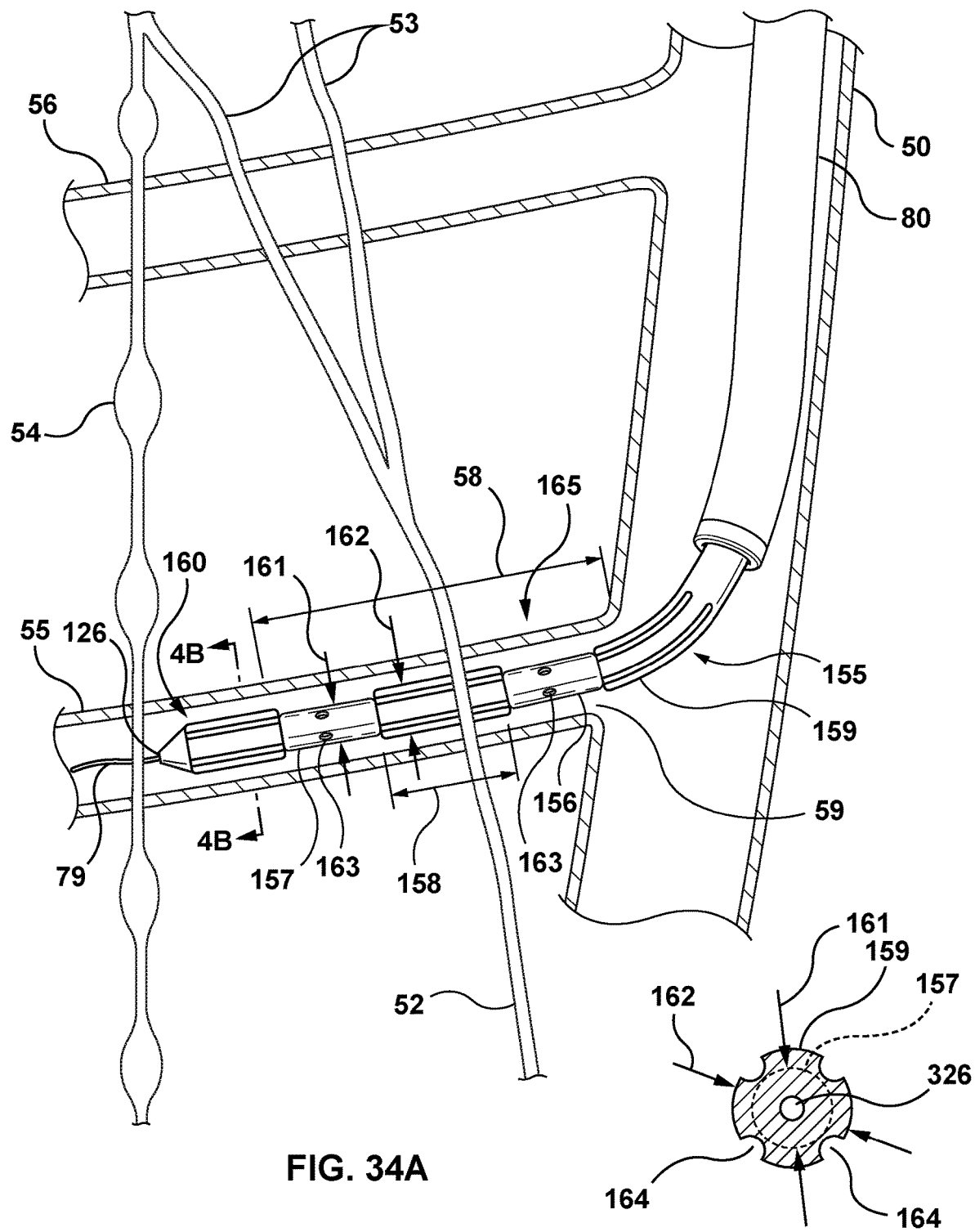
FIG. 34A is a schematic illustration of an ablation catheter positioned in an intercostal vein for ablation of a thoracic splanchnic nerve.
Figure 34B:
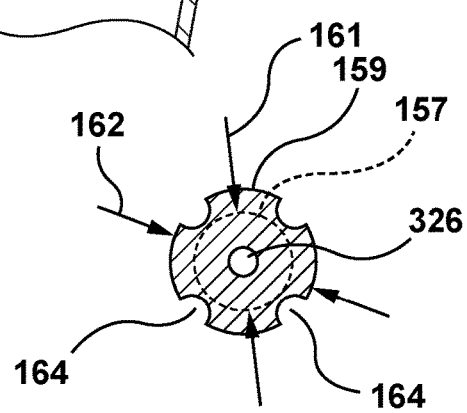
FIG. 34B is a sectional view of the ablation catheter shown in FIG. 34A.

In an alternative embodiment of a catheter 155 for transvascular ablation (e.g., of a TSN or GSN from an intercostal vein) is shown in FIGS. 34A and 34B. This catheter 155 has at least one electrode for delivering ablation energy or nerve stimulation signals. As shown the catheter 155 has two electrodes: a proximal electrode 156 and a distal electrode 157 separated by a distance 158. The electrodes 156 and 157 are mounted to a shaft 159 of the distal region 160 of the catheter and have a diameter 161 that is less than the diameter 162 of the shaft 159 of the distal region. For example, for transvascular ablation from within an intercostal vein the electrode diameter 161 may be in a range of 1.5 to 2.5 mm, the shaft diameter 162 may be in a range of 2 to 3 mm, and the electrode diameter 161 may be less than the shaft diameter 162 by 0.2 to 1 mm. Delivering ablation energy from within a small vessel (e.g., less than 4 mm) may result in heating the vessel wall, which may cause it to shrink. By recessing the electrodes' surface from the shaft surface the shaft 159 of the distal region 160 may hold the vessel wall away from the electrode surface and maintain a gap, which may provide a more consistent thermal and electrical environment during energy delivery, which in turn may improve safety and efficacy of energy delivery. Each electrode 156 and 157 may be cooled with irrigation and optionally comprise irrigation exit ports 163 on their sides in fluid communication with at least one irrigation lumen (not shown) passing though the catheter shaft 159 to the proximal region of the catheter where it is connectable to an irrigation fluid supply. Electrode irrigation cools the electrodes during energy delivery so they can deliver greater ablation power, which may be needed to ablate a depth of up to 5 mm from the vessel wall (e.g., for GSN ablation). Optionally separate irrigation lumens may be present to separately supply irrigation to each electrode. Separate irrigation lumens may facilitate more precise control of irrigation flow rate to each electrode. The irrigation exit ports 163 may have a diameter of about 0.020"+/−0.005". Alternatively, irrigation of the electrodes may be closed-looped and contained within the catheter instead of delivering irrigation fluid through exit ports into the blood stream. An embodiment with closed-loop irrigation may include at least one irrigation fluid delivery lumen that delivers fluid to a chamber within each electrode and at least one return lumen that returns the fluid to the proximal region of the catheter. In embodiments having open-looped irrigation as shown in FIGS. 34A and 34B the shaft 159 of the distal region 160 may have channels or grooves 164 extending along at least a portion of length of the shaft 159 to allow fluid to flow along the channels 164 even if the vessel shrinks around the shaft 159. This may avoid unwanted pooling or stagnant irrigation fluid around the electrodes 156 and 157 which could cause overheating of the fluid and ineffective or unsafe ablation energy delivery. FIG. 34B shows a cross section of shaft 159 at a cross section location indicated on FIG. 34A, wherein the shaft 159 has a larger diameter 162 than the diameter 161 of the electrode 157 and the shaft 159 has channels 164 for fluid flow along the length of the shaft. Also shown is a guide wire lumen 326 for delivery over a guidewire 79 (shown in FIG. 34A).

Irrigation fluid may optionally be hypertonic saline, which can conduct electrical ablation energy from the electrodes 156 and 157 to the vessel wall even if the electrodes are not in contact with the wall.

Each electrode 156 and 157 may have a length in a range of 3 to 5 mm (e.g., 4 mm). The distance 158 between the electrodes may be in a range of 3 to 6 mm (e.g., 4.5 mm).

This configuration may allow ablation of tissue within the target ablation zone 58 suitable for GSN ablation.

The electrodes (123 and 124 of the device of FIG. 31, or 156 and 157 of the device of FIG. 34A) may alternatively be coiled wire electrodes made of an elastic and electrically conductive material such as spring stainless steel. Coil electrodes may improve flexibility of the distal region of the catheters allowing them to traverse a tight bend such as the bend from an azygos vein to intercostal vein. Coil electrodes may be irrigated by passing fluid from an irrigation lumen through small gaps in the coil pitch.

In some embodiments such as the device shown in FIG. 31 the ablation elements 123 and 124 are electrically conductive around the circumference of the electrodes capable of delivering ablative energy to the target region 58 of the target vessel 55 circumferentially, in other words in a radially symmetric pattern. A benefit of this feature may be that a user does not need to consider radial orientation or torque the catheter adjust radial orientation, which may reduce procedure time or user error. However, in alternative embodiments an ablation element may direct ablation energy toward a segment of the circumference, for example the segment may be less than or equal to 50% of the circumference (e.g., less than 40%, less than 30%, less than 25%). A directional ablation catheter may direct ablation energy toward a target nerve, which may require less ablation energy, reduce a risk of injuring non-target tissue, reduce pain, or reduce injury or shrinkage of the target vessel. When used to ablate a TSN or GSN from an intercostal vein, the TSN or GSN is always in the same direction relative to the vein, which is away from the vertebra and toward the lung. In some examples (not shown), a radiopaque marker of the catheter may be used to facilitate radial orientation of the catheter. The desired orientation may be the orientation in which the directed ablation energy will be aimed in a radial direction that is away from the vertebra (e.g., opposite the vertebra) and towards the lung. For example, if the target vessel is a right T11 intercostal vein, a C-arm fluoroscope may be centered on a T11 vertebra, and optionally rotated from an anterior-posterior center position (AP position) to the patient's right side to obtain an angle that is approximately orthogonal to the tangent of the vertebra. In this position, it can be desired to have the directed ablation energy aimed in a radial direction toward the C-arm head, which is where the TSN often traverses intercostal veins. The catheter may be torqued to rotate the catheter distal section 122 within the intercostal vein until the radiopaque marker indicates that the ablation energy will be aimed toward the C-arm and thus toward the target nerve. The radiopaque marker may be configured to distinguish when the radiopaque marker is rotationally aimed at a C-arm head. Since the position of the radiopaque marker is circumferentially aligned with the direction of ablation, the radiopaque marker can be used to indicate when the direction of ablation is aimed at a C-arm head. The radiopaque marker is made from a radiopaque material and is asymmetric in shape. For example, the radiopaque marker may be N-shaped. If the radiopaque marker is facing towards the C-arm head, the radiopaque marker will appear as the letter N. If the radiopaque marker is facing away from the C-arm head (e.g., toward the vertebra), the radiopaque marker will appear as a backwards letter N. If the radiopaque marker is sideways in relation to the C-arm, the radiopaque marker will appear as a line. Optionally, a device may further include an additional radiopaque marker that is configured to visually indicate when the rotational position of the catheter's distal section 84 is within a set tolerance. Particularly, the additional radiopaque marker can include two lines the center of which is circumferentially spaced from the first radiopaque marker by about 180 degrees, so that the first radiopaque marker appears between the lines of the additional radiopaque marker when the orientation is within the set tolerance. When the orientation is outside the set tolerance, the radiopaque marker will overlap one of the lines of the additional radiopaque marker or will be outside of the lines of the additional radiopaque marker. For example, the set tolerance may be up to 45 degrees on either side of perfect alignment (e.g. up to degrees, or 25 degrees, or 15 degrees, or 5 degrees).

Electrodes may be configured for directional energy delivery by electrically insulating a portion of the electrodes facing away from the ablation direction.

Methods of Treatment

In some embodiments of a GSN ablation procedure herein, the lowest intercostal vein is first targeted because in a majority of patients a fully formed GSN traverses the lowest intercostal vein within the target region that is between the adjoining azygos vein and to a distance up to 20 mm into the intercostal vein from the ostium. However, in some patients where a first ablation is not sufficient, a test may be done to assess a clinical effect and subsequent ablations of target regions at one or two additional levels may be done to achieve a clinically significant effect. For example, the following description is an exemplary method of treating heart failure in a human patient by ablating a thoracic splanchnic nerve. A distal region of an ablation catheter comprising an ablation element can be delivered to a first intercostal vein (e.g., the lowest intercostal vein, a T11 intercostal vein) of the patient. Ablation energy can then be delivered from the ablation catheter to create a first lesion (e.g., a lesion having a length in a range of 10 to 20 mm, e.g., in a range of 12 to 15 mm) in tissue up to 5 mm from the first intercostal vein. The distal region of the ablation catheter can be moved to a second intercostal vein that is superior to (e.g., superior to and adjacent to) the first intercostal vein. An ablation confirmation test can then be performed. Monitoring can be performed for a physiological response (e.g., splanchnic vasoconstriction, increased heart rate, increased blood pressure) to the ablation confirmation test. If the physiological response demonstrates that the first lesion did not provide a clinically significant amount of GSN blocking (e.g., by observing a lack of physiological response) then ablation energy can be delivered from the ablation catheter to create a second lesion in tissue up to 5 mm from the second intercostal vein. The distal region of the ablation catheter can be moved to a third intercostal vein that is superior to (e.g., superior and adjacent to) the second intercostal vein. The same or different ablation confirmation test can be performed, followed by another monitoring test. If the physiological response demonstrates that the first lesion and second lesion did not provide a clinically significant amount of GSN blocking (e.g., by observing a lack of physiological response) then ablation energy can be delivered from the ablation catheter to create a third lesion in tissue up to 5 mm from the third intercostal vein. Any of the the ablation confirmation tests may comprise delivering a nerve stimulation signal from a stimulation electrode positioned on the distal region of the ablation catheter configured to generate an action potential in the thoracic splanchnic nerve. Alternatively or in addition to, the ablation confirmation test may comprise a leg raise test. Alternatively or in addition to, the ablation confirmation test may comprise adding fluid volume to the venous system. Alternatively or in addition to, the ablation confirmation test may comprise a hand-grip test.

In exemplary methods in which an ablation confirmation test includes a leg raise test, the method may comprise any of the following steps. Prior to ablation in the lowest intercostal vein, a baseline measurement may be obtained by raising the legs and measuring the change in central venous pressure and waiting for equilibration, that is a measure of the total venous compliance including the central veins and splanchnic bed. The legs can then be lowered, to allow equilibration so blood redistributes back to the legs. An ablation in the lowest intercostal vein (e.g. T11) can then be performed as set forth herein. The legs can then be raised, followed by waiting for equilibration and re-measure central venous pressure. A measurement can then be made to determine if there was an appropriate reduction in total venous compliance. If yes, then the GSN has successfully been ablated. If no, then an ablation in the next higher intercostal vein (e.g., T10) can be performed, as set forth herein. The measurement can be repeated. A determination can then be made to see if there was an appropriate reduction in total venous compliance. If yes, then the GSN has successfully been ablated. If no, then an ablation in the next higher intercostal vein (e.g., T9) can be performed.

In exemplary methods in which an ablation confirmation test comprises a hand-grip or other activity that increases sympathetic nervous system (SNS) outflow to the splanchnic bed may comprise the following steps. An ablation can be performed in a lowest intercostal vein (e.g., T11). Venous compliance can then be measured. A hand-grip can then be performed for a predetermined amount of time (e.g., 60 seconds). Venous compliance can then be remeasured. If there is no change in venous compliance, the initial ablation was sufficient to achieve a clinically significant outcome. If there still is a decrease in compliance, some of the SNS activity caused by the hand-grip is getting through. The ablation in the lowest intercostal vein was thus insufficient to achieve a clinically significant effect. An ablation in the next higher intercostal vein (e.g., T10) can then be performed. A hand grip test for a predetermined amount of time (e.g., 60 seconds) can be performed. Venous compliance can then be remeasured. If there is no change in compliance, the second ablation was sufficient. If there is a decrease in compliance, some of the SNS activity caused by the hand-grip is getting through, and the ablation in the next higher intercostal vein was thus insufficient to achieve a clinically significant effect. Ablation is the next higher intercostal vein (T9) can then be performed. The procedure is done at this point as ablation at a level higher than the 3rd lowest intercostal vein is not anticipated.

An ablation confirmation test may include delivering a nerve stimulation signal and monitoring and assessing a physiological response. Any of the methods of use described herein may further comprise a nerve stimulation step. For example, the electrodes used for ablation or other electrodes may be used to deliver one or more nerve stimulation signals. For example, the proximal and distal electrodes (123 and 124 of FIGS. 31 and 33, or 156 and 157 of FIG. 34A) may be used to deliver one or more nerve stimulation signals. Each electrode is electrically connected via independent conductors (not shown) travelling through the catheter to the proximal end of the catheter where they are connectable to a nerve stimulation signal supply, which may also be a computer controlled RF ablation energy console. The console may switch between delivering a stimulation signal and ablation signals so the electrodes may be used for either stimulation or ablation. In use the electrodes (e.g., 123 and 124 of FIG. 31) may be positioned at a proximal and distal end of a target region 58 of a target vessel 55, which can be visualized for example with fluoroscopy by placing the proximal electrode (e.g., 123 of FIG. 31) at the ostium 59 of the target vessel 55 as shown in FIG. 31 or FIG. 34A for example. The nerve stimulation electrodes may deliver a nerve stimulation signal in bipolar mode concentrating the signal between the two electrodes to generate an action potential of a nerve positioned between them and also within a predicted ablation zone. The distance between the two nerve stimulation electrodes of no more than 25 mm (e.g., 4 to 6 mm) ensures a pacing vector having a nerve stimulation signal strength capable of stimulating a nerve within the vector. Nerve stimulation (i.e., pacing) parameters may include 50 Hz and 1V used to generate an action potential of a TSN or GSN. Stimulation of a TSN or GSN may result in a measurable physiological response for example an epigastric response such as contraction of the rectus abdominis muscle, increased heart rate, or increased blood pressure. A positive stimulation of a TSN or GSN can confirm the ablation element is in an appropriate location to ablate the targeted TSN or GSN while lack of response can suggest the ablation element needs to be moved. Nerve stimulation parameters may include 2 Hz and 2V used to stimulate intercostal nerves or the sympathetic trunk to confirm clearance from intercostal nerves when a lack of intercostal muscle response is measured or to confirm clearance from the sympathetic trunk when a lack of response from sympathetic trunk is measured. The electrodes may optionally or alternatively be used to measure bioimpedance and phase of tissue in the pacing range which can be used to detect presence of nerve tissue, detect tissue changes caused by ablation, detect abrupt impedance changes which may be predictive of ensuing safety concerns (e.g., blood coagulation, overheating, bubble formation). Optionally, a nerve stimulation signal may have features that reduce or eliminate stimulation of pain fibers and yet stimulate a target TSN or GSN.

In any of the methods herein, including ablation confirmation tests herein, not all of the steps need necessarily to be performed. And some of the steps may occur in different orders. It is of note that the procedures herein are intending to target particular nerves or nerve roots, and are doing so from particular target veins, and even within those veins are placing ablation elements or members within certain regions. The anatomical regions that are being accessed and targeted necessitate certain design requirements. In other treatments that are targeting different anatomical locations for placement, and targeting different target nerves, the device design constraints for those approaches are very different, and thus the devices that can be used in those treatments may be very different. The disclosure herein thus provides specific reasons for designing particular devices, and those reasons include being able to effectively carry out the treatments specifically set forth herein.

While the above description provides examples of one or more processes or apparatuses, it will be appreciated that other processes or apparatuses may be within the scope of the accompanying claims.

Even if not specifically indicated, one or more techniques described in this disclosure may be implemented, at least in part, in hardware, software, firmware or any combination thereof. For example, various aspects of or more techniques or components may be implemented within one or more processors, including one or more microprocessors, digital signal processors (DSPs), application specific integrated circuits (ASICs), field programmable gate arrays (FPGAs), programmable logic circuitry, or the like, either alone or in any suitable combination. The term "processor" or "processing circuitry" may generally refer to any of the foregoing circuitry, alone or in combination with other circuitry, or any other equivalent circuitry.

Such hardware, software, or firmware may be implemented within the same device or within separate devices to support relevant various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to systems, devices and techniques described in this disclosure may be embodied as instructions on a computer-readable medium such as random access memory (RAM), read only memory (ROM), non-volatile RAM (NVRAM), electrically erasable programmable ROM (EEPROM), Flash memory, and the like. The instructions may be executed by a processor to support one or more aspects of the functionality described in this disclosure.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

Specific embodiments described herein are not intended to limit any claim and any claim may cover processes or apparatuses that differ from those described below, unless specifically indicated otherwise. The claims are not limited to apparatuses or processes having all of the features of any one apparatus or process described below or to features common to multiple or all of the apparatuses described below, unless specifically indicated otherwise. It is possible that an apparatus or process described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

What is claimed is:

1. A device for endovascular vein puncture, comprising:
    an elongate catheter extending along a longitudinal catheter axis and having a catheter proximal portion and a catheter distal portion;
    a needle guide having a blunt needle guide distal end, wherein the needle guide is deployable from the catheter from a needle guide storage position to a needle guide working position, wherein in the needle guide working position, the needle guide distal end is radially spaced from the catheter, and in the needle guide storage position, the needle guide distal end is withdrawn towards the catheter relative to the needle guide working position;
    a needle having a sharp puncturing end, wherein the needle is deployable from within the needle guide from a needle storage position to a puncturing position, wherein in the needle storage position, the sharp puncturing end is shy of the needle guide distal end, and in the puncturing position, the sharp puncturing end extends proud of the needle guide distal end; and
    an ablation energy delivery device deployable from within the needle from an ablation energy delivery device storage position to an ablation energy delivery device treatment position, wherein the ablation energy delivery device has a blunt delivery device distal end,
    wherein when in the needle guide working position, the puncturing position, and the ablation energy delivery device treatment position, the needle guide, the needle, and the ablation energy delivery device, respectively, are co-axial, and
    wherein when in the ablation energy delivery device treatment position, the ablation energy delivery device has a straight configuration where it extends from the needle.

2. The device of claim 1, wherein the ablation energy delivery device is at least one of a fluid delivery device, a thermal energy delivery device, a radiofrequency energy delivery device, a cryogenic energy delivery device, and an electrical energy delivery device.

3. The device of claim 1, wherein in the ablation energy delivery device treatment position, the ablation energy delivery device distal end extends proud of the sharp puncturing end by a delivery distance that is greater than a needle puncturing distance.

4. The device of claim 3, wherein the delivery distance is between about 3 mm and about 15 mm.

5. The device of claim 4, wherein the delivery distance is between about 4 mm and about 6 mm.

6. The device of claim 1, wherein:
    the catheter has a catheter outer diameter,
    in the puncturing position, the sharp puncturing end is spaced from the blunt needle guide distal end by a needle deployed distance that is less than the catheter outer diameter, and
    in the needle guide working position, the blunt needle guide distal end is spaced from the catheter in the radial direction by a needle guide deployed distance that is less than the catheter outer diameter.

7. The device of claim 6, wherein the needle deployed Distance is less than 2 mm.

8. The device of claim 7, wherein the needle deployed distance is less than 1 mm.

9. The device of claim 6, wherein the needle guide deployed distance is between about 0.5 mm and 6 mm.

10. The device of claim 9, wherein the needle guide deployed distance is between about 0.5 mm and about 3 mm.

11. The device of claim 9, wherein the needle guide deployed distance is between about 2 mm and about 6 mm.

12. The device of claim 6, wherein the catheter diameter plus the needle guide deployed distance, when the needle guide is fully deployed, is equal to a distance in a range of 2 mm to 4 mm.

13. The device of claim 6, wherein the catheter diameter plus the needle guide deployed distance, when the needle guide is fully deployed, is equal to a distance in a range of 3.5 mm to 6.5 mm.

14. The device of claim 1, wherein the catheter comprises a circumferential outer surface and a first side port in the circumferential outer surface, and the needle guide is deployable from the first side port.

15. The device of claim 1, wherein the catheter comprises a guidewire lumen extending therethrough, along the catheter axis, and the catheter distal portion has a guidewire exit port; and wherein the catheter comprises a distal end surface and a circumferential outer surface, and the guidewire exit port comprises a notch that is open at and between the distal end surface and the circumferential surface.

16. The device of claim 15, wherein
the needle guide is deployable from the catheter at a first circumferential position on the catheter,
the notch is open at the circumferential surface at a notch circumferential position that is within 30 degrees of the first circumferential position, and
the notch circumferential position is aligned with the first circumferential position.

17. The device of claim 1, further comprising:
a second needle guide deployable from the catheter; and
a second needle deployable from within the second needle guide,
wherein the needle guide is deployable from the catheter at a first longitudinal position on the catheter, and the second needle guide is deployable from the catheter at a second longitudinal position on the catheter, wherein the second longitudinal position is longitudinally spaced from the first longitudinal position along a longitudinal axis, and
wherein the needle guide is deployable from the catheter at a first circumferential position on the catheter, and the second needle guide is deployable from the catheter at a second circumferential position on the catheter, wherein the second circumferential position is circumferentially aligned with the first circumferential position.

18. The device of claim 17, wherein the needle guide and the needle are longitudinally spaced apart from a notch at the distal end by a spacing of between 1.5 cm and about 2.5 cm, and wherein the second longitudinal position is spaced from the first longitudinal position by a spacing of between about 3 cm and about 5 cm.

* * * * *